US009636670B2

(12) United States Patent
Fletcher et al.

(10) Patent No.: US 9,636,670 B2
(45) Date of Patent: May 2, 2017

(54) CATALYSTS, LIGANDS AND USE THEREOF

(71) Applicants: Stephen Patrick Fletcher, Oxford (GB); Rebecca Marie Maksymowicz, Oxford (GB); Philippe Marie-Christophe Roth, Oxford (GB); Mireia Sidera Portela, Oxford (GB)

(72) Inventors: Stephen Patrick Fletcher, Oxford (GB); Rebecca Marie Maksymowicz, Oxford (GB); Philippe Marie-Christophe Roth, Oxford (GB); Mireia Sidera Portela, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 14/784,997

(22) PCT Filed: Apr. 10, 2014

(86) PCT No.: PCT/GB2014/051127
§ 371 (c)(1),
(2) Date: Oct. 16, 2015

(87) PCT Pub. No.: WO2014/170642
PCT Pub. Date: Oct. 23, 2014

(65) Prior Publication Data
US 2016/0074852 A1 Mar. 17, 2016

(30) Foreign Application Priority Data
Apr. 18, 2013 (GB) .................................. 1307049.5

(51) Int. Cl.
C07F 7/04 (2006.01)
B01J 31/18 (2006.01)
B01J 31/02 (2006.01)
C07C 45/69 (2006.01)
C07F 7/08 (2006.01)
C07F 9/6571 (2006.01)

(52) U.S. Cl.
CPC ....... *B01J 31/1855* (2013.01); *B01J 31/0224* (2013.01); *B01J 31/188* (2013.01); *C07C 45/69* (2013.01); *C07F 7/083* (2013.01); *C07F 9/6571* (2013.01); *B01J 2231/32* (2013.01); *B01J 2231/323* (2013.01); *B01J 2231/349* (2013.01); *B01J 2531/16* (2013.01); *C07C 2101/08* (2013.01); *C07C 2101/14* (2013.01); *C07C 2101/16* (2013.01); *C07C 2101/18* (2013.01); *C07C 2102/28* (2013.01)

(58) Field of Classification Search
CPC .. B01J 31/18; C07C 45/69; C07F 7/08; C07F 9/6571
USPC ........................................................ 556/436
See application file for complete search history.

(56) References Cited

FOREIGN PATENT DOCUMENTS

| DE | 102004062640 B4 | 1/2009 |
|---|---|---|
| EP | 1364932 B1 | 5/2008 |
| JP | 2001-294577 A | 10/2001 |
| JP | 2001-294578 A | 10/2001 |
| WO | 02/04466 A2 | 1/2002 |
| WO | 2004/024684 A2 | 3/2004 |
| WO | 2005/111050 A2 | 11/2005 |
| WO | 2013/054131 A1 | 4/2013 |

OTHER PUBLICATIONS

International Search Report, PCT/GB2014/051127; mailed Dec. 19, 2014.*
Written Opinion of the International Searching Authority, PCTASA/220 (International application No. PCT/GB2014/051127; Dec. 19, 2014).*
Muller et al., Organic Letters, 1999, 1(3), 439-442.*
Maksymowicz, R.M., et al., Hydrometallation-asymmetric conjugate addition: application to complex molecule synthesis, Chemical Communications, Jan. 1, 2013, 3 pages.
Müller, P., et al., Copper-Catalyzed Desymmetrization of N-Sulfonylaziridines with Methylmagnesium Halides, Organic Letters, Aug. 1, 1999, vol. 1, No. 3, pp. 439-442.
Chengyan, N. et al., Eriantioselective Conjugate Addition of Diethylzinc to Vinylogous Imines Generated in situ from Sulfonyl Indoles, Chinese Journal of Organic Chemistry, 2012, vol. 32, No. 12, pp. 2322-2327.
Park, H.S., et al., Asymmetric hydrosilyiation of cyclohexa-1,3-diene with trichlorosilane by palladium catalysts coordinated with chiral phosphoramidite ligands, Tetrahedron: Asymmetry, Apr. 1, 2013, vol. 24, No. 7, pp. 418-420.
Shintani, R., et al., Rhodium-Catalyzed Asymmetric [5+2] Cycloaddition of Alkyne-Vi nylcyclopropanes Chemistry—a European Journal, Sep. 7, 2009, vol. 15, No. 35, pp. 8692-8694.
Shi, C., et al., Asymmetric synthesis of 1-vinyltetrahydroisoquinoline through Pd-catalyzed intramolecular allylic amination, Tetrahedron, Aug. 1, 2007; vol. 63, No. 35, pp. 8563-8570.
Sidera, M., et al., Formation of Quaternary Centers by Copper-Catalyzed Asymmetric Conjugate Addition of Alkylzirconium Reagents, Angewandte Chemie International Edition, Jun. 18, 2013, vol. 52, No. 31, pp. 7995-7999.

* cited by examiner

Primary Examiner — Pancham Bakshi
Assistant Examiner — Kofi Adzamli
(74) Attorney, Agent, or Firm — Hodgson Russ LLP

(57) ABSTRACT

According to the present invention, there is provided a catalytic complex comprising a metal, one or more ligands and one or more counterions, wherein said one or more ligands include a non-racemic chiral ligand and wherein said one or more counterions include a triflimide counterion. Also provided are methods of making said catalytic complex and processes for producing chiral compounds which involve the use of said catalytic complex. In addition, the present invention provides compounds of the formula (2) as defined herein. The compounds of formula (2) may be useful as ligands in catalytic complexes.

21 Claims, No Drawings

CATALYSTS, LIGANDS AND USE THEREOF

FIELD OF THE INVENTION

This invention relates to catalysts and their use in processes for producing organic compounds. More particularly, the present invention relates to catalysts suitable for use in the asymmetric synthesis of chiral compounds. The present invention also relates to ligands suitable for use in such catalysts.

BACKGROUND TO THE INVENTION

The development of catalytic methods for asymmetric synthesis is one of the foremost achievements in recent chemistry. At present, many broadly useful methods for catalytic asymmetric oxidation and reduction exist; however, far fewer catalytic asymmetric methods for forming carbon-carbon bonds have been devised. This is not only remarkable in view of the importance of carbon-carbon bond formation in synthesis, but also reflects the major difficulties and challenges associated with enantioselective versions of these transformations. The development of asymmetric carbon-carbon bond forming reactions that are new, powerful and practical is of great importance.

Asymmetric conjugate addition reactions with organometallic reagents are one of the most powerful reactions in chemistry. The use of organozincs and Grignard reagents, readily available from alkylhalides, has made asymmetric catalytic carbon-carbon bond formation based on organometallic reagents practical. However, whilst the use of organozincs and Grignard reagents means that obscure reagents are no longer required, these reagents are still far from ideal. Organometallic procedures have been extensively developed, but suffer from a number of significant limitations. For instance, in the synthesis of complex molecules, functional groups may be present which are incompatible with organometallic reagents. Even the use of a protecting group strategy, which blocks incompatible reaction sites, is often ineffective, due to the reactivity of organometallic reagents and the extreme sensitivity of many asymmetric procedures. Moreover, the reactivity of organometallic reagents is associated with serious safety issues. Asymmetric procedures are typically highly sensitive to reaction conditions such that only particular solvents may be used. Asymmetric organometallic addition reactions must be also be performed at cryogenic temperatures (e.g. less than −30° C.) for high levels of selectively to be obtained. This is not usually possible in industry and so represents a serious limitation of these methods. The aforementioned methods are generally too reactive, too expensive and/or of limited availability.

Particular problems are encountered in the enantioselective synthesis of all-carbon quaternary centres. The ability to construct quaternary centres with high levels of enantioselectivity is widely regarded as one of the most important and challenging goals in asymmetric catalysis. Current approaches to this problem involve transition-metal catalysed asymmetric conjugate addition reactions to trisubstituted Michael acceptors. However, once again, such techniques rely on the use of highly reactive pre-made organometallic reagents that can present practical and safety issues. The use of functionalized nucleophiles in these procedures, essential for providing products ready for further elaboration, can also be problematic because of the incompatibility of functional groups with organometallic reagents.

Maksymowicz et al (Nature Chemistry, 2012, 4, 649-654) describe a catalytic asymmetric conjugate addition process in which carbon-carbon bond formation is achieved using alkenes as alkylmetal equivalents. The disclosed process involves the use of a catalytic complex comprising a metal source (e.g. a copper source) and a non-racemic chiral ligand (e.g. a phosphoramidite ligand).

There exists a need in the art for further catalysts for use in processes for the asymmetric synthesis of organic compounds. In particular, there exists a need in the art for improved catalysts for use in such processes.

SUMMARY OF THE INVENTION

According to a first aspect of the present invention, there is provided a catalytic complex comprising a metal, one or more ligands and one or more counterions, wherein said one or more ligands include a non-racemic chiral ligand and wherein said one or more counterions include a triflimide counterion.

In other aspects, the present invention relates to processes for producing chiral compounds in a stereoisomeric excess, which processes involve the use of the present catalytic complexes. In embodiments, the chiral compounds are produced via a 1,4-conjugate addition reaction or a 1,6-conjugate addition reaction. Methods of producing the catalytic complexes of the invention are also provided.

The use of a triflimide anion as a counterion may result in enhanced stereoselectivity and provide for an increased stereoisomeric excess in asymmetric reactions, particularly in asymmetric conjugate addition reactions. Thus, the present complexes may allow for the production of chiral compounds in a high stereoisomeric excess, e.g. a high enantiomeric excess, and may be tolerant to a wide range of solvents and/or functional groups. The present complexes may be particularly advantageous in the asymmetric synthesis of chiral compounds containing quaternary centres at a chiral carbon atom.

In another aspect, the present invention provides a compound of the formula (2):

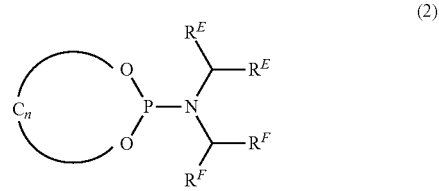

wherein:
the moiety —O—$C_n$—O— is chiral and is an aliphatic or aromatic diolate, wherein said diolate is optionally substituted;
each $R^E$ is the same and is an achiral organic group; or $R^E$ and $R^E$, together with the carbon atom to which they are attached, form an achiral cyclic organic group;
each $R^F$ is the same and is an achiral organic group; or $R^F$ and $R^F$, together with the carbon atom to which they are attached, form an achiral cyclic organic group; and
the moieties —$CH(R^E)_2$ and —$CH(R^F)_2$ as shown in formula (2) are different; or a salt thereof.

In other aspects, the present invention relates to a process for producing a chiral compound in a stereoisomeric excess, which process involves the use of a catalytic complex comprising a compound of formula (2) as a ligand. In embodiments, the chiral compound is produced via a 1,4-conjugate addition reaction or a 1,6-conjugate addition reaction. Methods of producing compounds of formula (2) are also provided. Advantageously, the compounds of formula (2) can be readily prepared and may not require the transformation of a chiral non-racemic amine or the separation of diastereomers during preparation. The compounds may also exhibit desirable stereoselectivity when employed as ligands in catalytic complexes for use in asymmetric synthesis.

DESCRIPTION OF VARIOUS EMBODIMENTS

For the purposes of the present invention, the following terms as used herein shall, unless otherwise indicated, be understood to have the following meanings.

The term "alkyl" as used herein refers to a straight or branched chain alkyl moiety having from 1 to 30 carbon atoms. For instance, an alkyl group may have from 1 to 20 carbon atoms, e.g. from 1 to 12 carbon atoms, e.g. from 1 to 10 carbon atoms. In particular, an alkyl group may have 1, 2, 3, 4, 5 or 6 carbon atoms (referred to herein as $C_{1-6}$ alkyl). Examples of alkyl groups include methyl, ethyl, propyl (n-propyl or isopropyl), butyl (n-butyl, sec-butyl or tert-butyl), pentyl, hexyl and the like. The term "alkylene" as used herein refers to a divalent alkyl moiety.

The term "alkenyl" as used herein refers to a straight or branched chain alkyl group having from 2 to 30 carbon atoms and having, in addition, at least one carbon-carbon double bond, of either E or Z stereochemistry where applicable. For instance, an alkenyl group may have from 2 to 20 carbon atoms, e.g. from 2 to 12 carbon atoms, e.g. from 2 to 10 carbon atoms. In particular, an alkenyl group may have 2, 3, 4, 5 or 6 carbon atoms. Examples of alkenyl groups include ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl and the like.

The term "alkynyl" as used herein refers to a straight or branched chain alkyl group having from 2 to 30 carbon atoms and having, in addition, at least one carbon-carbon triple bond. For instance, an alkynyl group may have from 2 to 20 carbon atoms, e.g. from 2 to 12 carbon atoms, e.g. from 2 to 10 carbon atoms. In particular, an alkynyl group may have 2, 3, 4, 5 or 6 carbon atoms. Examples of alkynyl groups include ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl, 3-hexynyl and the like.

The term "carbocyclyl" as used herein refers to a saturated (e.g. cycloalkyl) or unsaturated (e.g. cycloalkenyl or aryl) carbocyclic ring moiety having from 3 to 30 carbon atoms. For instance, a carbocyclyl group may have from 3 to 20 carbon atoms, e.g. from 3 to 16 carbon atoms, e.g. from 3 to 10 carbon atoms. In particular, a carbocyclyl group may be a 5- or 6-membered ring system, which may be saturated or unsaturated. Examples of carbocyclic groups include cyclopropyl, cyclobutyl, cyclopentyl, cyclohexyl, phenyl, naphthyl, fluorenyl, azulenyl, indenyl, anthryl and the like.

The term "cycloalkyl" as used herein refers to an aliphatic carbocyclic moiety having from 3 to 20 ring carbon atoms. For instance, a cycloalkyl group may have from 3 to 16 carbon atoms, e.g. from 3 to 10 carbon atoms. In particular, a cycloalkyl group may have 3, 4, 5 or 6 ring carbon atoms. A cycloalkyl group may be a monocyclic, polycyclic (e.g. bicyclic) or bridged ring system. Examples of cycloalkyl groups include cyclopropyl, cyclobutyl, cyclopentyl, cyclohexyl, norbornyl and the like.

The term "cycloalkenyl" as used herein refers to an aliphatic carbocyclic moiety having from 5 to 20 ring carbon atoms and having, in addition, at least one carbon-carbon double bond in the ring. For instance, a cycloalkenyl group may have from 5 to 16 carbon atoms, e.g. from 5 to 10 carbon atoms. In particular, a cycloalkenyl group may have 5 or 6 ring carbon atoms. A cycloalkenyl group may be a monocyclic, polycyclic (e.g. bicyclic) or bridged ring system. Examples of cycloalkenyl groups include cyclopentenyl, cyclohexenyl and the like.

The term "aryl" as used herein refers to an aromatic carbocyclic ring system having from 6 to 30 ring carbon atoms. For instance, an aryl group may have from 6 to 16 ring carbon atoms, e.g. from 6 to 10 ring carbon atoms. An aryl group may be a monocyclic aromatic ring system or a polycyclic ring system having two or more rings, at least one of which is aromatic. Examples of aryl groups include phenyl, naphthyl, fluorenyl, azulenyl, indenyl, anthryl and the like.

The term "aralkyl" as used herein refers to an alkyl group substituted with an aryl group, wherein the alkyl and aryl groups are as defined herein. An example of an aralkyl group is benzyl.

The term "heterocyclyl" as used herein refers to a saturated (e.g. heterocycloalkyl) or unsaturated (e.g. heterocycloalkenyl or heteroaryl) heterocyclic ring moiety having from 3 to 30 ring atoms, wherein said ring atoms include at least one ring carbon atom and at least one ring heteroatom selected from nitrogen, oxygen, phosphorus, silicon and sulphur. For instance, a heterocyclyl group may have from 3 to 20 ring atoms, e.g. from 3 to 16 ring atoms, e.g. from 3 to 10 ring atoms. In particular, a heterocyclyl group may have 5 or 6 ring atoms, and may be saturated or unsaturated. Examples of heterocyclic groups include imidazolyl, thienyl, furyl, tetrahydrofuryl, pyranyl, thiopyranyl, thianthrenyl, isobenzofuranyl, chromenyl, pyrrolyl, pyrrolinyl, pyrrolidinyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, indolyl, cumaryl, indazolyl, triazolyl, tetrazolyl, purinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, phenanthridinyl, acridinyl, perimidinyl, phenanthrolinyl, furazanyl, phenazinyl, phenothiazinyl, phenoxazinyl, chromenyl, isochromanyl, oxiranyl, azirinyl, 1,2-oxathiolanyl, chromanyl and the like.

The term "heterocycloalkyl" as used herein refers to a saturated heterocyclic moiety having from 3 to 10 ring carbon atoms and 1, 2, 3, 4 or 5 ring heteroatoms selected from nitrogen, oxygen, phosphorus and sulphur. The group may be a monocyclic or polycyclic ring system. Examples of heterocycloalkyl groups include azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl, tetrahydropyranyl, and the like.

The term "heterocycloalkenyl" as used herein refers to a saturated heterocyclic moiety having from 3 to 10 ring carbon atoms and 1, 2, 3, 4 or 5 ring heteroatoms selected from nitrogen, oxygen, phosphorus and sulphur, and having, in addition, at least one carbon-carbon double bond in the ring. The group may be a monocyclic or polycyclic ring system. An example of a heterocycloalkenyl group is pyranyl.

The term "heteroaryl" as used herein refers to an aromatic heterocyclic ring system having from 5 to 30 ring atoms, wherein said ring atoms include at least one ring carbon atom and at least one ring heteroatom selected from nitrogen, oxygen and sulphur. The group may be a monocyclic ring system or a polycyclic (e.g. bicyclic) ring system having two or more rings, at least one of which is aromatic. Examples of heteroaryl groups include pyridazinyl, pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, isoquinolinyl, quinazolinyl and the like.

The terms "halogen" and "halo" as used herein refer to F, Cl, Br or I.

The term "optionally substituted" as used herein means unsubstituted or substituted.

The term "substituted" as used herein in connection with a chemical group means that one or more (e.g. 1, 2, 3, 4 or 5) of the hydrogen atoms in that group are replaced independently of each other by a corresponding number of substituents. It will, of course, be understood that the one or more substituents may only be at positions where they are chemically possible, i.e. that any substitution is in accordance with permitted valence of the substituted atom and the substituent, and that the substitution results in a stable compound. The term is contemplated to include all permissible substituents of a chemical group or compound. It will be understood by those skilled in the art that one or more hydrogen atoms on a given substituent can themselves be substituted, if appropriate.

Examples of substituents include acyl, alkoxy, alkoxycarbonyl, alkylamino, alkylsulfinyl, alkylsulfonyl, alkylthio, amino, aminoalkyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy. In an embodiment, said one or more substituents are each independently selected from $C_{1-6}$ alkyl (e.g. methyl), aryl, halo and hydroxy.

Where two or more moieties are described as being "each independently" selected from a list of moieties, this means that the moieties may be the same or different. The identity of each moiety is therefore independent of the identities of the one or more other moieties. Where multiple substituents are indicated as being attached to a structure, it will be understood that the substituents can be the same or different.

The term "electron withdrawing group" as used herein refers to any atom or group having an electronegativity greater than that of a hydrogen atom, wherein electronegativity is as defined on the Pauling scale. A quantification of the level of electron withdrawing capability is given by the Hammett sigma ($\sigma$) constant. This constant is well known in the art (see e.g. "Advanced Organic Chemistry", J. March, McGraw Hill, New York, 2007). The Hammett sigma constant values are generally positive for electron withdrawing groups.

The term "$\pi$-bond" as used herein refers to a chemical bond formed by the overlap of p orbitals on adjacent atoms, perpendicular to any sigma ($\sigma$) bonds between the same atoms. A $\pi$-bond is generally a double or triple bond. Examples of $\pi$-bonds include C=O, C=C, C=O, C=N, C=N, N=O and S=O bonds.

The term "alkene bond" as used herein refers to an aliphatic carbon-carbon double (C=C) bond.

The term "organic group" as used herein refers to a chemical group comprising at least one carbon atom and one or more atoms in addition, e.g. one or more atoms selected from hydrogen, oxygen, nitrogen, sulphur, phosphorus, halogen, silicon, boron and combinations thereof. Examples of organic groups include alkyl, aryl, aralkyl, cycloalkyl, cycloalkenyl, heterocyclyl and combinations thereof, wherein any of said groups may be unsubstituted or substituted by one or more substituents.

In a first aspect, the present invention provides a catalytic complex comprising a metal, one or more ligands and one or more counterions, wherein said one or more ligands include a non-racemic chiral ligand and wherein said one or more counterions include a triflimide counterion. In this regard, the use of a triflimide anion (i.e. $[N(SO_2CF_3)_2]^-$; also referred to herein as "$NTf_2^-$") as a counterion may result in improved stereoselectivity and provide for an increased stereoisomeric excess in asymmetric reactions, particularly in asymmetric conjugate addition reactions.

The catalytic complex according to said first aspect of the invention contains one or more counterions, at least one of which is a triflimide anion. The one or more counterions serve to provide electroneutrality to the catalytic complex and will typically be non-coordinating counterions. In embodiments, the catalytic complex comprises one or more counterions in addition to the triflimide anion. Where present, any additional counterions will normally be anionic. In embodiments, the triflimide anion is the only counterion that is present in the catalytic complex.

In an embodiment, the metal is a transition metal, e.g. selected from copper, cobalt, iridium, rhodium, ruthenium, nickel, iron, palladium, gold, silver and platinum. In a preferred embodiment, the complex comprises copper. More preferably, the metal is copper (I). The use of copper is particularly desirable as it can catalyse the conjugate addition of alkylzirconocenes formed in situ from alkenes with high overall yield.

The catalytic complex comprises one or more ligands, at least one of which is a non-racemic chiral racemic ligand. The one or more ligands will normally be bound to the metal atom via a coordinate bond. Typically, the one or more ligands will be uncharged such that they do not counter the ionic charge of any other species in the complex.

The non-racemic chiral ligand may be a chelating ligand or a non-chelating ligand. Examples of suitable ligands include phosphines, bisphosphines, amines, diamines, imines, arsines, sulfides, sulfoxides, carbenes (e.g. N-heterocyclic carbenes), peptides and hybrids thereof, including hybrids of phosphines with amines, hybrids of phosphines with peptides, and hybrids of phosphines with sulfides.

In embodiments, the catalytic complex comprises one or more other ligands in addition to the non-racemic chiral ligand. Thus, for example, it may be necessary in some instances for the catalytic complex to include one or more additional ligands in order to obtain a stable complex. In other embodiments, the non-racemic chiral ligand is the only ligand that is present in the complex.

In an embodiment, the non-racemic chiral ligand is a phosphoramidite ligand. In a particular embodiment, the non-racemic chiral ligand is a phosphoramidite ligand of the formula (1):

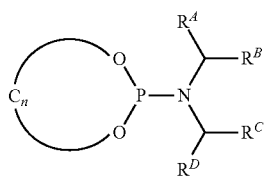

(1)

wherein:
the moiety —O—$C_n$—O— is an aliphatic or aromatic diolate, wherein said diolate is optionally substituted; and
$R^A$, $R^B$, $R^C$ and $R^D$ are each independently selected from alkyl, aryl, aralkyl, cycloalkyl, cycloalkenyl, heterocyclyl and combinations thereof, any of which is optionally substituted.

In an embodiment, the moiety —O—$C_n$—O— in formula (1) is chiral. In an embodiment, the moiety —O—$C_n$—O— exhibits axial chirality. In an embodiment, the moiety —O—$C_n$—O— is a moiety derived from a binaphthol compound. The term "moiety derived from a binaphthol compound" as used herein refers to a moiety formed by removing hydrogen atoms from the two hydroxyl groups of a binaphthol compound. The binaphthol compound may be unsubstituted or substituted by one or more substituents, in addition to the two hydroxyl groups. In an embodiment, the moiety —O—$C_n$—O— is a moiety derived from an unsubstituted binaphthol compound. In an embodiment, the binaphthol compound is partially hydrogenated. In a particular embodiment, the binaphthol compound is (R)-1,1'-bi-2-naphthol or (S)-1,1'-bi-2-naphthol.

In an embodiment, $R^A$, $R^B$, $R^C$ and $R^D$ are each independently selected from alkyl and aryl, either of which is optionally substituted.

In an embodiment, $R^A$, $R^B$, $R^C$ and $R^D$ are each independently selected from $C_{1-6}$ alkyl (e.g. methyl or ethyl) and aryl (e.g. phenyl), either of which is optionally substituted.

In an embodiment, at least one (e.g. two) of $R^A$, $R^B$, $R^C$ and $R^D$ is $C_{1-6}$ alkyl (e.g. methyl or ethyl) and the one or more others are selected from aryl (e.g. phenyl), wherein said $C_{1-6}$ alkyl and aryl groups are optionally substituted.

In an embodiment, $R^A$ and $R^D$ are each independently aryl (e.g. phenyl) and $R^B$ and $R^C$ are each independently $C_{1-6}$ alkyl (e.g. methyl or ethyl), wherein said $C_{1-6}$ alkyl and aryl groups are optionally substituted.

In an embodiment, $R^A$ and $R^B$ are each independently aryl (e.g. phenyl) and $R^C$ and $R^D$ are each independently $C_{1-6}$ alkyl (e.g. methyl or ethyl), wherein said $C_{1-6}$ alkyl and aryl groups are optionally substituted.

In an embodiment, at least one of $R^A$, $R^B$, $R^C$ and $R^D$ is substituted with one or more (e.g. 1, 2 or 3) substituents. In an embodiment, the one or more substituents are each independently selected from acyl, alkoxy, alkoxycarbonyl, alkylamino, alkylsulfinyl, alkylsulfonyl, alkylthio, amino, aminoacyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy. In an embodiment, said one or more substituents are each independently selected from $C_{1-6}$ alkyl (e.g. methyl), halo and hydroxy.

In an embodiment, each of $R^A$, $R^B$, $R^C$ and $R^D$ is unsubstituted.

In another embodiment, the non-racemic chiral ligand is a compound of the formula (2) as defined herein.

In a preferred embodiment, the non-racemic chiral ligand is a compound of the formula (A), (B), (C) or (D):

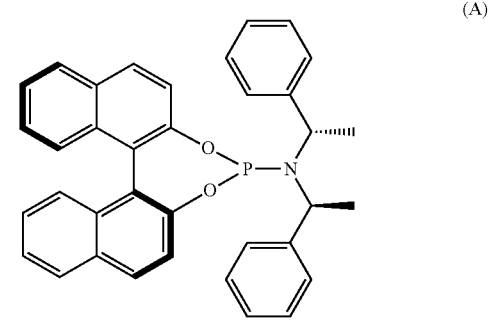

(A)

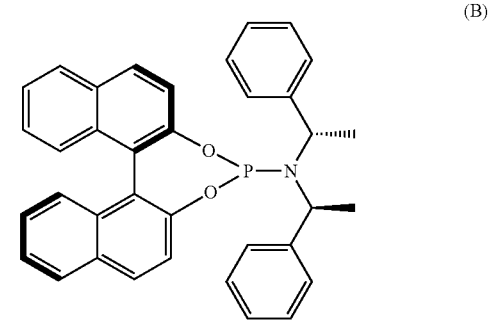

(B)

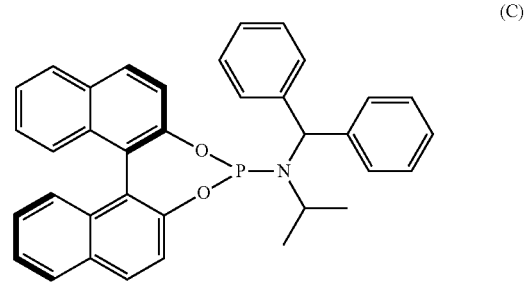

(C)

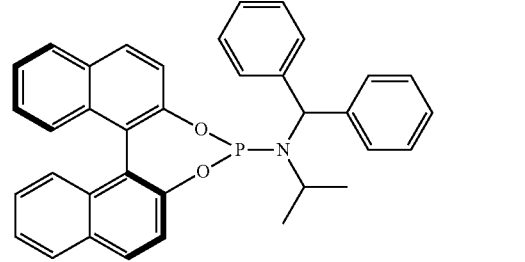

(D)

In an embodiment, the catalytic complex is of the formula MLZ, wherein M is a metal, L is a non-racemic chiral ligand and Z is a triflimide counterion. M, L and Z may be as described in any of the embodiments set forth above. In embodiments, M is copper (I). In embodiments, L is a phosphoramidite ligand, e.g. a phosphoramidite ligand of any of the formulae (1), (2), (A), (B), (C) and (D) as described herein.

In an embodiment, the catalytic complex is of one of the following formulae:

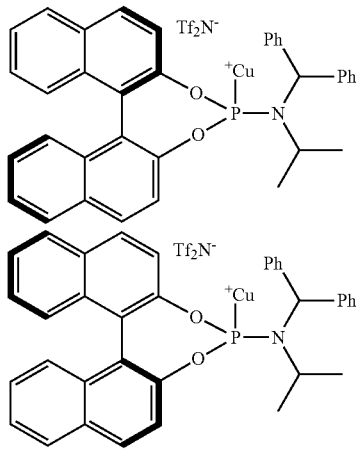

The catalytic complex may be prepared following procedures known in the art. The catalytic complex will generally be prepared by contacting a metal, the non-racemic chiral ligand and any other ligands with a triflimide anion and any other counterions. The triflimide anion is preferably in the form of a metal salt. In an embodiment, the catalytic complex is prepared by contacting a triflimide anion with a catalyst precursor in which the metal is bound to said one or more ligands. In an embodiment, the triflimide anion is in the form of a triflimide salt. Preferably, the triflimide salt is silver triflimide. In this regard, it has been found that silver triflimide complexes may be particularly effective for anion exchange with metal salts and, in particular, copper salts.

The complex may be formed as a pre-made catalyst or may be generated in situ during the course of a chemical reaction, e.g. during the course of an asymmetric conjugate addition reaction. The complex may be formed by converting a catalyst precursor into the active form. The complex may be prepared by stirring the metal, one or more ligands, one or more counterions and any other components under appropriate conditions.

Suitable processes and conditions for forming the catalytic complexes of the present invention are described in the Examples herein. By way of illustration, and without limitation, a catalytic complex comprising copper, a non-racemic chiral phosphoramidite ligand and a triflimide counterion may be prepared according to the following procedure. A copper salt and one equivalent of phosphoramidite ligand are added to a flame dried Schlenk flask, at room temperature under an argon atmosphere. Dry dichloromethane (DCM) is then added and the mixture is stirred for one hour to create a clear solution. One equivalent of silver triflimide is added to the clear solution and stirred for a further 20 minutes. On addition of silver triflimide, the solution turns grey and a silver chloride precipitate forms. The resulting solution is cannula filtrated into another Schlenk flask. The solvent is then gently removed by use of an oil-pump vacuum (with liquid nitrogen trapping). The resulting off-white solid is dried for at least one hour under oil-pump vacuum and is then stored under argon.

In another aspect, the present invention provides a compound of the formula (2):

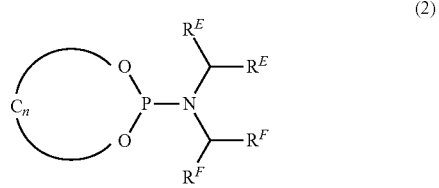

wherein:
the moiety —O—$C_n$—O— is chiral and is an aliphatic or aromatic diolate, wherein said diolate is optionally substituted;
each $R^E$ is the same and is an achiral organic group; or $R^E$ and $R^E$, together with the carbon atom to which they are attached, form an achiral cyclic organic group;
each $R^F$ is the same and is an achiral organic group; or $R^F$ and $R^F$, together with the carbon atom to which they are attached, form an achiral cyclic organic group; and
the moieties —CH($R^E$)$_2$ and —CH($R^F$)$_2$ as shown in formula (2) are different;
or a salt thereof.

In an embodiment, the moiety —O—$C_n$—O— in formula (2) exhibits axial chirality. In an embodiment, the moiety —O—$C_n$—O— is a moiety derived from a binaphthol compound. The term "moiety derived from a binaphthol compound" is as defined above. The binaphthol compound may be unsubstituted or substituted by one or more substituents, in addition to the two hydroxyl groups. In an embodiment, the moiety —O—$C_n$—O— is a moiety derived from an unsubstituted binaphthol compound. In an embodiment, the binaphthol compound is partially hydrogenated. In a particular embodiment, the binaphthol compound is (R)-1,1'-bi-2-naphthol or (S)-1,1'-bi-2-naphthol.

In an embodiment, each $R^E$ is optionally substituted aryl. In an embodiment, each $R^E$ is phenyl or naphthyl, either of which is optionally substituted. In an embodiment, each $R^E$ is phenyl, wherein said phenyl is unsubstituted or substituted with 1, 2, 3, 4 or 5 substituents independently selected from $C_{1-6}$ alkyl (e.g. methyl), halogen (e.g. fluoro), trifluoromethyl and $C_{1-6}$ alkoxy (e.g. methoxy). In an embodiment, each $R^E$ is naphthyl. In an embodiment, each $R^E$ is phenyl and the $R^E$ moieties are joined via an alkylene bridge, e.g. a $C_{1-6}$ alkylene bridge.

In an embodiment, each $R^F$ is optionally substituted alkyl, e.g. optionally substituted $C_{1-6}$ alkyl. In an embodiment, each $R^F$ is $C_{1-6}$ alkyl. In an embodiment, each $R^F$ is methyl, ethyl or propyl (isopropyl or n-propyl). In an embodiment, each $R^F$ is methyl.

In an embodiment, $R^F$ and $R^F$, together with the carbon atom to which they are attached, form an achiral cyclic organic group. In an embodiment, the achiral cyclic organic group is an optionally substituted cycloalkyl group. In an embodiment, the achiral cyclic organic group is cyclopentyl, cyclohexyl, cycloheptyl or cyclooctyl, any of which is optionally substituted. In an embodiment, the achiral cyclic organic group is cyclopentyl, cyclohexyl, cycloheptyl or cyclooctyl.

In an embodiment, each $R^E$ is optionally substituted aryl (e.g. optionally substituted phenyl or naphthyl); and each $R^F$ is optionally substituted alkyl (e.g. optionally substituted $C_{1-6}$ alkyl), or $R^F$ and $R^F$, together with the carbon atom to which they are attached, form an achiral cyclic organic group which is an optionally substituted cycloalkyl group.

In an embodiment, each $R^E$ is optionally substituted phenyl; and each $R^F$ is optionally substituted $C_{1-6}$ alkyl (e.g. methyl, ethyl or propyl), or $R^F$ and $R^F$, together with the carbon atom to which they are attached, form cyclopentyl, cyclohexyl, cycloheptyl or cyclooctyl, any of which is optionally substituted.

In an embodiment, each $R^E$ is phenyl, wherein said phenyl is unsubstituted or substituted with 1, 2, 3, 4 or 5 substituents independently selected from $C_{1-6}$ alkyl (e.g. methyl), halogen (e.g. fluoro), trifluoromethyl and $C_{1-6}$ alkoxy (e.g. methoxy); and each $R^F$ is methyl.

In an embodiment, the compound of formula (2) is selected from the following compounds:

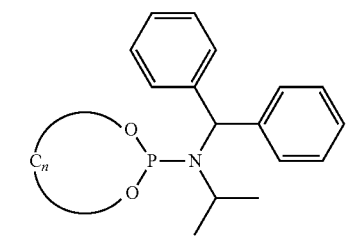

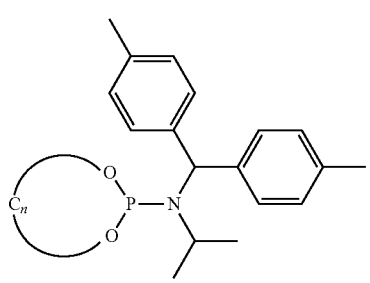

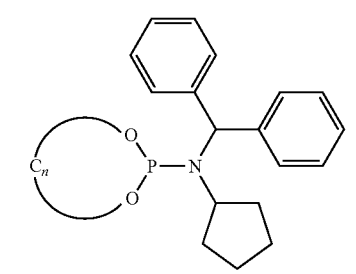

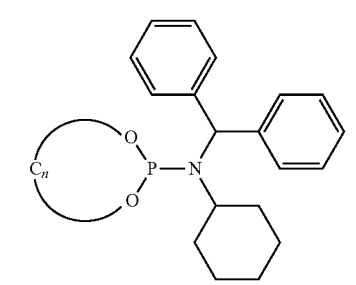

-continued

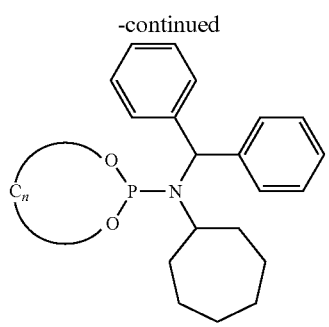

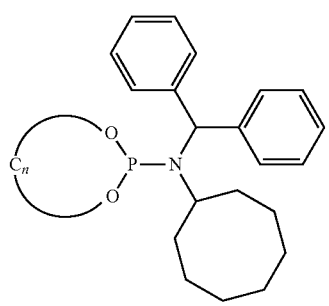

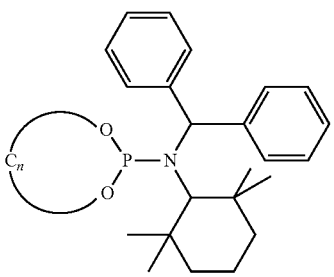

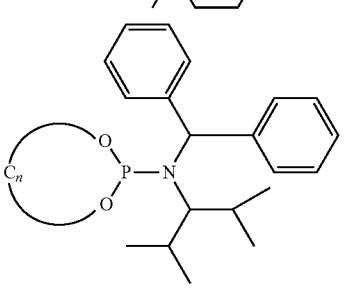

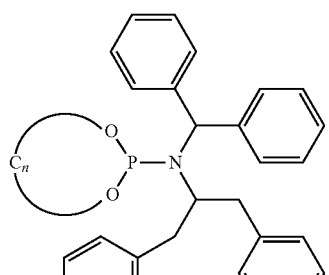

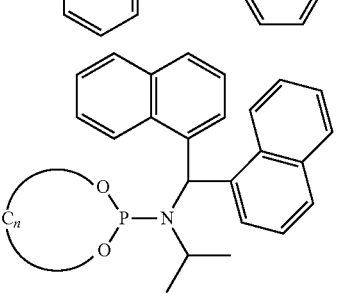

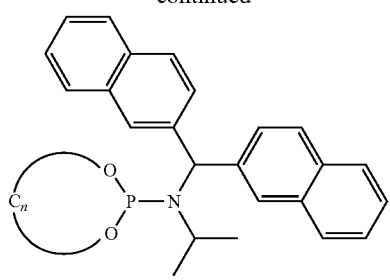
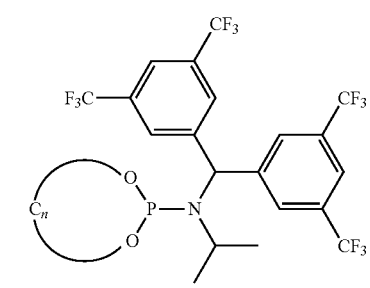
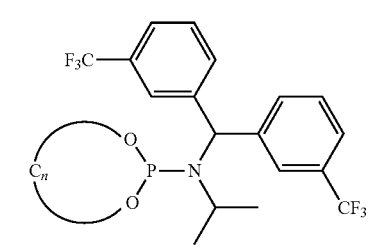
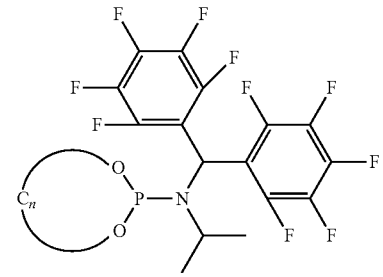
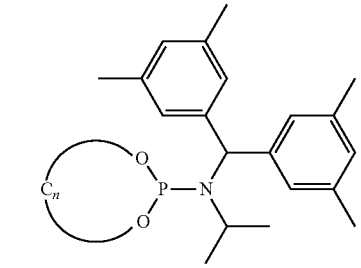
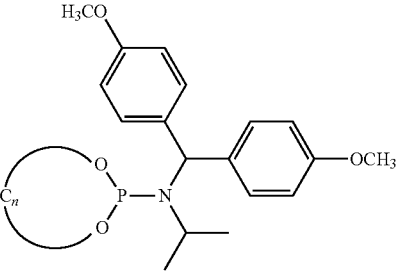
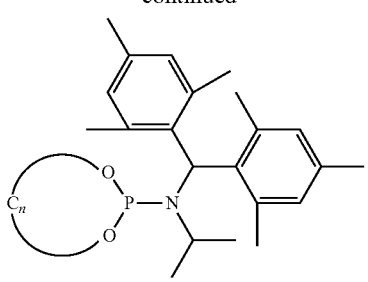
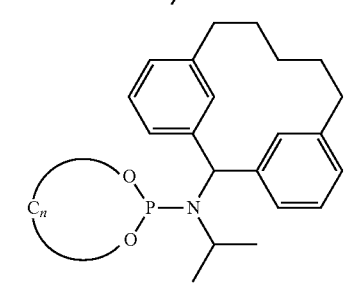
In an embodiment, the moiety —O—$C_n$—O— in each of the above compounds exhibits axial chirality. In an embodiment, the moiety —O—$C_n$—O— is a moiety derived from a binaphthol compound. In a particular embodiment, the binaphthol compound is (R)-1,1'-bi-2-naphthol or (S)-1,1'-bi-2-naphthol.
In another embodiment, the compound of formula (2) is selected from the following compounds:
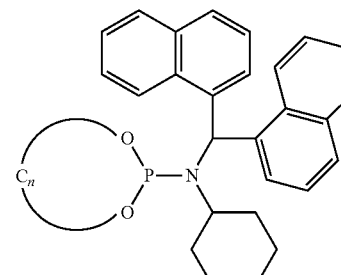
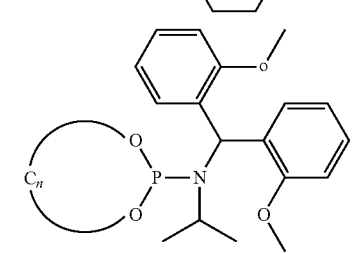
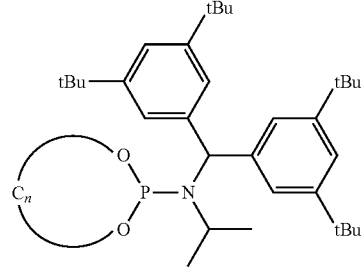

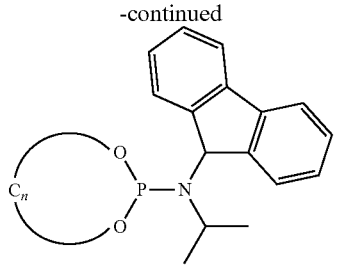

In an embodiment, the moiety —O—C$_n$—O— in each of the above compounds exhibits axial chirality. In an embodiment, the moiety —O—C$_n$—O— is a moiety derived from a binaphthol compound. In a particular embodiment, the binaphthol compound is (R)-1,1'-bi-2-naphthol or (S)-1,1'-bi-2-naphthol.

In a preferred embodiment, the compound is a compound of the formula (C) or (D):

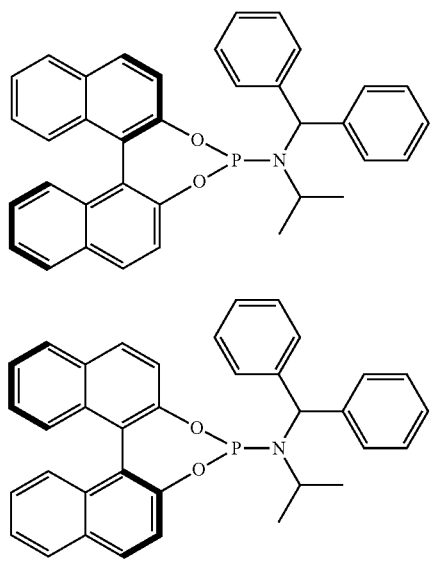

All stereoisomers of the compounds of formula (2) are included within the scope of the present invention. Where a single enantiomer or diastereoisomer is disclosed, the present invention also extends to the other enantiomers or diastereoisomers.

Also provided is a catalytic complex comprising a metal and one or more ligands, wherein said one or more ligands include a compound of the formula (2).

The catalytic complex may contain one or more ligands in addition to the compound of formula (2). For instance, the catalytic complex may contain one or more additional ligands selected from phosphines, bisphosphines, amines, diamines, imines, arsines, sulfides, sulfoxides, carbenes (e.g. N-heterocyclic carbenes), peptides and hybrids thereof, including hybrids of phosphines with amines, hybrids of phosphines with peptides, and hybrids of phosphines with sulfides. In an embodiment, the compound of formula (2) is the only ligand that is present in the complex.

In an embodiment, the metal is a transition metal, e.g. selected from copper, cobalt, iridium, rhodium, ruthenium, nickel, iron, palladium, gold, silver and platinum. In a preferred embodiment, the complex comprises copper. More preferably, the metal is copper (I).

The catalytic complex will typically comprise one or more counterions. In an embodiment, the one or more counterions are selected from triflate, triflimide, tetrafluoroborate ([BF$_4$]$^-$), hexafluorophosphate ([PF$_6$]$^-$), hexafluoroantimonate ([SbF$_6$]$^-$), perchlorate ([ClO$_4$]$^-$) and BARF ([B[3,5-(CF$_3$)$_2$C$_6$H$_3$]$_4$]$^-$). In a preferred embodiment, the catalytic complex contains triflate or triflimide as a counterion.

In an embodiment, the catalytic complex is of the formula M'L'Z', wherein M' is a metal, L' is a ligand which is a compound of the formula (2) and Z' is a counterion. M' and Z' may be as described in any of the embodiments set forth above. In embodiments, M' is copper (I). In an embodiment, Z' is a triflate or triflimide anion.

In an embodiment, the catalytic complex is of one of the following formulae:

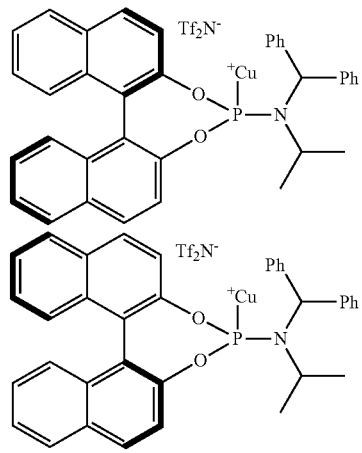

Also provided is a process for producing a compound of formula (2), the process comprising contacting an optionally substituted, aliphatic or aromatic diol of the formula HO—C$_n$—OH with a compound of the formula (3):

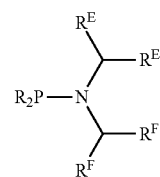

wherein:
each R is independently a leaving group; and
R$^E$ and R$^F$ are as defined above in relation to formula (2).
In an embodiment, each R is independently a halogen. In an embodiment, each R is chlorine.
In an embodiment, the diol is a binaphthol compound, e.g. (R)-1,1'-bi-2-naphthol or (S)-1,1'-bi-2-naphthol. In an embodiment, the moiety —N(CHR$^E$R$^E$)CHR$^F$R$^F$ in formula (3) is N-benzhydrylpropan-2-amino.
Suitable procedures for forming the compound of formula (2) from the compound of formula (3) and said diol are described herein and are known in the art (see e.g. Trost et al, J. Am. Chem. Soc., 2011, 133, 48, 19483-19497).

Suitable procedures for forming the compound of formula (3) are described herein and are known in the art.

In a preferred embodiment, the compound of formula (3) is obtained by contacting a compound of the formula $PR_3$ with a compound of the formula $HN(CHR^ER^E)CHR^FR^F$.

Preferably, the compound of the formula $HN(CHR^ER^E)$ $CHR^FR^F$ is in turn obtained by reductive amination of a compound of the formula $R^FC(O)R^F$ and a compound of the formula $H_2NCHR^ER^E$. Suitable procedures for performing the reductive amination reaction are described herein and are known in the art (see e.g. Davies, S. et al, Org. Biomol. Chem., 2004, 3337-3354; Rahman et al, Org. Biomol. Chem., 2004, 2, 11, 1612-1616; Smith et al, Org. Lett., 2008, 1657-1659; and Mukherjee et al, J. Am. Chem. Soc., 2007, 129, 37, 11336-11337). The compounds $R^FC(O)R^F$ and $H_2NCHR^ER^E$ may be readily available from commercial sources or may be readily synthesised according to literature procedures. In particular, the compound $R^FC(O)R^F$ may be an acyclic or cyclic ketone that is readily available from commercial sources.

By way of illustration, and without limitation, a compound of formula (C) may be obtained by contacting (R)-1,1'-bi-2-naphthol with a compound of the formula $R_2PR'$, wherein each R is independently a leaving group (e.g. chlorine or other halogen) and R' is N-benzhydrylpropan-2-amino. The compound of the formula $R_2PR'$ may be obtained by contacting a compound of the formula $PR_3$ with N-benzhydrylpropan-2-amine. The latter compound may, in turn, be obtained by reductive amination of acetone and diphenylmethanamine. A process for the preparation of the compound of formula (C) is described in the Examples herein.

Advantageously, the compounds of formula (2) can be readily prepared from commercially available starting materials, and their preparation may not require the transformation of a chiral non-racemic amine or the separation of diastereomers during preparation. The compounds may also exhibit desirable stereoselectivity when they are employed in catalytic complexes for use in asymmetric synthesis.

The catalytic complexes of the present invention may be used in processes for the production of chiral compounds in a stereoisomeric excess (e.g. an enantiomeric excess or a diastereomeric excess). In particular, the catalytic complexes may be used in processes for the asymmetric synthesis of chiral compounds, e.g. in processes which involve an asymmetric 1,4-conjugate addition reaction or an asymmetric 1,6-conjugate addition reaction. Examples of such processes are described in PCT Patent Application No. PCT/GB2012/052537, filed 12 Oct. 2012 and entitled "Asymmetric Synthesis of Organic Compounds", the contents of which are incorporated herein by reference in their entirety.

In particular, the present invention provides a process for producing a chiral compound in a stereoisomeric excess, the process comprising:
contacting a first compound comprising an alkene bond with a hydrometallating agent, wherein the first compound and the hydrometallating agent are contacted under conditions such that the first compound is hydrometallated by said hydrometallating agent; and
(ii) contacting the hydrometallated first compound with a second compound, wherein the second compound comprises a conjugated π-bond system which is capable of undergoing a 1,4-conjugate addition reaction or a 1,6-conjugate addition reaction and which has a carbon atom at said 4-position or 6-position respectively, wherein the hydrometallated first compound and the second compound are contacted under conditions such that they undergo an asymmetric 1,4-conjugate addition reaction or an asymmetric 1,6-conjugate addition reaction in which a carbon atom of said hydrometallated first compound binds to the carbon atom at said 4-position or said 6-position of the second compound, forming a stereoisomeric excess of a compound having a chiral carbon atom at said 4-position or said 6-position;
wherein said asymmetric 1,4-conjugate addition reaction or said asymmetric 1,6-conjugate addition reaction is performed in the presence of a catalytic complex of the present invention.

The first compound comprises at least one alkene bond, i.e. at least one aliphatic carbon-carbon double (C=C) bond. The first compound may be an acyclic compound, a cyclic compound, or may comprise an acyclic portion and a cyclic portion. The compound may consist exclusively of carbon and hydrogen atoms, or may comprise one or more other atoms in addition. In an embodiment, the first compound is a straight or branched alkene compound having from 2 to 30 carbon atoms, e.g. from 2 to 20 carbon atoms, e.g. from 2 to 12 carbon atoms, e.g. from 2 to 10 carbon atoms, e.g. 2, 3, 4, 5 or 6 carbon atoms. The alkene compound may be unsubstituted or substituted with one or more substituents, e.g. with 1, 2, 3, 4 or 5 substituents selected from $R^a$; hydrocarbyl optionally substituted with 1, 2, 3, 4 or 5 $R^a$; and $—(CH_2)_j$-heterocyclyl optionally substituted with 1, 2, 3, 4 or 5 $R^a$; wherein $R^a$ and j are as defined elsewhere herein.

Preferably, the first compound is a terminal alkene. Terminal alkenes are typically produced annually on the megaton scale, and are among the most readily available organic molecules. These inexpensive raw materials are feedstocks for the preparation of many classes of organic compounds. Catalytic intermolecular reactions using these alkenes may have a tremendous value-added component because they convert inexpensive raw materials into highly functionalised compounds. Alternatively, the first compound may be an internal alkene; such compounds are also readily available and commonly used in chemistry.

The first compound is reacted with a hydrometallating agent under conditions such that the first compound is hydrometallated. Hydrometallation of the first compound will typically result in the addition of a metal atom to one carbon atom of the alkene bond and a hydride ligand to the other. In certain instances, the first compound may undergo one or more intramolecular rearrangements (e.g. beta hydride elimination followed by further hydrometallation) in which the alkene bond relocates to a different position within the first compound, prior to or during reaction with the hydrometallating agent. Thus, for instance, the hydrometallation reaction may result in the attachment of the metal at the sterically less hindered position of the alkene chain. In this case, hydrometallation may occur either by regiospecific addition of the agent to a terminal alkene bond or by addition of the agent to an internal alkene bond followed by rearrangement via metal hydride elimination and readdition to place the metal at a less hindered position of the alkene chain (see e.g. Schwartz et al, Angew. Chem. Int. Ed., 1976, 6, 333). All such hydrometallation reactions fall within the scope of the present invention.

Various hydrometallating agents are known in the art. The hydrometallating agent may comprise a metal (which term encompasses metalloids) and at least one hydride group. By way of illustration, the hydrometallating agent may comprise at least one metal selected from zirconium, titanium, hafnium, niobium, tantalum, boron, aluminium, tin, silicon, magnesium, zinc, palladium, iridium, copper, rhodium, ruthenium, platinum, rhenium, nickel and the like. Preferably, the hydrometallating agent comprises a transition metal. More preferably, the hydrometallating agent comprises zirconium. The hydrometallating agent may be in the form of a metal complex comprising a metal (e.g. a transition metal) bound to one or more ligands, at least one of which is a hydride ligand.

In a preferred embodiment, the hydrometallating agent is a zirconium complex, e.g. a zirconium halohydride complex. In an embodiment, the hydrometallating agent is a zirconium complex of the formula $HZrR_2X$, wherein each R is independently an optionally substituted 6π electron donating ligand (e.g. having 5 carbon atoms, e.g. a π-cyclopentadienyl ligand) and X is another ligand, e.g. selected from halogen, triflates, alcohols and nitrogen-containing compounds. In a preferred embodiment, the hydrometallating agent is a zirconium complex of the formula $HZrCp_2X$, wherein each Cp is an optionally substituted π-cyclopentadienyl ligand and X is a ligand selected from halogen, triflates, alcohols and nitrogen-containing compounds. Preferably, X is halogen. Particularly preferred is a zirconium complex of the formula $HZrCp_2Cl$, which is commonly known in the art as the "Schwartz reagent" (see Schwartz et al, J. Am. Chem. Soc., 96, 8115-8116, 1974).

The hydrometallating agent may be prepared according to procedures known in the art (see e.g. Org. Syn., coll. Col. 9, p. 162 (1998), vol. 71, p 77 (1993); Negishi, Tet. Lett. 1984, 25, 3407; Buchwald, Tet. Lett. 1987, 28, 3895; Lipshutz, Tet. Lett., 1990, 31, 7257; Negishi, J. Org. Chem. 1991, 56, 2590; and Negishi, Eur. J. Org. Chem. 1999, 969).

The hydrometallated first compound is reacted with a second compound, the second compound comprising a conjugated π-bond system which is capable of undergoing a 1,4-conjugate addition reaction or a 1,6-conjugate addition reaction and which has a carbon atom at the 4- or the 6-position respectively. The second compound may be any compound capable of acting as a so-called "Michael acceptor", and will typically be an electrophilic alkene compound. Exemplary compounds include α,β-unsaturated carbonyl compounds (e.g. enones, acrylate esters, acrylamides, maleimides, alkyl methacrylates, acrylamides and vinyl ketones), cyanoacrylates, vinyl sulfones, nitro ethylenes, vinyl phosphonates, acrylonitriles, vinyl pyridines and azo compounds. In a preferred embodiment, the second compound is an α,β-unsaturated carbonyl compound, e.g. an enone.

In an embodiment, the second compound is a dienone. In an embodiment, the second compound is a steroid compound. In a particular embodiment, the second compound is a steroid compound comprising a dienone group.

In an embodiment, the hydrometallated first compound and the second compound are contacted under conditions such that they undergo an asymmetric 1,4-conjugate addition reaction to form a chiral compound. Thus, a carbon atom of said hydrometallated first compound to which the metal is attached may bind to the carbon atom at said 4-position of the second compound, forming a stereoisomeric excess of a compound having a chiral carbon atom at said 4-position.

Accordingly, in one embodiment, the process comprises:
contacting a first compound comprising an alkene bond with a hydrometallating agent, wherein the first compound and the hydrometallating agent are contacted under conditions such that the first compound is hydrometallated by said hydrometallating agent; and (ii) contacting the hydrometallated first compound with a second compound, wherein the second compound comprises a conjugated π-bond system which is capable of undergoing a 1,4-conjugate addition reaction and which has a carbon atom at said 4-position, wherein the hydrometallated first compound and the second compound are contacted under conditions such that they undergo an asymmetric 1,4-conjugate addition reaction in which a carbon atom of said hydrometallated first compound binds to the carbon atom at said 4-position of the second compound, forming a stereoisomeric excess of a compound having a chiral carbon atom at said 4-position, wherein said asymmetric conjugate addition reaction is performed in the presence of a catalytic complex of the present invention.

In an embodiment, the asymmetric conjugate addition reaction results in the formation of a quaternary centre at the 4-position.

In an embodiment, the second compound is a dienone and the asymmetric conjugate addition reaction results in the formation of a quaternary centre at the 4-position.

In a particular embodiment, the present invention provides a process for producing a chiral compound of the formula (IV) in a stereoisomeric excess (e.g. an enantiomeric or diastereomeric excess):

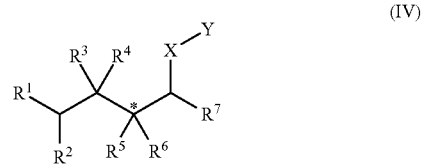

(IV)

wherein
$R^1$, $R^2$, $R^3$ and $R^4$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

or $R^1$ and $R^3$ taken together with the carbon atoms to which they are attached may form a carbocyclic or heterocyclic group, which group is optionally substituted with 1, 2, 3, 4 or 5 $R^a$;

$R^5$, $R^6$ and $R^7$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

or $R^5$ and one of $R^7$ and X, taken together with the carbon atoms to which they are attached, may form a carbocyclic or heterocyclic group, which group is optionally substituted with 1, 2, 3, 4 or 5 $R^a$;

X and Y taken together form an electron withdrawing group in which the bond between X and Y is a π-bond, each $R^a$ is independently selected from halogen, trifluoromethyl, cyano, nitro, oxo, =$NR^b$, —$OR^b$, —$C(O)R^b$, —$C(O)N(R^b)R^c$, —$C(O)OR^b$, —$C(O)SR^b$, —$C(O)SeR^b$, —$OC(O)R^b$, —$S(O)_kR^b$, —$S(O)_kN(R^b)R^c$, —$N(R^b)R^c$, —$N(R^b)N(R^b)R^c$, —$N(R^b)C(O)R^c$ and —$N(R^b)S(O)_kR^b$, $R^b$ and $R^c$ are each independently hydrogen or selected from hydrocarbyl and —$(CH_2)_j$-heterocyclyl, either of which is optionally substituted with 1, 2, 3, 4 or 5 substituents independently selected from halogen, oxo, cyano, amino, hydroxy, alkyl and alkoxy;

j is 0, 1, 2, 3, 4, 5 or 6;
k is 0, 1 or 2; and the asterisk * designates a chiral centre of (R) or (S) configuration.

The compound of formula (IV) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

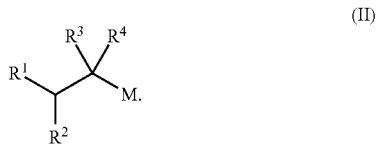

Thus, for instance, the process may comprise contacting an alkene compound of the formula (I):

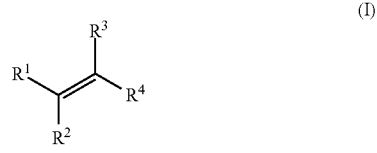

with a hydrometallating agent of the formula HM under conditions such that the compounds react to form the compound of formula (II).

The compound of the formula (II) is then contacted with a compound of the formula (III):

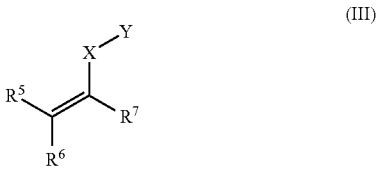

wherein the compound of formula (II) and the compound of formula (III) are contacted under conditions such that they undergo an asymmetric 1,4-conjugate addition reaction in which a stereoisomeric excess of a compound of formula (IV) is formed. The conjugate addition reaction is performed in the presence of a catalytic complex of the present invention.

In embodiments, one or more of the following may apply: (i) $R^1$ is hydrocarbyl optionally substituted with 1, 2, 3, 4 or 5 $R^a$; (ii) $R^1$ is alkyl, cycloalkyl or aralkyl, any of which is optionally substituted with 1, 2, 3, 4 or 5 $R^a$; (iii) $R^3$ is hydrogen or hydrocarbyl optionally substituted with 1, 2, 3, 4 or 5 $R^a$; (iv) $R^3$ is hydrogen or alkyl optionally substituted with 1, 2, 3, 4 or 5 $R^a$; (v) $R^1$ and $R^3$ taken together with the carbon atoms to which they are attached form, in the compounds of formulae (II) and (IV), cycloalkyl optionally substituted with 1, 2, 3, 4 or 5 $R^a$; and (vi) $R^2$ and $R^4$ are each hydrogen.

In an embodiment, M comprises a metal selected from zirconium, titanium, hafnium, niobium, tantalum, boron, aluminium, tin, silicon, magnesium, zinc, palladium, iridium, copper, rhodium, ruthenium, platinum, rhenium and nickel. Preferably, M comprises a transition metal.

More preferably, the compound of formula (II) is obtained by hydrozirconation of the compound comprising said alkene bond, e.g. by hydrozirconation of a compound of the formula (I). Thus, in a preferred embodiment, the hydrometallating agent HM comprises zirconium. Preferably, the hydrometallating agent is a zirconium complex of the formula $HZrR_2X$ as defined above. In a preferred embodiment, the hydrometallating agent is a zirconium complex of the formula $HZrCp_2X$ as defined above. Particularly preferred is a zirconium complex of the formula $HZrCp_2Cl$ (the Schwartz reagent).

In embodiments, one or more of the following may apply: (i) $R^5$ is hydrogen or hydrocarbyl optionally substituted with 1, 2, 3, 4 or 5 $R^a$; (ii) $R^5$ is hydrogen or alkyl optionally substituted with 1, 2, 3, 4 or 5 $R^a$; (iii) $R^6$ is hydrogen or hydrocarbyl optionally substituted with 1, 2, 3, 4 or 5 $R^a$; (iv) $R^6$ is hydrogen or alkyl optionally substituted with 1, 2, 3, 4 or 5 $R^a$; and (v) $R^5$ and $R^7$ taken together with the carbon atoms to which they are attached form cycloalkenyl optionally substituted with 1, 2, 3, 4 or 5 $R^a$.

In an embodiment, $R^5$ and $R^6$ are each other than hydrogen such that the chiral centre is a quaternary centre.

In an embodiment:
X and Y taken together form $-C(O)R^8$, $-C(O)OR^8$, $-C(O)NR^8R^9$, $-CN$, $-C(O)SR^8$, $-C(O)SeR^8$, $-SO_2R^8$, $-SO_2NR^8R^9$ or $-NO_2$, wherein $R^8$ and $R^9$ are each independently hydrogen or selected from hydrocarbyl and $-(CH_2)_j$-heterocyclyl, either of which is optionally substituted with 1, 2, 3, 4 or 5 substituents independently selected from halogen, oxo, cyano, amino, hydroxy, $C_{1-6}$ alkyl and $C_{1-6}$ alkoxy; or
X is carbon and Y is oxo; and X and $R^5$ taken together with the carbon atoms to which they are attached form a carbocyclic group or a heterocyclic group (e.g. a lactone, thiolactone or lactam), either of which is optionally substituted with 1, 2, 3, 4 or 5 $R^a$.

In an embodiment:
X and Y taken together form $-C(O)R^8$ or $-C(O)OR^8$, or
X is carbon and Y is oxo; and X and $R^5$ taken together with the carbon atoms to which they are attached form a carbocyclic group, which is optionally substituted with 1, 2, 3, 4 or 5 $R^a$.

In an embodiment, the compound of formula (III) is an α,β-unsaturated carbonyl compound.

In an embodiment, the compound of formula (III) is an enone. In a particular embodiment, the compound of formula (III) is a cyclic enone, e.g. a cyclohexenone or a cyclopentenone. In an embodiment, the compound of formula (III) is cyclohexen-2-one or cyclopenten-2-one, either of which is optionally substituted with 1, 2, 3, 4 or 5 $R^a$.

In an embodiment, the compound of formula (III) is a dienone. In an embodiment, the compound of formula (III) is a steroid compound. In an embodiment, the compound of formula (III) is a steroid compound comprising a dienone group.

In an embodiment, each $R^a$ is independently selected from acyl, alkoxy, alkoxycarbonyl, alkylamino, alkylsulfinyl, alkylsulfonyl, alkylthio, amino, aminoalkyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy.

The hydrometallated compound undergoes an asymmetric 1,4-conjugate addition reaction with the second compound, forming a chiral compound in a stereoisomeric excess. This reaction occurs in the presence of catalytic complex of the present invention. Thus, for instance, the compound of formula (II) and the compound of formula (III) may be reacted in the presence of a catalytic complex of the present invention, to form a compound of formula (IV) in a stereoisomeric excess. Whilst the first and second compounds will normally be separate compounds, it is envisaged that the processes described herein may also be performed intramolecularly, i.e. using a compound which is capable of being hydrometallated and, moreover, which is capable of undergoing an intramolecular asymmetric 1,4-conjugate addition reaction.

In another embodiment, the present invention provides a process for producing a chiral compound of the formula (IVa) in a stereoisomeric excess:

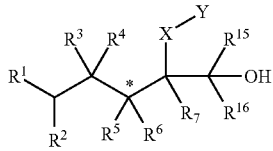

(IVa)

wherein
$R^1, R^2, R^3, R^4, R^5, R^6, R^7$, X and Y are as defined above in relation to formula (IV); and $R^{15}$ and $R^{16}$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

$R^a$ and j are as defined above in relation to formula (IV); and the asterisk * designates a chiral centre of (R) or (S) configuration.

The compound of formula (IVa) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

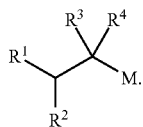

(II)

Thus, for instance, the process may comprise contacting an alkene compound of the formula (I):

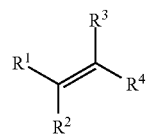

(I)

with a hydrometallating agent of the formula HM under conditions such that the compounds react to form the compound of formula (II).

The compound of the formula (II) is then contacted with a compound of the formula (III):

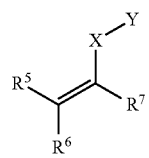

(III)

and a compound of the formula (VII):

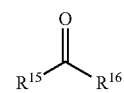

(VII)

wherein the compound of formula (II), the compound of formula (III) and the compound of formula (VII) are contacted under conditions such that they undergo an asymmetric 1,4-conjugate addition reaction to form a stereoisomeric excess of a compound of formula (IVa), wherein said asymmetric conjugate addition reaction is performed in the presence of a catalytic complex of the present invention.

The compound comprising an alkene bond, the compound of formula (III), the hydrometallating agent, the catalytic complex and the non-racemic chiral ligand may be as defined in any of the embodiments described above in relation to processes for the production of compounds of the formula (IV).

In embodiments, $R^7$ is hydrogen. In embodiments, $R^{15}$ is hydrogen and/or $R^{16}$ is hydrocarbyl optionally substituted with 1, 2, 3, 4 or 5 $R^a$, e.g. alkyl or -alkyl-aryl optionally substituted with 1, 2, 3, 4 or 5 $R^a$ In another embodiment, the hydrometallated first compound and the second compound are contacted under conditions such that they undergo an asymmetric 1,6-conjugate addition reaction to form a chiral compound. Thus, a carbon atom of said hydrometallated first compound to which the metal is attached may bind to the carbon atom at said 6-position of the second compound, forming a stereoisomeric excess of a compound having a chiral carbon atom at said 6-position.

Accordingly, in one embodiment, the process comprises:
(i) contacting a first compound comprising an alkene bond with a hydrometallating agent, wherein the first compound and the hydrometallating agent are contacted under conditions such that the first compound is hydrometallated by said hydrometallating agent; and
(ii) contacting the hydrometallated first compound with a second compound, wherein the second compound comprises a conjugated π-bond system which is capable of undergoing a 1,6-conjugate addition reaction and which has a carbon atom at said 6-position, wherein the hydrometallated first compound and the second compound are contacted under conditions such that they undergo an asymmetric 1,6-conjugate addition reaction in which a carbon atom of said hydrometallated first compound binds to the carbon atom at said 6-position of the second compound, forming a stereoisomeric excess of a compound having a chiral carbon atom at said 6-position, wherein said asymmetric conjugate addition reaction is performed in the presence of a catalytic complex of the present invention.

In an embodiment, the asymmetric conjugate addition reaction results in the formation of a quaternary centre at the 6-position.

In a particular embodiment, the present invention provides a process for producing a chiral compound of the formula (VI) in a stereoisomeric excess (e.g. an enantiomeric or diastereomeric excess):

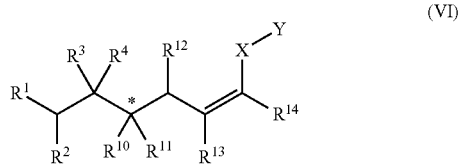

(VI)

wherein
$R^1$, $R^2$, $R^3$ and $R^4$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;
or $R^1$ and $R^3$ taken together with the carbon atoms to which they are attached may form a carbocyclic or heterocyclic group, which group is optionally substituted with 1, 2, 3, 4 or 5 $R^a$;
$R^{10}$, $R^{11}$, $R^{12}$, $R^{13}$ and $R^{14}$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;
or two or more (e.g. two or three) of $R^{10}$, $R^{11}$, $R^{12}$, $R^{13}$, $R^{14}$ and X taken together with the carbon atoms to which they are attached, may form a carbocyclic or heterocyclic group, which group is optionally substituted with 1, 2, 3, 4 or 5 $R^a$,
X and Y taken together form an electron withdrawing group in which the bond between X and Y is a π-bond,
each $R^a$ is independently selected from halogen, trifluoromethyl, cyano, nitro, oxo, =$NR^b$, —$OR^b$, —$C(O)R^b$, —$C(O)N(R^b)R^c$, —$C(O)OR^b$, —$C(O)SR^b$, —$C(O)SeR^b$, —$OC(O)R^b$, —$S(O)_kR^b$, —$S(O)_kN(R^b)R^c$, —$N(R^b)R^c$, —$N(R^b)N(R^b)R^c$, —$N(R^b)C(O)R^c$ and —$N(R^b)S(O)_kR^b$,
$R^b$ and $R^c$ are each independently hydrogen or selected from hydrocarbyl and —$(CH_2)_j$-heterocyclyl, either of which is optionally substituted with 1, 2, 3, 4 or 5 substituents independently selected from halogen, oxo, cyano, amino, hydroxy, alkyl and alkoxy;
j is 0, 1, 2, 3, 4, 5 or 6;
k is 0, 1 or 2; and
the asterisk * designates a chiral centre of (R) or (S) configuration.

The compound of formula (VI) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

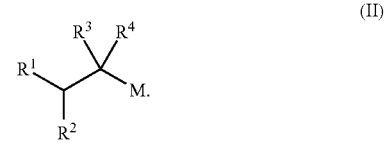

(II)

Thus, for instance, the process may comprise contacting an alkene compound of the formula (I):

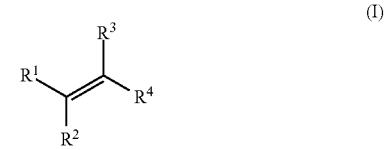

(I)

with a hydrometallating agent of the formula HM under conditions such that the compounds react to form the compound of formula (II).

The compound of the formula (II) is then contacted with a compound of the formula (V):

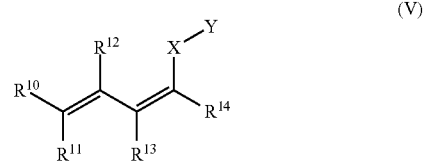

(V)

wherein the compound of formula (II) and the compound of formula (V) are contacted under conditions such that they undergo an asymmetric 1,6-conjugate addition reaction in which a stereoisomeric excess of a compound of formula (VI) is formed. The conjugate addition reaction is performed in the presence of a catalytic complex of the present invention.

In embodiments, one or more of the following may apply: (i) $R^1$ is hydrocarbyl optionally substituted with 1, 2, 3, 4 or 5 $R^a$; (ii) $R^1$ is alkyl, cycloalkyl or aralkyl, any of which is optionally substituted with 1, 2, 3, 4 or 5 $R^a$; (iii) $R^3$ is hydrogen or hydrocarbyl optionally substituted with 1, 2, 3, 4 or 5 $R^a$; (iv) $R^3$ is hydrogen or alkyl optionally substituted with 1, 2, 3, 4 or 5 $R^a$; (v) $R^1$ and $R^3$ taken together with the carbon atoms to which they are attached form, in the compounds of formulae (II) and (IV), cycloalkyl optionally substituted with 1, 2, 3, 4 or 5 $R^a$; and (vi) $R^2$ and $R^4$ are each hydrogen.

In an embodiment, M comprises a metal selected from zirconium, titanium, hafnium, niobium, tantalum, boron, aluminium, tin, silicon, magnesium, zinc, palladium, iridium, copper, rhodium, ruthenium, platinum, rhenium and nickel. Preferably, M comprises a transition metal.

More preferably, the compound of formula (II) is obtained by hydrozirconation of the compound comprising said alkene bond, e.g. by hydrozirconation of a compound of the formula (I). Thus, in a preferred embodiment, the hydrometallating agent HM comprises zirconium. Preferably, the hydrometallating agent is a zirconium complex of the formula $HZrR_2X$ as defined above. In a preferred embodiment, the hydrometallating agent is a zirconium complex of the formula $HZrCp_2X$ as defined above. Particularly preferred is a zirconium complex of the formula $HZrCp_2Cl$ (the Schwartz reagent).

In embodiments, one or more of the following may apply: (i) $R^{10}$ is hydrogen or hydrocarbyl optionally substituted with 1, 2, 3, 4 or 5 $R^a$; (ii) $R^{10}$ is hydrogen or alkyl optionally substituted with 1, 2, 3, 4 or 5 $R^a$; (iii) $R^{11}$ is hydrogen or hydrocarbyl optionally substituted with 1, 2, 3, 4 or 5 $R^a$; (iv) $R^{11}$ is hydrogen or alkyl optionally substituted with 1, 2, 3, 4 or 5 $R^a$; (v) $R^{12}$ is hydrogen or hydrocarbyl optionally substituted with 1, 2, 3, 4 or 5 $R^a$; (vi) $R^{13}$ is hydrogen or alkyl optionally substituted with 1, 2, 3, 4 or 5 $R^a$; (vii) $R^{14}$ is hydrogen or hydrocarbyl optionally substituted with 1, 2, 3, 4 or 5 $R^a$; and (viii) $R^{14}$ is hydrogen or alkyl optionally substituted with 1, 2, 3, 4 or 5 $R^a$.

In an embodiment, X and Y taken together form $—C(O)R^8$, $—C(O)OR^8$, $—C(O)NR^8R^9$, $—CN$, $—C(O)SR^8$, $—C(O)SeR^8$, $—SO_2R^8$, $—SO_2NR^8R^9$ or $—NO_2$, wherein $R^8$ and $R^9$ are each independently hydrogen or selected from hydrocarbyl and $—(CH_2)_j$-heterocyclyl, either of which is optionally substituted with 1, 2, 3, 4 or 5 substituents independently selected from halogen, oxo, cyano, amino, hydroxy, $C_{1-6}$ alkyl and $C_{1-6}$ alkoxy.

In an embodiment, X and Y taken together form $—C(O)R^8$ or $—C(O)OR^8$.

In an embodiment, X is carbon and Y is oxo; and X and one or more (e.g. one or two) of $R^{10}$, $R^{11}$, $R^{12}$, $R^{13}$ and $R^{14}$ taken together with the carbon atoms to which they are attached form a carbocyclic or heterocyclic group, either of which is optionally substituted with 1, 2, 3, 4 or 5 $R^a$. In an embodiment, said carbocyclic or heterocyclic group is a multicyclic group, e.g. comprising 2, 3, 4 or 5 rings. In an embodiment, the compound of formula (V) is a steroid compound.

In an embodiment, each $R^a$ is independently selected from acyl, alkoxy, alkoxycarbonyl, alkylamino, alkylsulfinyl, alkylsulfonyl, alkylthio, amino, aminoalkyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy.

The hydrometallated compound undergoes an asymmetric 1,6-conjugate addition reaction with a second compound, forming a chiral compound in a stereoisomeric excess. This reaction occurs in the presence of a catalytic complex of the present invention. Thus, for instance, the compound of formula (II) and the compound of formula (V) may be reacted in the presence of a catalytic complex of the present invention, to form a compound of formula (VI) in a stereoisomeric excess. Whilst the first and second compounds will normally be separate compounds, it is envisaged that the processes described herein may also be performed intramolecularly, i.e. using a compound which is capable of being hydrometallated and, moreover, which is capable of undergoing an intramolecular asymmetric 1,6-conjugate addition reaction.

Where the stereoselective processes of the present invention involve more than one synthetic step, the processes may be performed in separate reaction vessels or in the same reaction vessel (i.e. as a "one-pot" reaction). A process of the present invention may comprise isolating and/or characterising one or more intermediates, e.g. the hydrometallated alkene, of the process.

The present processes will typically be conducted in the presence of one or more solvents. Examples of suitable solvents include dichloromethane, 1,2-dichloroethane, chloroform, $Et_2O$, t-BuOMe, i-$Pr_2O$, 2,2-dimethoxypropane, tetrahydrofuran, 2-methyltetrahydrofuran, diglyme, 1,4-dioxane, toluene, m-xylene and hexane. In an embodiment, the process is performed in the presence of toluene or t-BuOMe. Particularly when the catalytic complex comprises triflimide as a counterion, it is preferred that the process is performed in the presence of t-BuOMe.

In some instances, it may be necessary to include additional reagents in the reaction to promote reactivity of, for example, the catalytic complex or other components of the reaction, in order to optimise the yield and/or enantioselectivity of the reaction. In particular, it may be advantageous to include one or more additives such as trimethylsilyl chloride (TMSCl).

By way of illustration, a process of the present invention may be conducted in accordance with one of the procedures described in the Examples or elsewhere herein. It will be understood that the processes described in the Examples are solely for the purpose of illustrating the invention and should not be construed as limiting. A process utilising similar or analogous reagents and/or conditions known to one skilled in the art may also be used to obtain a compound of the invention. Any mixtures of final products or intermediates obtained can be separated on the basis of the physicochemical differences of the constituents, in a known manner, into the pure final products or intermediates, for example by chromatography, distillation, fractional crystallisation, or by the formation of a salt if appropriate or possible under the circumstances.

The present processes produce a chiral compound (e.g. the compound of formula (IV), the compound of formula (IVa) or the compound of formula (VI)) in a stereoisomeric excess, i.e. such that the concentration of one stereoisomer of the chiral compound exceeds the concentration of another stereoisomer. That is, the present processes yield a chiral compound with a stereoisomeric excess of greater than zero. Preferably, the present processes yield a product with a stereoisomeric excess of greater than 20%, greater than 50%, greater than 70%, greater than 80%, or greater than 90%. The chiral compound may be enantiomeric or diastereomeric. For instance, the desired compound may be obtained in a substantially pure form (e.g. a form having a purity of greater than 80% purity, in particular greater than 90%, 95% or 99%) of a single enantiomer or diastereomer. In an embodiment, the chiral compound is enantiomeric. All stereoisomers are included within the scope of the present invention. Where a single enantiomer or diastereoisomer is disclosed, the present invention also extends to the other enantiomers or diastereoisomers.

Stereoisomers may be isolated by separation of a racemic or other mixture of the compounds using conventional, e.g.

fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the stereoisomers by conventional means (e.g. HPLC, chromatography over silica).

Compounds of the present invention may also exhibit geometrical isomerism. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

Compounds of the present invention (especially those containing heteroatoms and conjugated bonds) may also exist in tautomeric forms, and all such tautomers are included in the scope of the present invention. In particular, the present compounds (e.g. the compounds of the formula (IV), the compounds of formula (IVa) or the compounds of formula (VI)) may be obtained and isolated in the form of enolates and other tautomeric forms; once again, all such tautomeric forms are included within the scope of the present invention. The present invention also extends to all other variant forms of the defined compounds, for example salts, esters, acids or other variants of the present compounds and their tautomers.

The present processes are particularly relevant to industry. A process of the invention may further comprise formulating a product comprising the chiral compound or converting the chiral compound into a product. In an embodiment, the product is a pharmaceutical product, a cosmetic product, a fragrance, a foodstuff, a petrochemical product or a polymer product.

In particular, the present processes may be utilised in the production of active pharmaceutical ingredients, e.g. prostaglandins. Thus, the chiral compound may be formulated together with one or more pharmaceutically acceptable carriers or excipients, to provide a pharmaceutical formulation; or chemically converted to a pharmaceutically active ingredient. Moreover, where the chiral compound is an active pharmaceutical ingredient, the compound may be obtained in the form of a free acid or base, or in the form of a pharmaceutically acceptable salt thereof. The term "pharmaceutically acceptable salt" refers to acid addition salts or base addition salts of the compounds in the present invention. Pharmaceutically acceptable salts include salts of both inorganic and organic acids.

The following non-limiting Examples illustrate the present invention.

EXAMPLES

Materials and Methods

Materials

Phosphoramidite ligands were synthesised as described below. The phosphoramidite ligands A, B and C used in the experiments of Example 4 have the following structures:

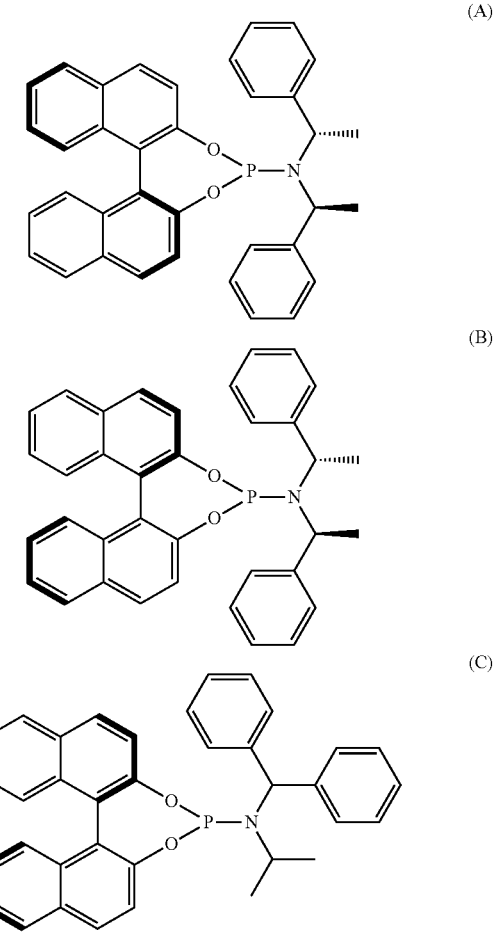

Ligands A and B were commercially available (see also Teichert et al, Angew. Chem. Int. Ed., 2010, 49, 2486-2528). Ligand C was prepared according to the procedures set forth in Examples 1 and 2 below.

Unless stated otherwise, commercially available reagents were purchased from Sigma-Aldrich, Fisher Scientific, Apollo Scientific, Acros Organics, Strem Chemicals, Alfa Aesar or TCI UK and were used without purification. Petroleum ether refers to light petroleum boiling in the range 40-60° C. TMSCl was distilled before use and stored in Schlenk flasks under an argon atmosphere. Deuterated solvents were purchased from Sigma-Aldrich ($CD_2Cl_2$, $CDCl_3$). The Schwartz reagent was prepared according to a literature procedure (see Buchwald et al, Org. Synth., 1993, 71, 77-82) from $Cp_2ZrCl_2$ provided by Strem Chemicals. $(CuOTf)_2.C_6H_6$ was synthesised using a modified literature procedure (see Salomon et al, J. Am. Chem. Soc., 1973, 95(6), 1889-1897) and carefully maintained under an inert atmosphere. $(CuOTf)_2.C_6H_6$ was a white or off-white powder, not green or brown. Certain enone substrates were synthesised according to literature procedures (see Martin et al, J. Am. Chem. Soc., 2006, 128(41), 13368-13369; and Vuagnoux-d'Augustin et al, Chem. Eur. J., 2007, 13(34), 9647-9662).

Dry THF, $CH_2Cl_2$, $Et_2O$, PhMe, benzene, hexane, DME were collected fresh from an mBraun SPS-800 solvent purification system having been passed through anhydrous alumina columns. Dry tert-butyl methyl ether and 2-Me-THF were purchased from Acros with an AcroSeal®. All other dry solvents used were dried over 3 Å molecular sieves and stored under argon. All other solvents were used as purchased from Sigma Aldrich, Rathburn or Fisher Scientific. 1,2-Dichloroethane was distilled before use.

Methods

Procedures using oxygen- and/or moisture-sensitive materials were performed with anhydrous solvents under an atmosphere of anhydrous argon in flame-dried flasks, using standard Schlenk techniques. Analytical thin-layer chromatography was performed on precoated glass-backed plates (Silica Gel 60 $F_{254}$; Merck), and visualised using a combination of UV light (254 nm) and aqueous ceric ammonium molybdate (CAM), aqueous basic potassium permanganate stains or vanillin solution. Flash column chromatography was carried out using Apollo Scientific silica gel 60 (0.040-0.063 nm), Merck 60 Å silica gel, VWR (40-63 µm) silica gel, Sigma Aldrich silica gel. Pressure was applied at the column head via hand bellows or a flow of nitrogen with a solvent system.

Cooling of reaction mixtures to 0° C. was achieved using an ice-water bath. Other temperatures were obtained using a Julabo FT902 immersion cooler.

Unless stated otherwise, solution NMR spectra were recorded at room temperature. $^1$H and $^{13}$C nuclear magnetic resonance experiments were carried out using Bruker DPX-200 (200/50 MHz), AVN-400 (400/100 MHz), DQX-400 (400/100 MHz) or AVC-500 (500/125 MHz) spectrometers. Chemical shifts are reported in ppm from the residual solvent peak. Chemical shifts (δ) are given in ppm and coupling constants (J) are quoted in hertz (Hz). Resonances are described as s (singlet), d (doublet), t (triplet), q (quartet) and m (multiplet). Labels H and H' refer to diastereotopic protons attached to the same carbon and impart no stereochemical information. Assignments were made with the assistance of gCOSY, DEPT-135, gHSQC and gHMBC or gHMQC NMR spectra.

Low-resolution mass spectra were recorded using a Walters LCT premier XE. High resolution mass spectra (EI and ESI) were recorded using a Bruker MicroTOF spectrometer.

Infrared measurements (neat, thin film) were carried out using a Bruker Tensor 27 FT-IR with internal calibration in the range 4000-600 $cm^{-1}$.

Optical rotations were recorded using a Perkin-Elmer 241 Polarimeter.

Solutions were filtered using syringe filters PTFE (0.2 µm, 13 mm diameter) from Camlab.

Racemic products were prepared by adding $Cp_2ZrHCl$ (206 mg, 0.80 mmol, 2.0 eq) to a stirred, room temperature, solution of alkene (1.0 mmol, 2.5 eq) in $CH_2Cl_2$ (2.0 mL) under an argon atmosphere. After stirring for about 40 min, $CuBr.Me_2S$ (82 mg, 0.40 mmol 1.0 eq), was added to the reaction mixture and the resulting black mixture was allowed to stir for an additional 10 min before a cyclic enone (0.40 mmol, 1.0 eq) was added via syringe over about 1 min. Stirring at room temperature was continued arbitrarily for 15 h before the reaction was quenched by the addition of $Et_2O$ (ca 3 mL) and then $NH_4Cl$ (1M aq., ca 1.5 mL). The mixture was partitioned between water and $Et_2O$ and the aqueous phase extracted with $Et_2O$ (3×10 mL). The combined organic phase was washed with $NaHCO_3$ (aq. sat., ca 10 mL), dried ($Na_2SO_4$), filtered and concentrated in vacuo to give an oil. Flash column chromatography of the residue (EtOAc/petrol; $SiO_2$) gave the desired cyclic ketone.

In some instances, enantiomeric excess (ee) was determined by HPLC analysis. Chiral HPLC separations were achieved using an Agilent 1230 Infinity series normal phase HPLC unit and HP Chemstation software. Chiralpak® columns (250×4.6 mm), fitted with matching Chiralpak® Guard Cartridges (10×4 mm), were used as specified in the text. Solvents used were of HPLC grade (Fisher Scientific, Sigma Aldrich or Rathburn); all eluent systems were isocratic.

In other instances, enantiomeric excess was determined by derivatisation of cyclic ketones. Crude material from the 1,4-addition was transferred to a vial with $CDCl_3$ and 3 Å molecular sieves. (+)-(R,R)-1,2-diphenylethylenediamine ((+)-(R,R)-DPEN ca. 2 eq.) was added and the vial was shaken and allowed to stand overnight before the mixture was filtered through a glass pipette containing a small cotton plug and transferred to a NMR tube. $^{13}$C NMR spectroscopy (500 MHz, 1024 scans) and comparison with racemic material was used to determine the enantiomeric excess.

The stereochemical configuration of compound 3b was assigned according to Palais et al (Chem. Eur. J., 2009, 15(40), 10473-10485) and by non-racemic chiral GC analysis using a LIPODEX E (Macherey-Nagels) column. The stereochemical configuration of compound 3c was assigned according to Lee et al (J. Am. Chem. Soc., 2006, 128, 7182). The configuration of compound 3e was assigned according to Palais et al. In the case of compounds 3a, 3d, 3f-3q, 4-6, 7a and 7b, absolute configurations were assigned by analogy to compound 3b.

Deprotection of alcohols was performed by dissolving 24.5 mg (0.06 mmol, 1.0 eq) in THF (1.0 mL) at room temperature and TBAF.3$H_2O$ (1M, solution in THF, 0.12 mL, 0.12 mmol, 2.0 eq) was added and the reaction mixture was stirred until starting material disappearance (TLC control 9:1 Petrol: EtOAc). $Et_2O$ (2 mL) and saturated brine (1 mL) were added. The mixture was partitioned between the aqueous and $Et_2O$ layers and the aqueous phase extracted with $Et_2O$ (3×2 mL). The combined organic phase was dried ($Na_2SO_4$), filtered and concentrated in vacuo. The obtained alcohol was analysed by HPLC analysis.

Example 1

N-Benzhydrylpropan-2-amine

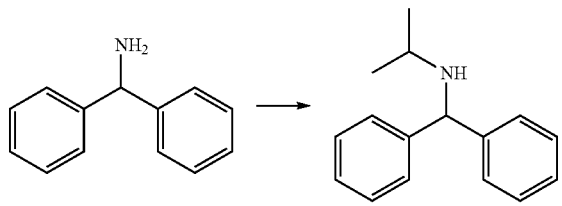 [SMILES: NC(c1ccccc1)c1ccccc1 ; CC(C)NC(c1ccccc1)c1ccccc1]

Acetone (1.9 mL, 2.58 mmol, 2.00 eq) was added to a stirring solution of diphenylmethanamine (2.26 mL, 12.9 mmol, 1 eq) in THF (100 mL) at room temperature. After 5 minutes, $NaB(OAc)_3H$ (4.10 g, 19.4 mmol, 1.5 eq) was added. The resulting suspension was stirred for 48 hours. $Et_2O$ (50 mL) and $NaHCO_3$ (aq. sat., ca. 50 mL) were added to the suspension which was stirred for an extra 15 minutes. The mixture was partitioned between the aqueous and $Et_2O$ layers and the aqueous phase extracted with $Et_2O$ (3×30 mL). The combined organic phase was concentrated in vacuo to one third of its volume (~20 mL). Then HCl (aq 2.0 M, 25 mL) was added dropwise. The mixture was partitioned between the aqueous and $Et_2O$ layers and the organic phase extracted with HCl (aq 2.0 M, 25 mL). Then $CH_2Cl_2$ (20 mL) was added to the combined aqueous phases and NaOH (aq, 25%) was added until the mixture became basic (pH paper, pH ~14). The mixture was partitioned between the aqueous and CH$_2$Cl$_2$ layers and the aqueous phase extracted with CH$_2$Cl$_2$ (3×30 mL). The combined organic phase was dried (MgSO$_4$), filtered and concentrated in vacuo to afford the desired N-benzhydrylpropan-2-amine (1.91 g, 8.45 mmol, 65%). The amine was used without further purification. $^1$H NMR (400 MHz, CDCl$_3$) $\delta_H$/ppm 1.11 (d, J=6.4 Hz, 6 H), 1.37-1.67 (m, 1 H), 2.77 (spt, J=6.3 Hz, 1 H), 5.00 (s, 1 H), 7.22 (br. tt, J=7.3, 1.2 Hz, 2 H), 7.32 (br. t, J=7.6 Hz, 4 H), 7.41 (br. d, J=7.3 Hz, 4 H). $^{13}$C NMR (100 MHz, CDCl$_3$) $\delta_C$/ppm 23.1 (2 C), 42.6, 64.2, 126.8 (2 C), 127.3 (4C), 128.3 (4 C), 144.48 (2C). MS (ESI) m/z [M+H]$^+$: 226.2 (100). IR ($v_{max}$/cm$^{-1}$): 700, 1028, 1167, 1493, 2960.

Example 2

N-Benzhydryl-N-isopropyldinaphtho[2,1-d:1',2'-f][1,3,2]dioxa-phosphepin-4-amine (ligand C)

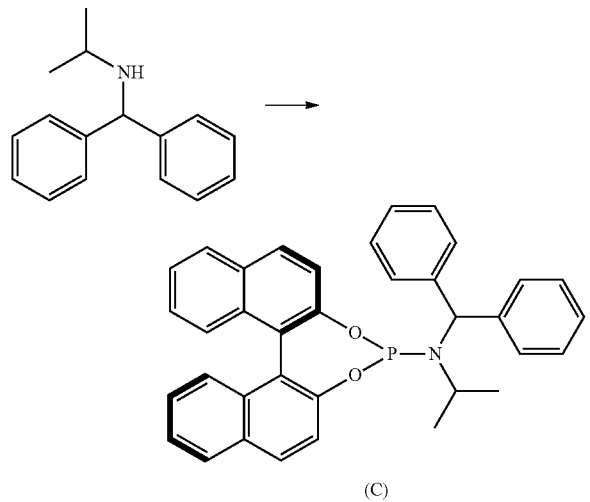

Triethylamine (4.6 mL, 33.3 mmol, 5.00 eq) was added dropwise to an ice-cooled solution of PCl$_3$ (0.58 mL, 6.66 mmol, 1.00 eq) in CH$_2$Cl$_2$ (40 mL). The ice bath was removed and the solution left to warm to room temperature before N-benzhydrylpropan-2-amine (1.5 g, 6.33 mmol, 1.00 eq) was added to the stirring solution. (R)-Binaphthol was added to the suspension after 5 hours and the subsequent mixture was left stirring overnight. The solution was then filtered on a small pad of silica and Celite® and washed with CH$_2$Cl$_2$. After removing the solvent in vacuo, flash column chromatography of the yellow residue (78:17:1: Petrol: CH$_2$Cl$_2$/Et$_3$N; SiO$_2$) gave phosphoramidite ligand C (2.61 g, 4.8 mmol, 73%) as a white solid. $^1$H NMR (500 MHz, CDCl$_3$) $\delta_H$/ppm 1.06 (d, J=6.6 Hz, 3 H), 1.18 (d, J=6.1 Hz, 3 H), 3.68 (dq, J=11.8, 6.1 Hz, 1 H), 5.80 (d, J=17.0 Hz, 1 H), 7.23-7.28 (m, 1 H), 7.28-7.46 (m, 11 H), 7.50 (q, J=7.6 Hz, 4 H), 7.58 (d, J=7.6 Hz, 2 H), 7.86 (d, J=8.8 Hz, 1 H), 7.94 (d, J=7.6 Hz, 2 H), 7.98 (d, J=8.8 Hz, 1 H). $^{13}$C NMR (125 MHz, CDCl$_3$) $\delta_C$/ppm 23.0, 23.2, 46.8, 60.6, 60.8, 121.6, 122.1, 122.3, 124.0, 124.3, 124.6, 125, 125.9, 126.96, 127.00 (3 C), 127.1, 128.1 (3 C), 128.2 (2 C), 128.2, 128.3 (3 C), 128.7 (2 C), 129.0 (2 C), 129.3, 130.1, 130.4, 131.3, 132.7, 143.3, 143.5, 149.1, 150.4. $^{31}$P NMR (200 MHz CDCl$_3$) $\delta_P$/ppm 150.64. HMRS (EI) m/z calcd for C$_{36}$H$_{30}$NO$_2$P [M]$^+$: 539.2014 found: 539.2018. [α]$^{20}_{589}$=−175.88 (c 1.06, CHCl$_3$). IR ($v_{max}$/cm$^{-1}$): 747, 982, 1250, 1590, 3060.

Example 3

Triflimide Complex Containing Ligand C

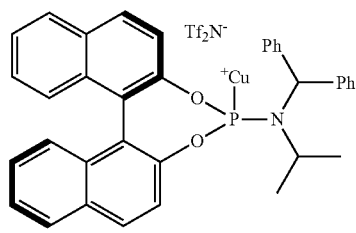

To a flame dried Schlenk flask, at room temperature under an argon atmosphere was added CuCl (46 mg, 0.47 mmol, 1 eq.) and ligand C (253 mg, 0.47 mmol, 1.0 eq.) followed by CH$_2$Cl$_2$ (10 mL). This mixture was stirred for 1 h before AgNTf$_2$ (200 mg, 0.52 mmol, 1.1 eq) was added to the clear solution and stirred for a further 20 min. On the addition of the AgNTf$_2$ the solution turns grey and a precipitate is formed (AgCl). The resulting solution was cannula filtrated into another Schlenk flask. The solvent was then gently removed by use of an oil-pump vacuum (with liquid nitrogen trapping). The resulting off-white solid was dried for at least one extra hour under oil-pump vacuum before storing the catalyst complex under argon. $^1$H NMR (400 MHz, C$_6$D$_6$) $\delta_H$/ppm 7.86 (d, J=8.8 Hz, 1 H), 7.71 (d, J=8.8 Hz, 1 H), 7.52-7.65 (m, 3 H), 7.28-7.45 (m, 9 H), 7.24 (d, J=8.5 Hz, 2 H), 7.17-7.22 (m, 2 H), 7.02-7.12 (m, 2 H), 6.85 (dt, J=23.0, 8.0 Hz, 2 H), 5.38-5.54 (m, 1 H), 3.38-3.53 (m, 1 H), 0.74 (d, J=6.9 Hz, 3 H), 0.60 (d, J=6.6 Hz, 3 H). $^{13}$C NMR (125 MHz, C$_6$D$_6$) $\delta_C$/ppm 148.6 (d, J=12.4 Hz), 147.9 (d, J=4.8 Hz), 141.7 (d, J=6.7 Hz), 141.2 (d, J=8.6 Hz), 132.9, 132.7, 132.6, 132.6, 131.5, 130.6, 130.5, 130.3, 129.2, 129.1, 129.0, 127.3, 127.3 (2C), 127.1, 127.0, 127.0, 126.9, 126.0, 125.9, 123.2, 123.1, 122.1, 122.1, 121.5, 121.4, 120.8 (2C), 120.0 (q, J=323 Hz, 2C), 61.0 (d, J=23.0 Hz), 48.8 (d, J=4.8 Hz), 22.1, 22.0. $^{19}$F NMR (470 MHz, C$_6$D$_6$) $\delta_F$/ppm −76.0 (s, 6F). $^{31}$P NMR (200 MHz, C$_6$D$_6$) $\delta_P$/ppm 121.59 (br. s, 1P). HRMS (EI) m/z calcd for C$_{38}$H$_{30}$CuF$_6$N$_2$O$_6$PS$_2$ [M]$^+$: 882.0483, found: 882.0455. [α]$^{24}_{589}$=−98.79 (c 1.00, CHCl$_3$). IR ($v_{max}$/cm$^{-1}$): 834, 950, 1060, 1133, 1197, 1325.

Example 4

The coupling of 4-phenyl-1-butene and 3-methyl-2-cyclohexen-1-one was evaluated:

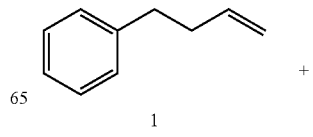

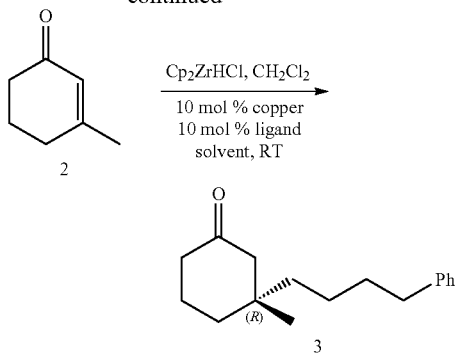

Hydrometallation of 1 with the Schwartz reagent (Cp₂ZrHCl) provided an alkylzirconium species that reacted with 2 in the presence of a phosphoramidite ligand and a copper source to give 3. Various phosphoramidite ligands, sources of copper, additives and solvents were examined. Enantiomeric excess (ee) was determined by HPLC analysis.

The following general procedure was used. Copper source (5.0 mg, 0.01 mmol, 0.05 eq) and the phosphoramidite ligand (10.7 mg, 0.02 mmol, 0.1 eq) were dissolved in the reaction solvent (1.0 mL) under an argon atmosphere and allowed to stir for 1 h at room temperature. In another flask, Cp₂ZrHCl (103.0 mg, 0.40 mmol, 2.0 eq) was added to a stirred, room temperature, solution of 4-phenyl-1-butene (0.08 mL, 0.5 mmol, 2.5 eq) in CH₂Cl₂ (0.20 mL) under an argon atmosphere. After stirring for about 40 min, the resulting clear yellow solution was transferred via syringe over about 1 min to the stirred solution containing the copper and ligand under an argon atmosphere. The resulting dark mixture was allowed to stir for an additional 10 min before 3-methyl-2-cyclohexenone (23 μL, 0.20 mmol, 1.0 eq) was added dropwise via syringe. The reaction was stirred overnight and was quenched by the addition of Et₂O (ca 3 mL) and then NH₄Cl (1 M aq., ca 1.5 mL). The mixture was partitioned between water and Et₂O and the aqueous phase extracted with Et₂O (3×10 mL). The combined organic phase was washed with NaHCO₃ (aq. sat., ca 10 mL), dried (Na₂SO₄), filtered and concentrated in vacuo to give an oil. Flash column chromatography of the residue (EtOAc/petrol; SiO₂) gave the desired cyclic ketone.

The results of this experiment are presented in Table 1. Absolute stereochemical configurations were assigned by analogy to compounds 3b and 3o.

TABLE 1

| Entry | Copper Source | Ligand | Additive | Solvent | R/S | ee (%) |
|---|---|---|---|---|---|---|
| 1 | (CuOTf)₂·PhH | A | TMSCl | Et₂O | S | 60 |
| 2 | (CuOTf)₂·PhH | B | TMSCl | Et₂O | R | 70 |
| 3 | (CuOTf)₂·PhH | C | TMSCl | Et₂O | R | 61 |
| 4 | [Cu(MeCN)₄]·BF₄ | B | TMSCl | Et₂O | R | 23 |
| 5 | CuCl + AgNTf₂ | B | TMSCl | Et₂O | R | 82 |
| 6 | CuCl + AgNTf₂ | B | — | Et₂O | R | 88 |
| 7 | CuCl + AgSbF₆ | B | — | CH₂Cl₂ | R | 73 |
| 8 | CuCl + AgClO₄ | B | — | CH₂Cl₂ | R | 69 |
| 9 | CuCl + AgNTf₂ | B | — | CH₂Cl₂ | R | 78 |
| 10 | CuCl + AgNTf₂ | C | — | CH₂Cl₂ | R | 92 |
| 11 | CuCl + AgNTf₂ | C | — | ClCH₂CH₂Cl | R | 90 |
| 12 | CuCl + AgNTf₂ | C | — | t-BuOMe | R | 94 |
| 13 | CuCl + AgNTf₂ | C | — | 2-Me—THF | R | 90 |

As can be seen from Table 1, hydrometallation of 1 followed by asymmetric conjugate addition to 2 in the presence of phosphoramidite ligand A, (CuOTf)₂.PhH and TMSCl (Table 1, entry 1) gave (S)-3 in 45% yield and 60% ee. The use of diastereomeric ligand B gave (R)-3 and improved the ee to 70% (Table 1, entry 2), while isomeric ligand C gave (R)-3 with 61% ee. Thus, ligand C provided comparable levels of enantioselectivity to isomeric ligands A and B. Using ligand B in combination with different copper sources (Table 1, entries 4, 5, 7 and 8) showed that the reaction was sensitive to the copper counterion and that the triflimide anion provided high levels of enantioselectivity. Using ligand C in combination with copper triflimide (CuNTf₂) gave particularly desirable enantioselectivity in a range of different solvents (Table 1, entries 10-13). The lack of sensitivity of the ligand C—CuNTf₂ system to solvent effects suggested that it was robust.

Example 5

(−)-(R)-3-Methyl-3-(4-phenylbutyl)cyclohexanone (3a)

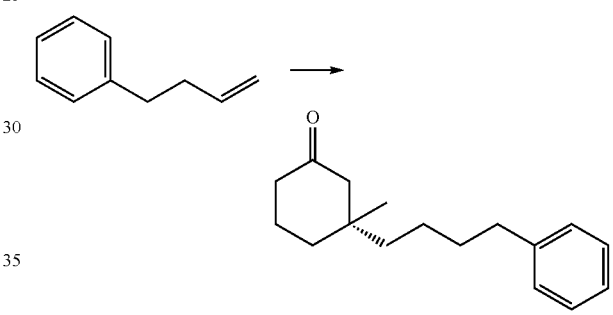

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and the resulting mixture allowed to stir at room temperature. After 1 hour, AgNTf₂ (23.2 mg, 0.060 mmol, 0.15 eq) was added and the suspension was stirred for another 15 min. In another flask, Cp₂ZrHCl (206 mg, 0.80 mmol, 2.0 eq) was added to a stirred, room temperature, solution of 4-phenyl-1-butene (0.15 mL, 1.0 mmol, 2.5 eq) in CH₂Cl₂ (0.40 mL) under an argon atmosphere. After stirring for 15 min, the stirred solution containing the copper and ligand was transferred and filtered using a syringe filter to the clear yellow solution containing the alkene/zirconium mixture. The resulting black mixture was allowed to stir for an additional 10 min before 3-methyl-2-cyclohexenone (45 μL, 0.40 mmol, 1.0 eq) was added dropwise via syringe. Stirring was continued for about 12 h before the reaction was quenched by the addition of Et₂O (ca 3 mL) and then NH₄Cl (1M aq., ca 1.5 mL). The mixture was partitioned between the aqueous and Et₂O layers and the aqueous phase extracted with Et₂O (3×10 mL). The combined organic phase was washed with NaHCO₃ (aq. sat., ca 10 mL), dried (Na₂SO₄), filtered and concentrated in vacuo. Flash column chromatography of the yellow residue (1:9 EtOAc/petrol; SiO₂) gave (−)-(R)-3-Methyl-3-(4-phenylbutyl)cyclohexanone 3a (65 mg, 0.27 mmol, 66%) as a colourless oil. HPLC analysis indicated an enantiomeric excess of 94% [Chiralpak® IC; flow: 1 mL/min; hexane/i-PrOH: 98:2; λ=210 nm; major enantiomer (−)-(R)-3-Methyl-3-(4-phenylbutyl)cyclohexanone, $t_R$=16.8 min; major enantiomer (+)-(S)-3-Methyl-3-(4-phenylbutyl)cyclohexanone, $t_R$=17.9 min]. $^1$H NMR (400 MHz, CDCl$_3$) $\delta_H$/ppm 0.82 (s, 3 H), 1.21 (m, 4 H), 1.39-1.61 (m, 4 H), 1.76 (m, 2 H), 1.97-2.05 (m, 1 H), 2.06-2.13 (m, 1 H), 2.19 (t, J=6.8 Hz, 2 H), 2.53 (br. t, J=6.8, 6.8 Hz, 2 H), 7.04-7.12 (m, 3 H), 7.16-7.23 (m, 2 H). $^{13}$C NMR (100 MHz, CDCl$_3$) $\delta_C$/ppm 22.1, 23.0, 25.0, 32.0, 35.8, 35.8, 38.5, 40.9, 41.4, 53.7, 125.6, 128.2 (2 C), 128.3 (2 C), 142.5, 212.4. HRMS (ESI) m/z calcd for C$_{17}$H$_{24}$NaO [M+Na]$^+$: 267.1719, found: 267.1715. $[\alpha]^{20}_{589}$=−2.8 (c 0.92, CHCl$_3$). IR ($v_{max}$/cm$^{-1}$): 776, 836, 1088, 1252, 1713, 2857, 2932.

Example 6

(+)-(R)-3-Ethyl-3-methylcyclohexanone (3b)

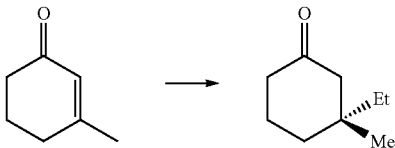

CuCl (3.6 mg, 0.04 mmol, 0.10 eq) and ligand C (21.6 mg, 0.04 mmol, 0.10 eq) were dissolved in $^t$BuOMe (2.0 mL) and stirred at room temperature for 1 h. In another flask Cp$_2$ZrHCl (206 mg, 0.80 mmol, 2.0 eq) was dissolved in CH$_2$Cl$_2$ (1.0 mL) at room temperature, ethylene was then bubbled through the solution for 2 min and the reaction was stirred for 15 min under ethylene atmosphere using a balloon. The solution became clear and yellow. AgNTf$_2$ (17.0 mg, 0.044 mmol, 0.11 eq) was then added to the Cu-ligand mixture and it was stirred for 15 min and filtered via syringe over 1 min to the hydrozirconation reaction flask. The resulting dark mixture was allowed to stir for an additional 10 min before 3-methyl-2-cyclohexenone (45 μL, 0.40 mmol, 1.0 eq) was added dropwise via syringe. Stirring at room temperature was continued 12 h before the reaction was quenched by the addition of Et$_2$O (ca 6 mL) and then NH$_4$Cl (1 M aq., ca 3.0 mL). The mixture was partitioned between water and Et$_2$O and the aqueous phase extracted with Et$_2$O (3×15 mL). The combined organic phase was washed with NaHCO$_3$ (aq. sat., ca 15 mL), dried (Na$_2$SO$_4$), filtered and concentrated in vacuo. Flash column chromatography of the yellow residue (1:9, EtOAc/petrol; SiO$_2$) gave (+)-(R)-3-ethyl-3-methylcyclohexanone 3b (45 mg, 0.32 mmol, 81%) as a colorless oil. Enantiomeric excess (91% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 2.26 (t, 2 H, J=6.6 Hz), 2.16 (d, 1 H, J=13.6 Hz), 2.08 (d, 1H, J=13.6 Hz), 1.88-1.81 (m, 2H), 1.64-1.59 (m, 1H), 1.56-1.51 (m, 1H), 1.33 (q, J=7.3 Hz, 2H), 0.88 (s, 3H), 0.83 (t, 3H, J=7.6 Hz). $^{13}$C NMR (100 MHz, CDCl$_3$) $\delta_C$/ppm 212.8, 53.7, 41.4, 39.0, 35.7, 34.3, 24.7, 22.5, 8.1. MS (ESI) m/z [M+Na]$^+$: 163.1 (100). IR (ATR) v (cm$^{-1}$): 1227, 1764, 2857, 2930. $[\alpha]^{20}_{589}$=+5.53 (c 0.85, CHCl$_3$). The stereochemical configuration of the compound was assigned based on literature (see Palais et al, cited above) and by non-racemic chiral GC analysis using a LIPODEX E (Macherey-Nagels) column. [Major enantiomer (+)-(R)-3-Ethyl-3-methylcyclohexanone, $t_R$=4.30 min; major enantiomer (−)-(S)-3-Ethyl-3-methylcyclohexanone, $t_R$=5.06 min].

Example 7

(+)-(R)-3-Butyl-3-methylcyclohexanone (3c)

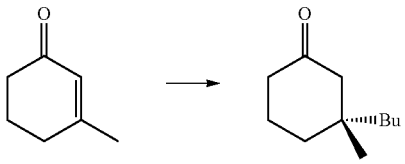

CuCl (3.6 mg, 0.04 mmol, 0.10 eq) and ligand C (21.6 mg, 0.04 mmol, 0.10 eq) were dissolved in $^t$BuOMe (2.0 mL) and stirred at room temperature for 1 h. In another flask Cp$_2$ZrHCl (206 mg, 0.80 mmol, 2.0 eq) was dissolved in CH$_2$Cl$_2$ (1.0 mL) at room temperature, 1-butene was then bubbled through the solution for 2 min and the reaction was stirred for 15 min under 1-butene atmosphere using a balloon. The solution became clear and yellow. AgNTf$_2$ (17.0 mg, 0.044 mmol, 0.11 eq) was then added to the Cu-ligand mixture and it was stirred for 15 min and filtered via syringe over 1 min to the hydrozirconation reaction flask. The resulting dark mixture was allowed to stir for an additional 10 min before 3-methyl-2-cyclohexenone (45 μL, 0.40 mmol, 1.0 eq) was added dropwise via syringe. Stirring at room temperature was continued 12 h before the reaction was quenched by the addition of Et$_2$O (ca 6 mL) and then NH$_4$Cl (1 M aq., ca 3.0 mL). The mixture was partitioned between water and Et$_2$O and the aqueous phase extracted with Et$_2$O (3×15 mL). The combined organic phase was washed with NaHCO$_3$ (aq. sat., ca 15 mL), dried (Na$_2$SO$_4$), filtered and concentrated in vacuo. Flash column chromatography of the yellow residue (1:9 EtOAc/petrol; SiO$_2$) gave (+)-(R)-3-butyl-3-methylcyclohexanone 3c (53 mg, 0.31 mmol, 79%) as a colourless oil. Enantiomeric excess (89% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 2.25 (t, 2 H, J=7.2 Hz), 2.16 (d, 1 H, J=13.6 Hz), 2.07 (d, 1 H, J=13.6 Hz), 1.86-1.80 (m, 2 H), 1.64-1.57 (m, 2 H), 1.29-1.17 (m, 6 H), 0.90 (m, 6 H). $^{13}$C NMR (100 MHz, CDCl$_3$) $\delta_C$/ppm 212.7, 54.0, 41.4, 41.2, 38.7, 36.0, 25.7, 25.3, 23.5, 22.3, 14.2. IR (ATR) v (cm$^{-1}$): 1459, 1714, 2873, 2931, 2957. $[\alpha]^{20}_{589}$=+0.80 (c 1.06, CHCl$_3$). The stereochemical configuration of the compound was assigned according to Lee et al (cited above).

Example 8

(−)-(S)-3-Isopentyl-3-methylcyclohexanone (3d)

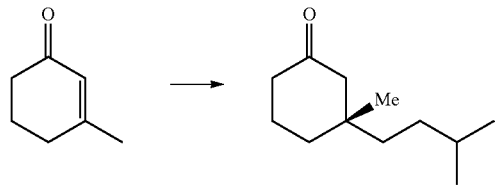

CuCl (3.6 mg, 0.04 mmol, 0.10 eq) and ligand C (21.6 mg, 0.04 mmol, 0.10 eq) were dissolved in $^t$BuOMe (2.0 mL) and stirred at room temperature for 1 h. In another flask Cp$_2$ZrHCl (206 mg, 0.80 mmol, 2.0 eq) was dissolved in CH$_2$Cl$_2$ (1.0 mL) at room temperature, 3-methyl-1-butene was then bubbled through the solution for 2 min and the reaction was stirred for 15 min under 3-methyl-1-butene atmosphere using a balloon. The solution became clear and yellow. AgNTf$_2$ (17.0 mg, 0.044 mmol, 0.11 eq) was then added to the Cu-ligand mixture and it was stirred for 15 min and filtered via syringe over 1 min to the hydrozirconation reaction flask. The resulting dark mixture was allowed to stir for an additional 10 min before 3-methyl-2-cyclohexenone (45 µL, 0.40 mmol, 1.0 eq) was added dropwise via syringe. Stirring at room temperature was continued 12 h before the reaction was quenched by the addition of Et$_2$O (ca 6 mL) and then NH$_4$Cl (1 M aq., ca 3.0 mL). The mixture was partitioned between water and Et$_2$O and the aqueous phase extracted with Et$_2$O (3×15 mL). The combined organic phase was washed with NaHCO$_3$ (aq. sat., ca 15 mL), dried (Na$_2$SO$_4$), filtered and concentrated in vacuo. Flash column chromatography of the yellow residue (1:9 EtOAc/petrol; SiO$_2$) gave (+)-(S)-3-isopentyl-3-methylcyclohexanone 3d (55 mg, 0.30 mmol, 76%) as a colourless oil. Enantiomeric excess (94% ee) was determined by integration of the diastereomeric mixture of the corresponding (+)-(R,R)-DPEN derivative by $^{13}$C NMR spectroscopic analysis. $^1$H NMR (400 MHz, CDCl$_3$) δ$_H$/ppm 2.27 (t, J=6.9 Hz, 2 H), 2.17 (d, 1 H, J=13.5 Hz), 2.08 (d, 1 H, J=13.5 Hz), 1.88-1.83 (m, 2 H), 1.67-1.60 (m, 1 H), 1.55-1.45 (m, 1 H), 1.47-1.41 (m, 1 H), 1.29-1.19 (m, 2 H), 1.17-1.06 (m, 2 H), 0.91 (s, 3H), 0.88 (d, 6H, J=6.7 Hz). $^{13}$C NMR (100 MHz, CDCl$_3$) δ$_C$/ppm 212.8, 54.1, 41.4, 39.5, 38.8, 36.0, 32.6, 28.9, 25.4, 22.9, 22.9, 22.4. MS (ESI) m/z [M+Na]$^+$: 205.2. IR (ATR) v (cm$^{-1}$): 1466, 1713, 2871, 2955. [α]$^{20}_{589}$=−2.51 (c 1.34, CHCl$_3$).

Example 9

(+)-(S)-3-Hexyl-3-methylcyclohexanone (3e)

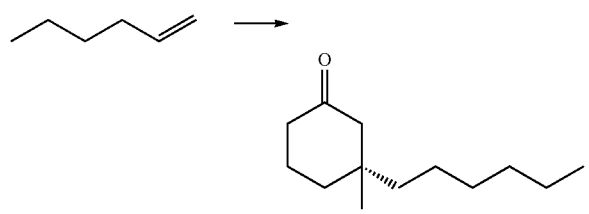

CuCl (2.7 mg, 0.03 mmol, 0.10 eq) and ligand C (15.4 mg, 0.03 mmol, 0.10 eq) were dissolved in $^t$BuOMe (1.5 mL) and stirred at room temperature for 1 h. In another flask Cp$_2$ZrHCl (154 mg, 0.80 mmol, 2.0 eq) was added to a stirred, room temperature, solution of 1-hexene (94 µL, 0.75 mmol, 2.50 eq) in CH$_2$Cl$_2$ (0.40 mL) under an argon atmosphere. After 1 h the solution became clear and yellow. AgNTf$_2$ (12.8 mg, 0.033 mmol, 0.11 eq) was then added to the Cu-ligand mixture and it was stirred for 10 min and filtered via syringe over 1 min to the hydrozirconation reaction flask. The resulting dark mixture was allowed to stir for an additional 10 min before 3-methyl-2-cyclohexenone (33 µL, 0.30 mmol, 1.0 eq) was added dropwise via syringe. Stirring at room temperature was continued for 12 h before the reaction was quenched by the addition of Et$_2$O (ca 4 mL) and then NH$_4$Cl (1 M aq., ca 2 mL). The mixture was partitioned between water and Et$_2$O and the aqueous phase extracted with Et$_2$O (3×12 mL). The combined organic phase was washed with NaHCO$_3$ (aq. sat., ca 12 mL), dried (Na$_2$SO$_4$), filtered and concentrated in vacuo. Flash column chromatography of the yellow residue (1:9 EtOAc/petrol; SiO$_2$) gave (+)-(S)-3-hexyl-3-methylcyclohexanone 3e (38 mg, 0.29 mmol, 95%) as a colourless oil. Enantiomeric excess (96% ee) was determined by integration of the diastereomeric mixture of the corresponding (+)-(R,R)-DPEN derivative by $^{13}$C NMR spectroscopic analysis. $^1$H NMR (400 MHz, CDCl$_3$) δ$_H$/ppm 2.25 (t, J=6.8 Hz, 2H), 2.16 (d, J=13.4 Hz, 1H), 2.08 (d, J=13.4 Hz, 1H), 1.90-1.76 (m, 2H), 1.61 (dt, J=13.1, 6.4 Hz, 1H), 1.56-1.46 (m, 1H), 1.34-1.15 (m, 10H), 0.87 (m, 6H). $^{13}$C NMR (100 MHz, CDCl$_3$) δ$_C$/ppm 212.6, 54.0, 41.7, 41.2, 38.7, 35.9, 31.9, 30.1, 25.2, 23.4, 22.8, 22.3, 14.2. HRMS (ESI) m/z calcd for C$_{13}$H$_{24}$NaO [M+Na]$^+$: 219.1719, found: 219.1715. IR (ATR) v (cm$^{-1}$): 1459, 1712, 2856, 2928. [α]$^{20}_{589}$=−2.42 (c 0.66, CHCl$_3$). The stereochemical configuration of the compound was assigned according to Palais et al, cited above.

Example 10

(−)-(R)-3-(3,3-Dimethylbutyl)-3-methylcyclohexanone (3f)

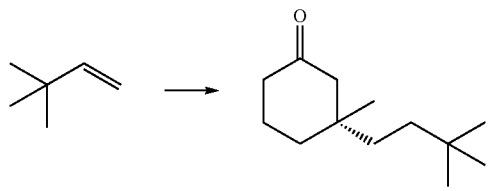

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. AgNTf$_2$ (23.2 mg, 0.060 mmol, 0.15 eq) was added and the suspension was stirred for another 15 min. In another flask, Cp$_2$ZrHCl (206 mg, 0.80 mmol, 2.0 eq) was added to a stirred, room temperature, solution of 3,3-dimethyl-1-butene (0.13 mL, 1.0 mmol, 2.5 eq) in CH$_2$Cl$_2$ (0.80 mL) under an argon atmosphere and heated at 40° C. for 1 h before being cooled to room temperature once the hydrozirconation was complete (clear yellow solution). The stirred solution containing the copper and ligand was transferred and filtered using a syringe filter to the clear yellow solution. The resulting black mixture was allowed to stir for an additional 10 min before 3-methyl-2-cyclohexenone (45 µL, 0.40 mmol, 1.0 eq) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) afforded (−)-(R)-3-(3,3-Dimethylbutyl)-3-methylcyclohexanone 3f (38.9 mg, 0.20 mmol, 50%) as a colourless oil. Enantiomeric excess (86% ee) was determined by integration of the diastereomeric mixture of the corresponding (+)-(R,R)-DPEN derivative by $^{13}$C NMR spectroscopic analysis. $^1$H NMR (400 MHz, CDCl$_3$) δ$_H$/ppm 2.28 (t, J=6.8 Hz, 2 H), 2.06-2.22 (m, 2 H), 1.85 (dt, J=13.0, 6.5 Hz, 2 H), 1.59-1.67 (m, 1 H), 1.48-1.57 (m, 1 H), 1.19 (d, J=3.7 Hz, 2 H), 1.06-1.16 (m, 2 H), 0.90 (s, 3 H), 0.86 (s, 9 H). $^{13}$C NMR (100 MHz, CDCl$_3$) $\delta_C$/ppm 212.5, 54.0, 41.1, 38.3, 37.0, 35.7, 35.6, 30.0, 29.3 (3 C), 25.0, 22.1. HRMS (ESI) m/z calcd for C$_{13}$H$_{24}$NaO [M+Na]$^+$: 219.1719 found: 219.1713. [α]$^{20}_{589}$=−3.43 (c 0.81, CHCl$_3$). IR (ATR) ν (cm$^{-1}$): 1364, 1467, 1713, 2952.

Example 11

(−)-(R)-3-Methyl-3-tetradecylcyclohexanone (3g)

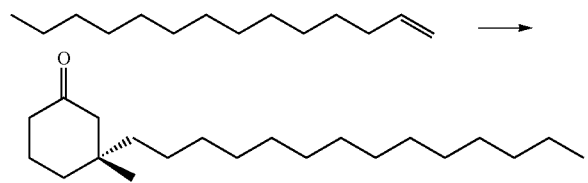

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. AgNTf$_2$ (17.2 mg, 0.060 mmol, 0.11 eq) was added and the suspension was stirred for another 15 min. In another flask, Cp$_2$ZrHCl (206.0 mg, 0.80 mmol, 2.0 eq) was added to a stirred, room temperature, solution of 1-tetradecene (0.25 mL, 1.0 mmol, 2.5 eq) in CH$_2$Cl$_2$ (0.40 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cyclohexenone (45 μL, 0.40 mmol, 1.0 eq) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:19 EtOAc/petrol; SiO$_2$) gave (−)-(R)-3-Methyl-3-tetradecylcyclohexanone 3g (83 mg, 0.27 mmol, 67%) as a colourless oil. Enantiomeric excess (94% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 2.26 (t, J=6.8 Hz, 2 H), 2.18 (d, J=13.8 Hz, 1 H), 2.09 (d, J=13.5 Hz, 1 H), 1.85 (quin, J=6.6 Hz, 2 H), 1.62 (dt, J=13.5, 6.6 Hz, 1 H), 1.52 (dt, J=13.5, 6.6 Hz, 1 H), 1.19-1.31 (m, 26 H), 0.90 (s, 3H), 0.87 (t, J=6.8 Hz, 3 H). $^{13}$C NMR (100 MHz, CDCl$_3$) $\delta_C$/ppm 212.4, 53.8, 41.6, 41.0, 38.6, 35.8, 31.9, 30.3, 29.48-29.79 (br. m, 7 C), 29.3, 25.1, 23.3, 22.7, 22.1, 14.1. HRMS (ESI) m/z calcd for C$_{21}$H$_{40}$NaO [M+Na]$^+$: 331.2971 found: 331.2974. [α]$^{20}_{589}$=−0.74 (c 1.00, CHCl$_3$). IR (ATR) ν (cm$^{-1}$): 776, 1217, 1228, 1367, 1456, 1739, 2852, 2923.

Example 12

(−)-(R)-3-Methyl-3-(4-phenylhexyl)cyclohexanone (3h)

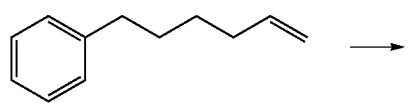

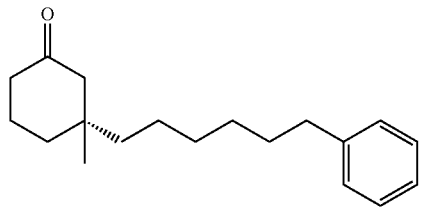

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. AgNTf$_2$ (23.2 mg, 0.060 mmol, 0.15 eq) was added and the suspension was stirred for another 15 min. In another flask, Cp$_2$ZrHCl (206.0 mg, 0.80 mmol, 2.0 eq) was added to a stirred, room temperature, solution of 6-phenyl-1-hexene (0.18 mL, 1.0 mmol, 2.5 eq) in CH$_2$Cl$_2$ (0.40 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cyclohexenone (45 μL, 0.40 mmol, 1.0 eq) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (−)-(R)-3-methyl-3-(4-phenylhexyl)cyclohexanone 3h (70.9 mg, 0.26 mmol, 65%) as a colourless oil. HPLC analysis indicated an enantiomeric excess of 90% [Chiralpak® IC; flow: 1 mL/min; hexane/i-PrOH: 99:1; λ=210 nm; major enantiomer (−)-(R)-3-Methyl-3-(4-phenylhexyl)cyclohexanone t$_R$=19.3 min; minor enantiomer (+)-(S)-3-Methyl-3-(4-phenylhexyl)cyclohexanone, t$_R$=20.4 min]. $^1$H NMR (400 MHz, CDCl$_3$) $\delta_H$/ppm 0.83 (s, 3 H), 1.09-1.32 (m, 9 H), 1.38-1.47 (m, 1 H), 1.48-1.63 (m, 4 H), 1.78 (quin, J=6.5 Hz, 2 H), 1.98-2.04 (m, 1 H), 2.06-2.13 (m, 1 H), 2.19 (t, J=6.5 Hz, 2 H), 2.52 (t, J=7.6 Hz, 2 H), 7.03-7.14 (m, 3 H), 7.16-7.26 (m, 2 H). $^{13}$C NMR (100 MHz, CDCl$_3$) $\delta_C$/ppm 22.1, 23.3, 25.1, 29.3, 30.2, 31.5, 35.8, 36.0, 38.6, 41.0, 41.6, 53.8, 125.6, 128.2 (2 C), 128.4 (2 C), 142.8, 212.5. HRMS (ESI) m/z calcd for C$_{19}$H$_{28}$NaO [M+Na]$^+$: 295.2032 found: 295.2020. [α]$^{20}_{559}$=−11.10 (c 0.91, CHCl$_3$). IR (ν$_{max}$/cm$^{-1}$): 699, 1454, 1495, 1711, 2855, 2929.

Example 13

(−)-(R)-3-(Hex-5-en-1-yl)-3-methylcyclohexanone (3i)

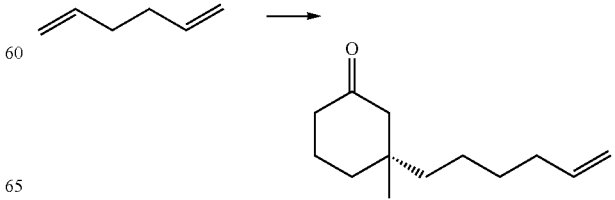

CuCl (1.8 mg, 0.02 mmol, 0.10 eq) and ligand C (10.8 mg, 0.02 mmol, 0.10 eq) were dissolved in $^t$BuOMe (1.0 mL) and stirred at room temperature for 1 h. In another flask Cp$_2$ZrHCl (103 mg, 0.40 mmol, 2.0 eq) was added to a stirred, room temperature, solution of 1,5-hexadiene (238 μL, 2.00 mmol, 10 eq) in CH$_2$Cl$_2$ (0.40 mL) under an argon atmosphere. After 40 min the solution became clear and yellow. AgNTf$_2$ (8.5 mg, 0.022 mmol, 0.11 eq) was then added to the Cu-ligand mixture and it was stirred for 10 min and filtered via syringe over 1 min to the hydrozirconation reaction flask. The resulting dark mixture was allowed to stir for an additional 10 min before 3-methyl-2-cyclohexenone (23 μL, 0.20 mmol, 1.0 eq) was added dropwise via syringe. Stirring at room temperature was continued for 12 h before the reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (−)-(R)-3-(Hex-5-en-1-yl)-3-methylcyclohexanone 3i (29 mg, 0.15 mmol, 75%) as a colourless oil. Enantiomeric excess (78% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 5.79 (ddt, J=16.9, 10.1, 6.7 Hz, 1H), 5.05-4.88 (m, 2H), 2.27 (t, J=7.0 Hz, 2H), 2.31-2.05 (m, 2H), 2.08-1.98 (m, 2H), 1.85 (qd, J=7.1, 5.4 Hz, 2H), 1.69-1.48 (m, 2H), 1.41-1.31 (m, 2H), 1.29-1.22 (m, 4H), 0.91 (s, 3H). $^{13}$C NMR (100 MHz, CDCl$_3$) $\delta_C$/ppm 212.6, 139.0, 114.6, 53.9, 41.6, 41.2, 38.8, 35.9, 33.8, 29.6, 25.3, 22.9, 22.3. HRMS (ESI) m/z calcd for C$_{13}$H$_{22}$NaO [M+Na]$^+$: 217.1563, found: 321.1558. IR (ATR) v (cm$^{-1}$): 1461, 1714, 2855, 2931.

Example 14

(−)-(S)-3-(2-(Cyclohex-3-en-1-yl)ethyl)-3-methylcyclohexanone (3j)

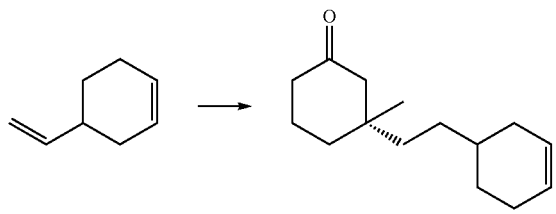

CuCl (1.8 mg, 0.02 mmol, 0.10 eq) and ligand C (10.8 mg, 0.02 mmol, 0.10 eq) were dissolved in $^t$BuOMe (1.0 mL) and stirred at room temperature for 1 h. In another flask Cp$_2$ZrHCl (103 mg, 0.40 mmol, 2.0 eq) was added to a stirred, room temperature, solution of 4-vinyl-1-cyclohexene (65 μL, 0.50 mmol, 2.50 eq) in CH$_2$Cl$_2$ (0.20 mL) under an argon atmosphere. After 40 min the solution became clear and yellow. AgNTf$_2$ (8.5 mg, 0.022 mmol, 0.11 eq) was then added to the Cu-ligand mixture and it was stirred for 10 min and filtered via syringe over 1 min to the hydrozirconation flask. The resulting dark mixture was allowed to stir for an additional 10 min before 3-methyl-2-cyclohexenone (23 μL, 0.20 mmol, 1.0 eq) was added dropwise via syringe. Stirring at room temperature was continued for 12 h before the reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (−)-(S)-3-(2-(cyclohex-3-en-1-yl)ethyl)-3-methylcyclohexanone 3j (21 mg, 0.10 mmol, 48%) as a colourless oil. Enantiomeric excess (86% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 5.74-5.56 (m, 2H), 2.28 (t, J=7.0 Hz, 2H), 2.19 (d, J=13.4 Hz, 1H), 2.12 (d, J=13.4 Hz, 1H), 2.09-1.98 (m, 3H), 1.91-1.81 (m, 2H), 1.77-1.68 (m, 1H), 1.68-1.58 (m, 2H), 1.56-1.49 (m, 1H), 1.49-1.37 (m, 1H), 1.34-1.14 (m, 5H), 0.91 (s, 3H). $^{13}$C NMR (100 MHz, CDCl$_3$) $\delta_C$/ppm 212.5, 127.1, 126.4, 53.9, 41.1, 38.7, 38.5, 35.7, 34.1, 32.0, 30.1, 28.9, 25.2, 25.1, 22.1. HRMS (ESI) m/z calcd for C$_{15}$H$_{24}$NaO [M+Na]$^+$: 243.1719, found: 247.1713. IR (ATR) v (cm$^{-1}$): 1456, 1712, 2920, 3021. [α]$^{20}_{589}$=−3.00 (c 0.83, CHCl$_3$).

Example 15

(−)-(R)-3-(5-Bromopentyl)-3-methylcyclohexanone (3k)

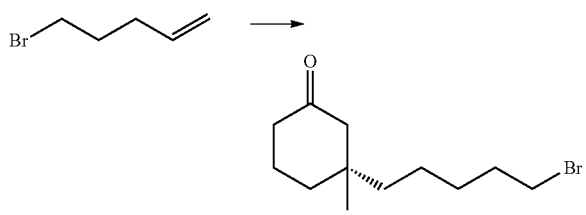

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. AgNTf$_2$ (23.2 mg, 0.060 mmol, 0.15 eq) was added and the suspension was stirred for another 15 mins. In another flask, Cp$_2$ZrHCl (206 mg, 0.80 mmol, 2.0 eq) was added to a stirred, room temperature, solution of 5-bromo-1-pentene (0.12 mL, 1.0 mmol, 2.5 eq) in CH$_2$Cl$_2$ (0.40 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cyclohexenone (45 μL, 0.40 mmol, 1.0 eq) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) (−)-(R)-3-(5-bromopentyl)-3-methylcyclohexanone 3k (55.0 mg, 0.21 mmol, 53%) as a colourless oil. Enantiomeric excess (79% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 3.40 (t, J=6.7 Hz, 2 H), 2.28 (t, J=6.7 Hz, 2 H), 2.14-2.21 (m, 1 H), 2.06-2.13 (m, 1 H), 1.80-1.92 (m, 4 H), 1.58-1.69 (m, 1 H), 1.49-1.58 (m, 1 H), 1.41 (br. s., 2 H), 1.19-1.32 (m, 4 H), 0.92 (s, 3H). $^{13}$C NMR (100 MHz, CDCl$_3$) $\delta_C$/ppm 212.3, 53.7, 41.3, 41.0, 38.6, 35.8, 33.8, 32.7, 28.8, 25.0, 22.6, 22.1. HRMS (ESI) m/z calcd for C$_{12}$H$_{21}$BrNaO [M+Na]$^+$: 283.0668, found: 283.0665. [α]$^{20}_{589}$=−2.06 (c 0.65, CHCl$_3$). IR (ATR) v (cm$^{-1}$): 729, 1227, 1461, 1709, 2934.

Example 16

(−)-(R)-3-(4-(Benzyloxy)butyl)-3-methylcyclohexanone (3l)

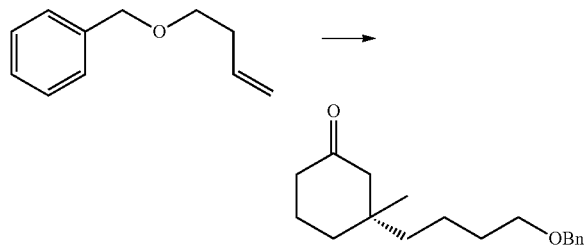

CuCl (1.8 mg, 0.02 mmol, 0.10 eq) and ligand C (10.8 mg, 0.02 mmol, 0.10 eq) were dissolved in $^t$BuOMe (1.0 mL) and stirred at room temperature for 1 h. In another flask Cp$_2$ZrHCl (103 mg, 0.40 mmol, 2.0 eq) was added to a stirred, room temperature, solution of 4-benzyloxy-1-butene (81 mg, 0.50 mmol, 2.50 eq) in CH$_2$Cl$_2$ (0.20 mL) under an argon atmosphere. After 40 min the solution became clear and yellow. AgNTf$_2$ (8.5 mg, 0.022 mmol, 0.11 eq) was then added to the Cu-ligand mixture and it was stirred for 10 min and filtered via syringe over 1 min to the hydrozirconation flask. The resulting dark mixture was allowed to stir for an additional 10 min before 3-methyl-2-cyclohexenone (23 μL, 0.20 mmol, 1.0 eq) was added dropwise via syringe. Stirring at room temperature was continued for 12 h before the reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (−)-(R)-3-(4-(benzyloxy)butyl)-3-methyl-cyclohexanone 3l (29 mg, 0.11 mmol, 53%) as a colourless oil. HPLC analysis indicated an enantiomeric excess of 90% [Chiralpak® IC; flow: 1.0 mL/min; hexane/i-PrOH: 95:5; λ=210 nm; major enantiomer (−)-(R)-3-(4-(benzyloxy)butyl)-3-methyl -cyclohexanone, t$_R$=21.20 min; minor enantiomer (+)-(S)-3-(4-(benzyloxy)-butyl)-3-methyl-cyclohexanone, t$_R$=25.60 min]. $^1$H NMR (400 MHz, CDCl$_3$) $\delta_H$/ppm 7.38-7.14 (m, 5H), 4.42 (s, 2H), 3.39 (t, J=6.4 Hz, 2H), 2.19 (d, J=7.5 Hz, 1H), 2.10 (d, J=13.5 Hz, 1H), 2.03 (d, J=13.6 Hz, 1H), 1.85-1.70 (m, 2H), 1.62-1.39 (m, 4H), 1.34-1.13 (m, 4H), 0.84 (s, 3H). $^{13}$C NMR (100 MHz, CDCl$_3$) $\delta_C$/ppm 212.5, 138.7, 128.5 (2C), 127.8 (2C), 127.6, 73.0, 70.3, 53.9, 41.6, 41.1, 38.7, 35.9, 30.5, 25.1, 22.3, 20.2. HRMS (ESI) m/z calcd for C$_{18}$H$_{26}$NaC$_2$ [M+Na]$^+$: 297.1825, found: 297.1832. IR (ATR) v (cm$^{-1}$): 1103, 1455, 1712, 2853, 2936. [α]$^{20}_{589}$=−2.76 (c 1.27, CHCl$_3$).

Example 17

(+)-(R)-3-(4-((tert-Butyldimethylsilyl)oxy)butyl)-3-methylcyclohexanone (3m)

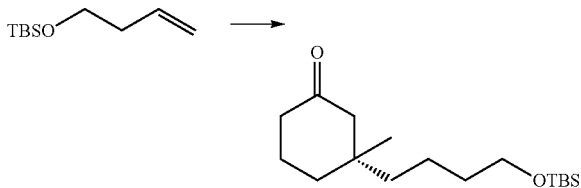

CuCl (1.8 mg, 0.02 mmol, 0.10 eq) and ligand C (10.8 mg, 0.02 mmol, 0.10 eq) were dissolved in $^t$BuOMe (1.0 mL) and stirred at room temperature for 1 h. In another flask Cp$_2$ZrHCl (103 mg, 0.40 mmol, 2.0 eq) was added to a stirred, room temperature, solution of 4-[(tert-butyldimethylsilyl)oxy]-1-butene (93 mg, 0.50 mmol, 2.5 eq) in CH$_2$Cl$_2$ (0.20 mL) under an argon atmosphere. After 20 min the solution became clear and yellow. AgNTf$_2$ (8.5 mg, 0.022 mmol, 0.11 eq) was then added to the Cu-ligand mixture and it was stirred for 15 min and filtered via syringe over 1 min to the hydrozirconation reaction flask. The resulting dark mixture was allowed to stir for an additional 10 min before 3-methyl-2-cyclohexenone (23 μL, 0.20 mmol, 1.0 eq) was added dropwise via syringe. Stirring at room temperature was continued 12 h before the reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (+)-(R)-3-(4-((tert-butyldimethylsilyl)oxy)butyl)-3-methylcyclohexanone 3m (44 mg, 0.15 mmol, 75%) as a colourless oil. Enantiomeric excess (92% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 3.61 (t, J=6.4 Hz, 2H), 2.27 (t, J=6.8 Hz, 2H), 2.21-2.06 (m, 2H), 1.91-1.80 (m, 2H), 1.66-1.60 (m, 1H), 1.57-1.44 (m, 3H), 1.33-1.22 (m, 4H), 0.91 (s, 3H), 0.89 (s, 9H), 0.04 (s, 6H). $^{13}$C NMR (100 MHz, CDCl$_3$) $\delta_C$/ppm 212.6, 63.1, 54.0, 41.6, 41.2, 38.8, 35.9, 33.6, 26.1 (3C), 25.1, 22.3, 19.8, 18.5, −5.1 (2C). HRMS (ESI) m/z calcd for C$_{17}$H$_{34}$NaC$_2$Si [M+Na]$^+$: 321.2220, found: 321.2219. IR (ATR) v (cm$^{-1}$): 1463, 1715, 2857, 2934. [α]$^{20}_{589}$=+0.23 (c 1.27, CHCl$_3$).

Example 18

(−)-(R)-3-(4-((tert-Butyldiphenylsilyl)oxy)butyl)-3-methylcyclohexanone (3n)

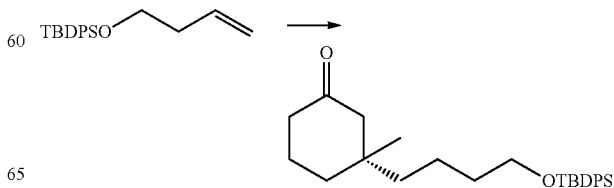

CuCl (3.6 mg, 0.04 mmol, 0.10 eq) and ligand C (21.6 mg, 0.04 mmol, 0.10 eq) were dissolved in ᵗBuOMe (2.0 mL) and stirred at room temperature for 1 h. In another flask Cp₂ZrHCl (206 mg, 0.80 mmol, 2.0 eq) was added to a stirred, room temperature, solution of 4-(tert-butyldiphenyl-silyl)oxy)-1-butene (310 mg, 1.00 mmol, 2.50 eq) in $CH_2Cl_2$ (0.20 mL) under an argon atmosphere. After 40 min the solution became clear and yellow. $AgNTf_2$ (17.0 mg, 0.044 mmol, 0.11 eq) was then added to the Cu-ligand mixture and it was stirred for 10 min and filtered via syringe over 1 min to the hydrozirconation flask. The resulting dark mixture was allowed to stir for an additional 10 min before 3-methyl-2-cyclohexenone (45 μL, 0.40 mmol, 1.0 eq) was added dropwise via syringe. Stirring at room temperature was continued for 12 h before the reaction was quenched by the addition of $Et_2O$ (ca 6 mL) and then $NH_4Cl$ (1 M aq., ca 3 mL). The mixture was partitioned between water and $Et_2O$ and the aqueous phase extracted with $Et_2O$ (3×15 mL). The combined organic phase was washed with $NaHCO_3$ (aq. sat., ca 15 mL), dried ($Na_2SO_4$), filtered and concentrated in vacuo. Flash column chromatography of the yellow residue (1:9 EtOAc/petrol; $SiO_2$) gave (−)-(R)-3-(4-((tert-butyldiphenylsilyl)oxy)butyl)-3-methylcyclohexanone 3n (51 mg, 0.24 mmol, 61%) as a colourless oil. HPLC analysis indicated an enantiomeric excess of 90% [Chiralpak® AY-H; flow: 0.7 mL/min; hexane/i-PrOH: 99:1; λ=210 nm; major enantiomer (−)-(R)-3-(4-((tert-butyldiphenylsilyl)oxy)butyl)-3-methyl-cyclohexanone, $t_R$=10.32 min; minor enantiomer (+)-(S)-3-(4-((tert-butyldiphenylsilyl)oxy)butyl)-3-methylcyclohexanone, $t_R$=11.08 min]. ¹H NMR (400 MHz, $CDCl_3$) $δ_H$/ppm 7.65-7.51 (m, 4H), 7.41-7.23 (m, 6H), 3.59 (t, J=6.3 Hz, 2H), 2.18 (d, J=6.1 Hz, 2H), 2.08 (d, J=13.5 Hz, 1H), 2.01 (dt, J=13.5, 1.3 Hz, 1H), 1.81-1.72 (m, 2H), 1.57-1.47 (m, 1H), 1.47-1.38 (m, 3H), 1.29-1.10 (m, 4H), 0.97 (s, 9H), 0.82 (s, 3H). ¹³C NMR (100 MHz, $CDCl_3$) $δ_C$/ppm 212.5, 135.7 (4C), 134.2 (2C), 129.7 (2C), 127.7 (4C), 63.8, 54.0, 41.6, 41.2, 38.7, 35.8, 33.3, 27.0 (3C), 25.1, 22.3, 19.7, 19.2. HRMS (ESI) m/z calcd for $C_{27}H_{38}NaC_2Si$ [M+Na]⁺: 445.2533, found: 445.2518. IR (ATR) v (cm⁻¹): 1110, 1472, 1713, 2857, 2932. $[α]^{20}_{589}$=−0.84 (c 1.45, $CHCl_3$).

Example 19

(−)-(R)-3-(4-((tert-Butyldimethylsilyl)oxy)-4-methylpentyl)-3-methylcyclo-hexanone (3o)

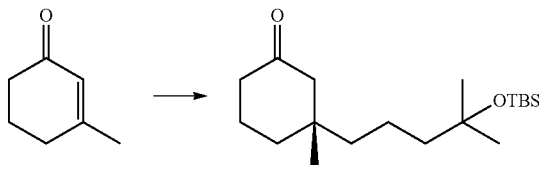

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. $AgNTf_2$ (23.2 mg, 0.060 mmol, 0.15 eq) was added and the suspension was stirred for another 15 min. In another flask, Cp₂ZrHCl (206.0 mg, 0.80 mmol, 2.0 eq) was added to a stirred, room temperature, solution of 4-tert-butyldimethylsililoxy-4-methyl-1-pentene (214 mg, 1.0 mmol, 2.5 eq) in $CH_2Cl_2$ (0.40 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cyclohexenone (45 μL, 0.40 mmol, 1.0 eq) was added dropwise via syringe. Stirring continued 12 h before the reaction was quenched by the addition of $Et_2O$ (ca 3 mL) and then $NH_4Cl$ (1M aq., ca 1.5 mL). The mixture was partitioned between the aqueous and $Et_2O$ layers and the aqueous phase extracted with $Et_2O$ (3×10 mL). The combined organic phase was washed with $NaHCO_3$ (aq. sat., ca 10 mL), dried ($Na_2SO_4$), filtered and concentrated in vacuo. Flash column chromatography of the yellow residue (1:9 EtOAc/petrol; $SiO_2$) gave (−)-(R)-3-(4-((tert-butyldimethylsilyl)oxy)-4-methylpentyl)-3-methylcyclohexanone 3o (108 mg, 0.33 mmol, 83%) as a colourless oil. Enantiomeric excess (89% ee) was determined by integration of the diastereomeric mixture of the corresponding (+)-(R,R)-DPEN derivative by ¹³C NMR spectroscopic analysis. ¹H NMR (400 MHz, $CDCl_3$) $δ_H$/ppm 2.25 (t, J=7.2 Hz, 2H), 2.16 (d, 1H, J=13.6 Hz), 2.08 (d, 1H, J=13.6 Hz), 1.87-1.80 (m, 2H), 1.65-1.58 (m, 1H), 1.55-1.48 (m, 1H), 1.32-1.29 (m, 4H), 1.23-1.18 (m, 2H), 1.15 (s, 6H), 0.90 (s, 3H), 0.82 (s, 9H), 0.03 (s, 6H). ¹³C NMR (100 MHz, $CDCl_3$) $δ_C$/ppm 212.7, 73.6, 54.2, 45.8, 42.5, 41.3, 38.9, 36.0, 30.2, 29.9, 26.0 (3C), 25.2, 22.4, 18.3, 18.2, −1.90 (2C). MS (ESI) m/z calcd for $C_{19}H_{38}NaC_2Si$ [M+Na]⁺: 349.2533, found: 349.2533. IR (ATR) v (cm⁻¹): 1462, 1714, 2855, 2954. $[α]^{20}_{589}$=−0.78 (c 1.56, $CHCl_3$).

Example 20

(+)-(S)-3-Methyl-3-(3-(trimethylsilyl)propyl)cyclohexanone (3p)

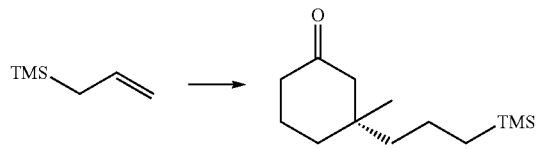

CuCl (3.6 mg, 0.04 mmol, 0.10 eq) and ligand C (21.6 mg, 0.04 mmol, 0.10 eq) were dissolved in ᵗBuOMe (2.0 mL) and stirred at room temperature for 1 h. In another flask Cp₂ZrHCl (206 mg, 0.80 mmol, 2.0 eq) was added to a stirred, room temperature, solution of 1-trimethylsilyl-1-propene (80 μL, 0.50 mmol, 2.50 eq) in $CH_2Cl_2$ (0.40 mL) under an argon atmosphere. After 40 min the solution became clear and yellow. $AgNTf_2$ (17.0 mg, 0.044 mmol, 0.11 eq) was then added to the Cu-ligand mixture and it was stirred for 10 min and filtered via syringe over 1 min to the hydrozirconation reaction flask. The resulting dark mixture was allowed to stir for an additional 10 min before 3-methyl-2-cyclohexenone (45 μL, 0.40 mmol, 1.0 eq) was added dropwise via syringe. Stirring at room temperature was continued for 12 h before the reaction was quenched by the addition of $Et_2O$ (ca 6 mL) and then $NH_4Cl$ (1 M aq., ca 3 mL). The mixture was partitioned between water and $Et_2O$ and the aqueous phase extracted with $Et_2O$ (3×15 mL). The combined organic phase was washed with $NaHCO_3$ (aq. sat., ca 15 mL), dried ($Na_2SO_4$), filtered and concentrated in vacuo. Flash column chromatography of the yellow residue (1:9 EtOAc/petrol; $SiO_2$) gave (+)-(S)-3-methyl-3-(3-(trimethylsilyl)propyl)cyclohexanone 3p (37 mg, 0.33 mmol, 82%) as a colourless oil. Enantiomeric excess (97% ee) was determined by integration of the diastereomeric mixture of the corresponding (+)-(R,R)-DPEN derivative by $^{13}$C NMR spectroscopic analysis. $^1$H NMR (400 MHz, CDCl$_3$) $\delta_H$/ppm 2.27 (t, J=6.9 Hz, 2H), 2.18 (d, J=13.4 Hz, 1H), 2.09 (d, J=13.5 Hz, 1H), 1.91-1.79 (m, 2H), 1.68-1.58 (m, 1H), 1.58-1.47 (m, 1H), 1.34-1.18 (m, 4H), 0.90 (s, 3H), 0.50-0.39 (m, 2H), −0.03 (s, 9H). $^{13}$C NMR (100 MHz, CDCl$_3$) $\delta_C$/ppm 212.6, 54.0, 46.2, 41.2, 39.0, 36.0, 25.1, 22.3, 17.8, 17.5, −1.4 (3C). HRMS (ESI) m/z calcd for C$_{13}$H$_{26}$NaOSi [M+Na]$^+$: 249.1645, found: 249.1645. IR (ATR) v (cm$^{-1}$): 1247, 1458, 1714, 2926, 2928. [α]$^{20}_{589}$=+0.21 (c 1.43, CHCl$_3$).

Example 21

(+)-(3R)-3-(4-((tert-Butyldimethylsilyl)oxy)-4-(4-chlorophenyl)butyl)-3-methylcyclohexanone (3q)

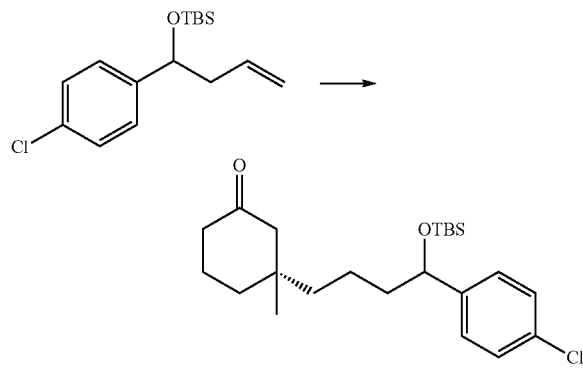

CuCl (3.6 mg, 0.04 mmol, 0.10 eq) and ligand C (21.6 mg, 0.040 mmol, 0.10 eq) were dissolved in t-BuOMe (2.0 mL) under an argon atmosphere and allowed to stir for 1 h at room temperature. AgNTf$_2$ (23.2 mg, 0.060 mmol, 0.15 eq) was added and the suspension was stirred for another 15 min. In another flask, Cp$_2$ZrHCl (206 mg, 0.80 mmol, 2.0 eq) was added to a stirred, room temperature, solution of tert-butyl((1-(4-chlorophenyl)but-3-en-1-yl)oxy)dimethylsilane (0.30 mL, 1.0 mmol, 2.5 eq) in CH$_2$Cl$_2$ (0.40 mL) under an argon atmosphere. The stirred solution containing the copper and ligand was transferred and filtered using a syringe filter to the clear yellow hydrozirconation solution. The resulting black mixture was allowed to stir for an additional 10 min before 3-methyl-2-cyclohexenone (45 μL, 0.40 mmol, 1.0 eq) was added dropwise via syringe. Stirring continued 12 h before the reaction was quenched by the addition of Et$_2$O (ca 3 mL) and then NH$_4$Cl (1 M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) (+)-(3R)-3-(4-((tert-Butyldimethylsilyl)oxy)-4-(4-chlorophenyl)butyl)-3-methylcyclohexanone 3q (133.9 mg, 0.32 mmol, 82%) as a colourless oil. HPLC analysis of the alcohol derivative indicated a ~1:1 diastereomeric ratio and an enantiomeric excess of 89% [Chiralpak® IC; flow: 1.0 mL/min; hexane/i-PrOH: 88:12; λ=210 nm; major enantiomer (+)-(3R)-3-(4-((tert-Butyldimethylsilyl)oxy)-4-(4-chlorophenyl)butyl)-3-methylcyclohexanone, t$_R$=16.7 min & 20.9 min; minor enantiomer (−)-(3S)-3-(4-((tert-Butyldimethylsilyl)oxy)-4-(4-chlorophenyl)-butyl)-3-methylcyclohexanone, t$_R$=19.5 min & 22.5 min]. $^1$H NMR (400 MHz, CDCl$_3$) $\delta_H$/ppm 7.22-7.27 (m, 2 H), 7.15-7.21 (m, 2 H), 4.58 (ddd, J=7.4, 4.6, 2.7 Hz, 1 H), 2.20-2.28 (m, 2 H), 2.03-2.16 (m, 2 H), 1.75-1.88 (m, 2 H), 1.44-1.67 (m, 4 H), 1.12-1.37 (m, 4 H), 0.86 (s, 3 H), 0.86 (s, 9 H), 0.00 (s, 3 H), −0.17 (d, J=1.2 Hz, 3 H). $^{13}$C NMR (100 MHz, CDCl$_3$) $\delta_C$/ppm 212.2, 144.2, 132.3, 128.2 (2 C), 127.1 (2 C), 74.2, 53.7, 41.7, 41.4, 41.0, 38.6, 35.8, 25.8 (3C), 24.8, 22.1, 19.4, 18.1, −4.6, −5.0. HRMS (ESI) m/z calcd for C$_{23}$H$_{37}$ClNaC$_2$Si [M+Na]$^+$: 431.2144 found: 431.2144. [α]$^{20}_{589}$=+0.51 (c 1.22, CHCl$_3$). IR (ATR) v (cm$^{-1}$): 776, 836, 1088, 1252, 1713, 2857, 2932.

Example 22

(−)-(R)-3-Methyl-3-(4-phenylbutyl)cyclopentanone (4)

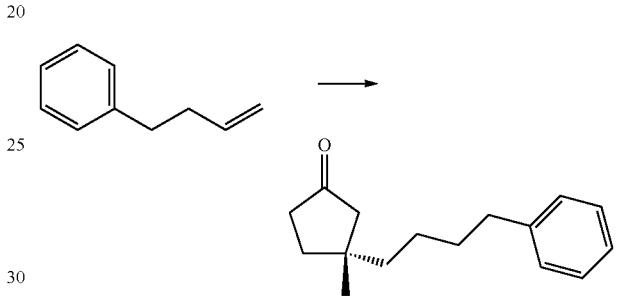

CuCl (1.8 mg, 0.02 mmol, 0.10 eq) and ligand C (18.8 mg, 0.020 mmol, 0.10 eq) were dissolved in t-BuOMe (1.0 mL) under an argon atmosphere and allowed to stir for 1 h at room temperature. AgNTf$_2$ (8.5 mg, 0.022 mmol, 0.11 eq) was added and the suspension was stirred for another 15 min. In another flask, Cp$_2$ZrHCl (309.0 mg, 1.60 mmol, 3.0 eq) was added to a stirred, room temperature, solution of hex-4-en-1-ylbenzene (0.3 mL, 2.0 mmol, 5.0 eq) in CH$_2$Cl$_2$ (0.80 mL) under an argon atmosphere. After stirring for 15 min, the stirred solution containing the copper and ligand was transferred and filtered using a syringe filter to the clear yellow solution. The resulting black mixture was cooled with an ice bath allowed to stir for an additional 20 min before 3-methyl-2-cyclopentanone (20 μL, 0.20 mmol, 1.0 eq) was added dropwise via syringe. Stirring continued 12 h leaving the ice melts so the reaction mixture slowly warmed up. The reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (−)-(R)-3-Methyl-3-(4-phenylbutyl)cyclopentanone 4 (25.8 mg, 0.11 mmol, 56%) as a colourless oil. HPLC analysis indicated an enantiomeric excess of 65% [Chiralpak® AY-H; flow: 1 mL/min; hexane/i-PrOH: 95:5; λ=210 nm; major enantiomer (+)-(R)-3-methyl-3-(4-phenylhexyl)cyclopentanone, t$_R$=9.50 min; minor enantiomer (−)-(S)-3-methyl-3-(4-phenylhexyl)cyclopentanone, t$_R$=8.60 min]. $^1$H NMR (500 MHz, CDCl$_3$) $\delta_H$/ppm 7.25-7.33 (m, 2 H), 7.13-7.22 (m, 3 H), 2.64 (t, J=7.6 Hz, 2 H), 2.26-2.32 (m, 2 H), 2.05-2.12 (m, 1 H), 1.98-2.05 (m, 1 H), 1.73-1.85 (m, 2 H), 1.64 (dt, J=15.1, 7.4 Hz, 2 H), 1.26-1.47 (m, 4 H), 1.05 (s, 3 H). $^{13}$C NMR (125

MHz, CDCl$_3$) δ$_C$/ppm 24.4, 25.0, 32.1, 35.2, 35.8, 36.8, 39.5, 41.6, 52.2, 125.7, 128.28 (2 C), 128.32 (2 C), 142.5, 220.2. HRMS (ESI) m/z calcd for C$_{16}$H$_{22}$NaO [M+Na]$^+$: 253.1563 found: 253.1562. [α]$^{20}_{589}$=+22.64 (c 0.53, CHCl$_3$). IR (ATR) v (cm$^{-1}$): 699, 1454, 1496, 1711, 2930.

Example 23

(+)-(R)-3-Ethyl-3-(4-phenylbutyl)cyclohexanone (5)

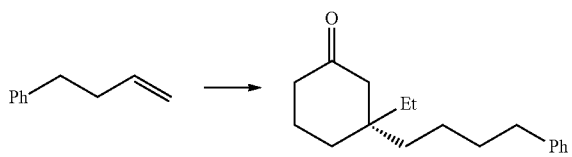

CuCl (1.8 mg, 0.02 mmol, 0.10 eq) and ligand C (10.8 mg, 0.02 mmol, 0.10 eq) were dissolved in $^t$BuOMe (1 mL) and stirred at room temperature for 1 h. In another flask Cp$_2$ZrHCl (103 mg, 0.40 mmol, 2.0 eq) was added to a stirred, room temperature, solution of 4-phenyl-1-butene (75 μL, 0.50 mmol, 2.50 eq) in CH$_2$Cl$_2$ (0.20 mL) under an argon atmosphere. After 40 min the solution became clear and yellow. AgNTf$_2$ (8.5 mg, 0.022 mmol, 0.11 eq) was then added to the Cu-ligand mixture and it was stirred for 10 min and filtered via syringe over 1 min to the hydrozirconation reaction flask. The resulting dark mixture was allowed to stir for an additional 10 min before 3-ethyl-2-cyclohexenone (22 μL, 0.17 mmol, 0.85 eq) was added dropwise via syringe. Stirring at room temperature was continued for 12 h before the reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (+)-(R)-3-ethyl-3-(4-phenylbutyl)cyclohexanone 5 (25 mg, 0.09 mmol, 58%) as a colourless oil. HPLC indicated an enantiomeric excess of 92% [Chiralpak® ID; flow: 1 mL/min; hexane/i-PrOH: 99:1; λ=210 nm; major enantiomer (+)-(R)-3-ethyl-3-(4-phenylbutyl)cyclohexanone, $t_R$=9.72 min; minor enantiomer (−)-(S)-3-ethyl-3-(4-phenylbutyl)cyclohexanone, $t_R$=9.44 min]. $^1$H NMR (400 MHz, CDCl$_3$) δ$_H$/ppm 7.24-7.35 (m, 2 H), 7.12-7.23 (m, 3 H), 2.62 (t, J=7.8 Hz, 2 H), 2.28 (t, J=6.7 Hz, 2 H), 2.13-2.21 (m, 2 H), 1.78-1.89 (m, 1 H), 1.49-1.67 (m, 4 H), 1.16-1.37 (m, 6 H), 0.76 (t, J=7.6 Hz, 3 H). $^{13}$C NMR (100 MHz, CDCl$_3$) δ$_C$/ppm 212.9, 142.8, 128.6 (3C), 125.9 (2C), 52.1, 41.3, 41.1, 36.6, 36.1, 33.6, 32.3, 29.7, 22.7, 21.9, 7.6. HRMS (ESI) m/z calcd for C$_{18}$H$_{26}$NaO [M+Na]$^+$: 281.1876, found: 281.1875. [α]$^{20}_{589}$=+2.40 (c 0.50, CHCl$_3$). IR (ATR) v (cm$^{-1}$): 1496, 1604, 1713, 2925, 3025.

Example 24

(+)-(R)-3,3,5-Trimethyl-5-(4-phenylbutyl)cyclohexanone (6)

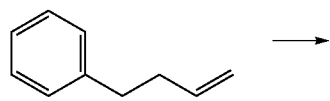

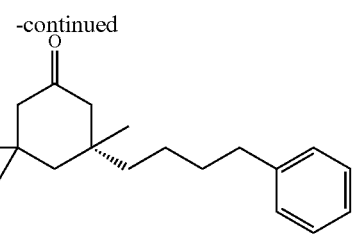

CuCl (3.1 mg, 0.030 mmol, 0.10 eq) and ligand C (17.3 mg, 0.030 mmol, 0.10 eq) were dissolved in t-BuOMe (1.5 mL) under an argon atmosphere and allowed to stir for 1 h at room temperature. AgNTf$_2$ (13.4 mg, 0.035 mmol, 0.11 eq) was added and the suspension was stirred for another 15 min. In another flask, Cp$_2$ZrHCl (161.9 mg, 0.63 mmol, 2.0 eq) was added to a stirred, room temperature, solution of 4-phenyl-1-butene (0.12 mL, 0.78 mmol, 2.5 eq) in CH$_2$Cl$_2$ (0.40 mL) under an argon atmosphere. After stirring for 1 min, the stirred solution containing the copper and ligand was transferred and filtered using a syringe filter to the clear yellow solution. The resulting black mixture was allowed to stir for an additional 10 min before isophorone (47 μL, 0.31 mmol, 1.0 eq) and TMSCl (0.19 mL, 1.5 mmol) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (+)-(R)-3,3,5-trimethyl-5-(4-phenylbutyl)cyclohexanone 6 (29 mg, 0.11 mmol, 34%) as a yellow oil. HPLC analysis indicated an enantiomeric excess of 73% [Chiralpak® AY-H; flow: 1 mL/min; hexane/i-PrOH: 95:5; λ=210 nm; major enantiomer (+)-(R)-3,3,5-trimethyl-5-(4-phenylbutyl)cyclohexanone, $t_R$=6.8 min; minor enantiomer (−)-(S)-3,3,5-trimethyl-5-(4-phenylbutyl)cyclohexanone, $t_R$=8.0 min]. $^1$H NMR (400 MHz, CDCl$_3$) δ$_H$/ppm 7.17-7.26 (m, 2 H), 7.06-7.14 (m, 3 H), 2.54 (t, J=7.6 Hz, 2 H), 2.07-2.16 (m, 3 H), 2.05 (m, J=0.7 Hz, 1 H), 1.39-1.59 (m, 4 H), 1.14-1.35 (m, 4 H), 0.96 (s, 6 H), 0.92 (s, 3 H). $^{13}$C NMR (100 MHz, CDCl$_3$) δ$_C$/ppm 212.6, 142.5, 128.3 (2 C), 128.3 (2C), 125.7, 54.3, 53.1, 49.0, 44.6, 38.8, 36.1, 35.9, 32.2, 32.1, 30.6, 27.4, 23.0. HRMS (ESI) m/z calcd for C$_{19}$H$_{28}$NaO [M+Na]$^+$: 295.2032, found: 295.2025. [α]$^{20}_{589}$=+4.30 (c 1.15, CHCl$_3$). IR (ATR) v (cm$^{-1}$): 699, 747, 903, 1279, 1496, 1667, 1712, 2951.

Example 25

(−)-(R)-3-Hexyl-3-methylcycloheptanone (7a)

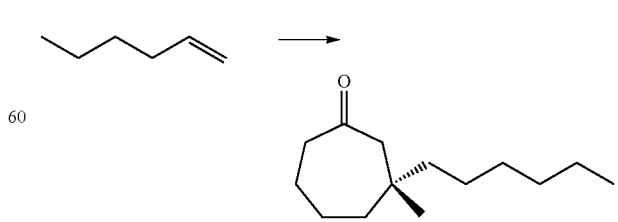

CuCl (3.1 mg, 0.030 mmol, 0.10 eq) and ligand C (17.3 mg, 0.030 mmol, 0.10 eq) were dissolved t-BuOMe (1.5 mL) under an argon atmosphere and allowed to stir for 1 h at room temperature. AgNTf$_2$ (13.4 mg, 0.035 mmol, 0.11 eq) was added and the suspension was stirred for another 15 min. In another flask, Cp$_2$ZrHCl (161.9 mg, 0.63 mmol, 2.0 eq) was added to a stirred, room temperature, solution of 1-hexene (0.10 mL, 0.78 mmol, 2.5 eq) in CH$_2$Cl$_2$ (0.31 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cycloheptenone (41 μL, 0.31 mmol, 1.0 eq) was added dropwise via syringe. Stirring continued 12 h before the reaction was quenched by the addition of Et$_2$O (ca 3 mL) and then NH$_4$Cl (1 M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:19 EtOAc/petrol; SiO$_2$) gave (−)-(R)-3-Hexyl-3-methylcycloheptanone 7a (45 mg, 0.21 mmol, 70%) as a colourless oil.

Enantiomeric excess (90% ee) was determined by HPLC analysis of the corresponding enone. The enone was obtained as follows: a flask containing Pd(TFA)$_2$ (18.9 mg, 0.057 mmol, 1 eq) and the ketone 7a (12 mg, 0.057 mmol, 1 eq) was flashed with oxygen (balloon, 1 atm). DMSO (8 μL, 0.11 mmol, 2 eq) and toluene (0.5 mL) were added and the suspension was warmed at 80° C. for 12 hours. After cooling down, the mixture was concentrated in vacuo and purified by flash column chromatography (1:19 EtOAc/petrol; SiO$_2$) to give the desired enone that was directly analysed by HPLC. HPLC analysis indicated an enantiomeric excess of 90% [Chiralpak® IC; flow: 1 mL/min; hexane/i-PrOH: 95:5; λ=225 nm; major enantiomer (−)-(R)-3-Methyl-3-(4-phenylhexyl)cyclohexanone t$_R$=20.2 min; minor enantiomer (+)-(S)-3-Methyl-3-(4-phenylhexyl)cyclohexanone, t$_R$=21.4 min]. $^1$H NMR (400 MHz, CDCl$_3$) δ$_H$/ppm 2.45 (d, J=12.0 Hz, 1 H), 2.26-2.38 (m, 3 H), 1.64-1.77 (m, 2 H), 1.49-1.63 (m, 3 H), 1.37-1.47 (m, 1 H), 1.08-1.29 (m, 10 H), 0.78-0.86 (m, 6 H). $^{13}$C NMR (100 MHz, CDCl$_3$) δ$_C$/ppm 214.3, 54.8, 43.9, 42.5 (2 C), 35.2, 31.8, 30.0, 26.0, 24.7, 24.2, 23.4, 22.6, 14.1. HRMS (ESI) m/z calcd for C$_{14}$H$_{26}$NaO [M+Na]$^+$: 233.1876 found: 233.1876. [α]$^{20}_{589}$=−0.60 (c 0.95, CHCl$_3$). IR (ATR) ν (cm$^{-1}$): 699, 1229, 1368, 1455, 1730, 2929.

Example 26

(+)-(R)-3-Methyl-3-(4-phenylbutyl)cycloheptanone (7b)

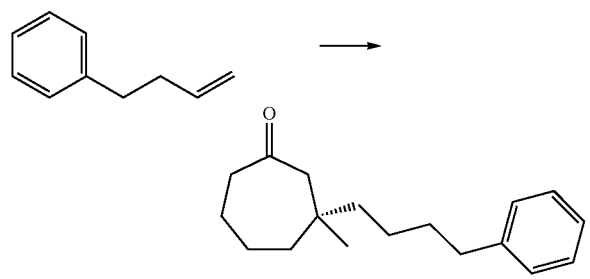

CuCl (3.1 mg, 0.030 mmol, 0.10 eq) and ligand C (17.3 mg, 0.030 mmol, 0.10 eq) were dissolved in CH$_2$Cl$_2$ (1.5 mL) under an argon atmosphere and allowed to stir for 1 h at room temperature. AgNTf$_2$ (13.4 mg, 0.035 mmol, 0.11 eq) was added and the suspension was stirred for another 15 min. In another flask, Cp$_2$ZrHCl (161.9 mg, 0.63 mmol, 2.0 eq) was added to a stirred, room temperature, solution of 4-phenyl-1-butene (0.12 mL, 0.78 mmol, 2.5 eq) in CH$_2$Cl$_2$ (0.31 mL) under an argon atmosphere. After stirring for 15 min, the stirred solution containing the copper and ligand was transferred and filtered using a syringe filter to the clear yellow solution. The resulting black mixture was allowed to stir for an additional 10 min before 3-methyl-2-cycloheptenone (41 μL, 0.31 mmol, 1.0 eq) was added dropwise via syringe. Stirring continued 12 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (+)-(R)-3-methyl-3-(4-phenylbutyl)cycloheptanone 7b (41 mg, 0.16 mmol, 51%) as a colourless oil. HPLC indicated an enantiomeric excess of 82% [Chiralpak® IC; flow: 1 mL/min; hexane/i-PrOH: 95:5; λ=210 nm; major enantiomer (+)-(R)-3-methyl-3-(4-phenylbutyl)cycloheptanone, t$_R$=10.7 min; minor enantiomer (−)-(S)-3-methyl-3-(4-phenylbutyl)cycloheptanone, t$_R$=11.7 min]. $^1$H NMR (400 MHz, CDCl$_3$) δ$_H$/ppm 7.16-7.26 (m, 2 H), 7.04-7.13 (m, 3 H), 2.54 (t, J=7.6 Hz, 2 H), 2.45 (d, J=12.0 Hz, 1 H), 2.25-2.36 (m, 3 H), 1.64-1.75 (m, 2 H), 1.37-1.63 (m, 6 H), 1.10-1.34 (m, 4 H), 0.81 (s, 3 H). $^{13}$C NMR (100 MHz, CDCl$_3$) δ$_C$/ppm 214.2, 142.6, 128.3 (2 C), 128.2 (2 C), 125.6, 54.7, 43.9, 42.6, 42.4, 35.9, 35.2, 32.1, 25.9, 24.6, 24.1, 23.1. HRMS (ESI) m/z calcd for C$_{18}$H$_{26}$NaO [M+Na]$^+$: 281.1876, found: 281.1876. [α]$^{20}_{589}$=+4.83 (c 0.63, CHCl$_3$). IR (ATR) ν (cm$^{-1}$): 699, 1454, 1713, 2360, 3026.

Example 27

(R)-4a-methyl-3,4,4a,5,6,7-hexahydronaphthalen-1(2H)-one (8)

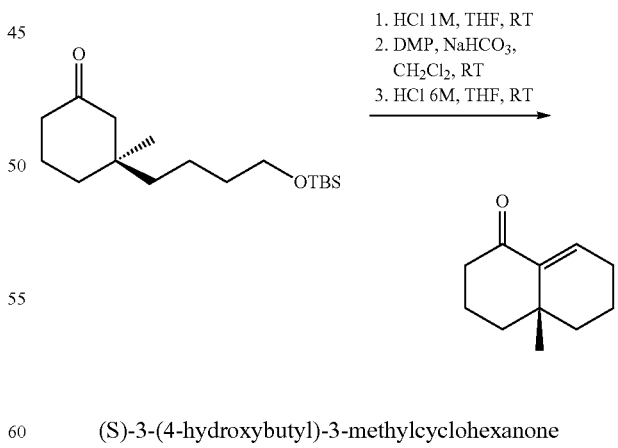

(S)-3-(4-hydroxybutyl)-3-methylcyclohexanone

To a stirred solution of (+)-(R)-3-(4-((tert-Butyldimethylsilyl)oxy)butyl)-3-methylcyclohexanone 3m (110 mg, 0.37 mmol, 1.0 eq) in THF (3.7 mL) a 1M aqueous solution of HCl was added and the resulting mixture was stirred at room temperature for 3 h. The mixture was then poured into 5 mL of saturated NaHCO$_3$ solution. The aqueous layer was then extracted with Et$_2$O (3×3 mL) and the combined organic extracts were washed with brine, dried over MgSO$_4$, filtered and evaporated. The crude product was purified by flash column chromatography (Petrol:EtOAc, 7:3) to afford 57 mg of the unprotected alcohol (84%).

(S)-4-(1-methyl-3-oxocyclohexyl)butanal

The above prepared alcohol (33 mg, 0.18 mmol,1.0 eq) was dissolved in CH$_2$Cl$_2$ (1.8 mL) and NaHCO$_3$ (151 mg, 0.21 mmol, 10 eq) was then added and the mixture was cooled to 0° C. and Dess-Martin periodinane (91 mg, 1.80 mmol, 1.20 eq) was added in one portion and the solution was allowed to reach room temperature. After 1 h a saturated solution of Na$_2$S$_2$O$_3$ (5 mL) was added. The aqueous phase was extracted with CH$_2$Cl$_2$ (3×2 mL). The combined organic extracts were washed with water, dried over MgSO$_4$, filtered and concentrated. A filtration through a silica pad provided the desired aldehyde that was used in the next step without further purification.

(R)-4a-methyl-3,4,4a,5,6,7-hexahydronaphthalen-1 (2H)-one

HCl (0.1 mL) was added to a stirring solution of the aldehyde (20 mg, 0.11 mmol) in THF (1.2 mL). The reaction was stirred overnight and then it was neutralised with NaHCO$_3$ at 0° C. It was then diluted with Et$_2$O and the organic phase was washed with water and brine. Flash column chromatography (Petrol:EtOAc, 7:3) afforded the desired product (R)-8 in 83% yield (15 mg, 0.09 mmol). The spectroscopic data was identical at that reported in d'Augustin et al (Chem. Eur. J., 2007, 13, 9647-9662) for the opposite enantiomer. [α]$^{20}_{559}$=+78.2 (c 0.50, CHCl$_3$).

Examples 28-61

General Procedures

Synthesis of Phosphoramidite Ligands

According to a modified procedure from Trost et al (J. Am. Chem. Soc., 2011, 133 (48), 19483-19497), triethylamine (5.0 eq.) is added dropwise to a stirred ice-cooled solution of PCl$_3$ (1.0 eq.) in CH$_2$Cl$_2$ (7 mL×mmol amine). The ice bath is removed and the solution left to warm to room temperature before amine (1.0 eq.) is added to the stirring solution. After 5 additional hours of stirring, binaphthol (1.0 eq.) is added to the suspension and the subsequent mixture is left to stir for an additional 18 h. The solution is then filtered on a small pad of silica and Celite® and rinsed with CH$_2$Cl$_2$ (~20 mL). The resulting solution is concentrated under reduced pressure to afford a yellow residue. After flash column chromatography, the ligand is obtained as a crystalline solid.

Synthesis of Alkyl Amines

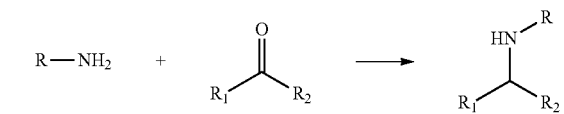

R = e.g. alkyl
R$_1$ = e.g. alkyl or H
R$_2$ = e.g. alkyl or aryl

According to a modified procedure from Davies et al (supra), the corresponding ketone (2.0 eq.) is added to a stirring solution of primary amine (1.0 eq) in THF (~0.2 M) at room temperature. After 5 min, NaB(OAc)$_3$H (1.5 eq.) is added into the reaction mixture at room temperature and the resulting suspension is stirred for 18-48 h. Et$_2$O (15 mL) and NaHCO$_3$ (aq. sat., ca 10 mL) are added to the suspension and stirring is continued for 30 min. The mixture is partitioned between the aqueous and Et$_2$O layers and the aqueous phase extracted with Et$_2$O (3×10 mL). The combined organic phase is dried (MgSO$_4$), filtered and concentrated under reduced pressure to afford the desired title amine.

In the case of recrystallization, the crude residue is then suspended in Et$_2$O, HCl (37% aq. solution) is added (2-5 drops) until a white solid precipitated. The precipitate is isolated by filtration and washed with EtOAc and then recrystallized to give the HCl salt of the desired secondary amine. The crystals are added to a stirring biphasic mixture containing CH$_2$Cl$_2$ and a saturated NaOH solution. After stirring for 15 minutes the phases are separated and the aqueous phase is extracted with CH$_2$Cl$_2$ (3×10 mL), dried (Na$_2$SO$_4$), filtered and concentred in vacuo to afford the desired secondary amine. The amine is used without further purification or recrystallization.

In some cases, the above reaction can be followed immediately by the creation of the corresponding ligand.

Synthesis of Aryl Amines

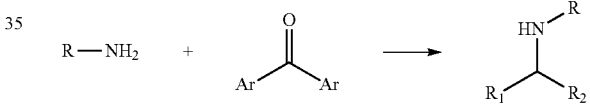

R = e.g. alkyl or aryl
Ar = aryl

According to a modified procedure from Hampton et al (Chemmedchem, 2011, 6(10)), TiCl$_4$ (1.1 eq, 1 M solution in DCM) is added slowly to an ice-bathed solution of arylketone (1.0 eq) in DCM (0.2 M solution). The solution is stirred for 10 minutes at room temperature and then a solution of amine (2.2 eq) in THF (2 M solution) is added dropwise to the reaction mixture. The reaction flask is stirred for 3 hours. A solution of NaB(CN)H$_3$ (1.2 eq) in THF (1 M solution) is added slowly to the reaction mixture. MeOH (⅓ volume of DCM of first solution) is added slowly to the reaction mixture. The reaction mixture is stirred at room temperature for 18 hours. NaOH (2M aq solution) is added slowly and the reaction mixture is stirred for 30 min. The reaction mixture is filtered on Celite® and washed with EtOAc. NaHCO$_3$ (aq. sat.) are added to the suspension. The mixture is partitioned between the aqueous and organic layers and the aqueous phase extracted with EtOAc (3 times). The combined organic phase is dried over MgSO$_4$, filtered and concentrated in vacuo to give an oil. Purification by flash column chromatography (SiO$_2$) gave the desired amine.

Example 28

N-isopropyl-9H-fluoren-9-amine

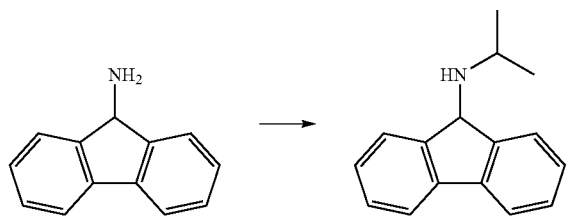 [SMILES: NC1c2ccccc2-c2ccccc21 ; CC(C)NC1c2ccccc2-c2ccccc21]

Acetone (1.50 mL, 5.5 mmol, 2.0 eq.) was added to a stirring solution of 9H-fluoren-9-amine (500 mg, 2.76 mmol, 1.0 eq.) in THF (10 mL) at room temperature. After 5 min, NaB(OAc)$_3$H (0.87 g, 2.84 mmol, 1.5 eq.) was added into the reaction mixture at room temperature and the resulting suspension was stirred for 48 h. Et$_2$O (20 mL) and NaHCO3 (aq. sat., ca 20 mL) were added to the suspension and stirring was continued for 30 min. The mixture was partitioned between the aqueous and Et$_2$O layers and the aqueous phase extracted with Et$_2$O (3×20 mL). The combined organic phase was dried (MgSO$_4$), filtered and concentrated under reduced pressure to afford the desired title product as a colourless oil (0.535 g, 2.39 mmol, 87%). The amine was used without further purification. $^1$H NMR (400 MHz, CDCl$_3$) b 7.67-7.81 (m, 4 H), 7.33-7.49 (m, 4 H), 4.96 (s, 1 H), 3.30 (dt, J=12.2, 6.1 Hz, 1 H), 2.07 (br. s., 1 H), 1.18 (d, J=6.4 Hz, 6 H). $^{13}$C NMR (100 MHz, CDCl$_3$) b ppm 159.6, 147.5, 129.2, 118.7, 112.0, 111.8, 55.0, 54.9, 45.4, 24.6, 23.8, 21.9. HRMS (ESI) m/z calcd for C$_{16}$H$_{18}$N [M]$^+$: 224.1434, found: 224.1443. IR (v$_{max}$/cm$^{-1}$) 2961, 1600, 1256, 1047, 749.

Example 29

N-benzhydrylcyclohexanamine

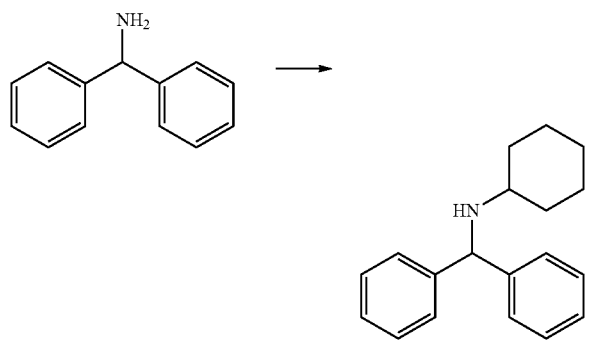

Cyclohexanone (0.63 mL, 6.11 mmol, 1.1 eq) was added to a stirred solution of diphenylmethanamine (1.20 mL, 6.42 mmol, 1.0 eq) in THF (20 mL) at room temperature. After 5 minutes, NaB(OAc)$_3$H (1.94 g, 9.21 mmol, 1.5 eq) was added in one portion. The resulting suspension was stirred for about 48 hours, before Et$_2$O (10 mL) and NaHCO$_3$ (aq. sat., ca 10 mL) were added to the suspension and stirring was continued for 15 additional minutes. The mixture was partitioned between the aqueous and Et$_2$O layers and the aqueous phase extracted with Et$_2$O (3×10 mL). The combined organic phase was concentrated in vacuo (~5 mL). Then HCl (aq 2.0 M, 1 mL) was added dropwise. The mixture was partitioned between the aqueous and Et$_2$O layers and the organic phase extracted with HCl (aq 2.0 M, 3×10 mL). Then CH$_2$Cl$_2$ (20 mL) was added to the combined aqueous phases and NaOH (saturated with brine aq solution, 25%) was added until the mixture became basic (pH paper, pH~14). The mixture was partitioned between the aqueous and CH$_2$Cl$_2$ layers and the aqueous phase extracted with CH$_2$Cl$_2$ (3×10 mL). The combined organic phase was dried (MgSO$_4$), filtered and concentrated in vacuo to afford the desired N-benzhydrylcyclohexanamine (1.01 g, 3.76 mmol, 61%). The amine was used without further purification. $^1$H NMR (400 MHz, CDCl$_3$) δ$_H$/ppm 7.39 (d, J=7.1 Hz, 4H), 7.25-7.33 (m, 4 H), 7.15-7.23 (m, 2 H), 5.05 (s, 1 H), 2.35-2.52 (m, 1 H), 1.96 (br. d, J=11.6 Hz, 2 H), 1.65-1.78 (m, 2 H), 1.57 (br. s., 1 H), 1.35 (br. s, 1 H), 1.03-1.26 (m, 5 H). $^{13}$C NMR (100 MHz, CDCl$_3$) δ$_C$/ppm 144.8 (2 C), 128.3 (4C), 127.3 (4C), 126.7 (2 C), 63.6, 53.9, 33.9 (2 C), 26.2, 24.3-25.6 (2 C). MS (ESI) m/z [M+H]$^+$: 266.2 (100). IR (v$_{max}$/cm$^{-1}$): 3025, 2925, 2890, 1739, 1492, 1368, 1229, 700.

Example 30

N-benzhydrylcyclopentanamine

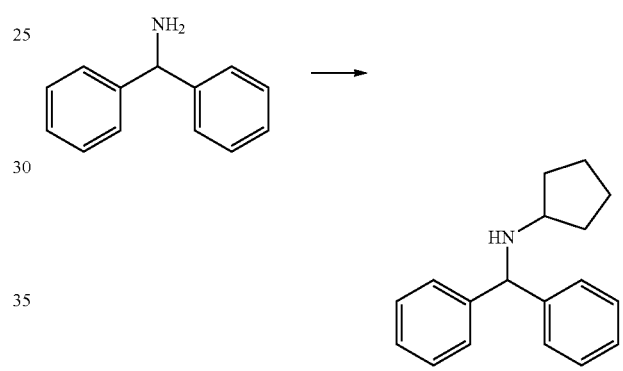

Cyclopentanone (0.63 mL, 7.13 mmol, 1.1 eq) was added to a stirred solution of diphenylmethanamine (1.20 mL, 6.42 mmol, 1.0 eq) in THF (20 mL) at room temperature. After 5 minutes, NaB(OAc)$_3$H (2.13 g, 10.7 mmol, 1.5 eq) was added in one portion. The resulting suspension was stirred for about 48 hours, before Et$_2$O (10 mL) and NaHCO$_3$ (aq. sat., ca 10 mL) were added to the suspension and stirring was continued for 15 additional minutes. The mixture was partitioned between the aqueous and Et$_2$O layers and the aqueous phase extracted with Et$_2$O (3×10 mL). The combined organic phase was concentrated in vacuo (~5 mL). Then HCl (aq 2.0 M, 1 mL) was added dropwise. The mixture was partitioned between the aqueous and Et$_2$O layers and the organic phase extracted with HCl (aq 2.0 M, 3×10 mL). Then CH$_2$Cl$_2$ (20 mL) was added to the combined aqueous phases and NaOH (saturated with brine aq solution, 25%) was added until the mixture became basic (pH paper, pH~14). The mixture was partitioned between the aqueous and CH$_2$Cl$_2$ layers and the aqueous phase extracted with CH$_2$Cl$_2$ (3×15 mL). The combined organic phase was dried (MgSO$_4$), filtered and concentrated in vacuo to afford the desired N-benzhydrylcyclopentanamine (1.30 g, 5.17 mmol, 76%). The amine was used without further purification. $^1$H NMR (400 MHz, CDCl$_3$) δ$_H$/ppm 7.41-7.51 (m, 4 H), 7.35 (apparent td, J=7.6, 1.7 Hz, 4 H), 7.21-7.30 (m, 2 H), 2.96-3.15 (m, 1 H), 1.83-2.00 (m, 2 H), 1.72 (br. s., 2 H), 1.48-1.63 (m, 3 H), 1.35-1.46 (m, 2 H). $^{13}$C NMR (100 MHz, CDCl$_3$) δ$_C$/ppm 144.5 (2 C), 128.4 (4 C), 127.2-127.6 (m, 4C), 126.5-127.0 (m, 2 C), 65.6, 57.6, 33.2 (2 C), 23.8 (2 C). MS (ESI) m/z [M+H]$^+$: 252.2 (100). IR (v$_{max}$/cm$^{-1}$): 2970, 1739, 1449, 1367, 1229, 700.

Example 31

N-benzhydrylcyclooctanamine

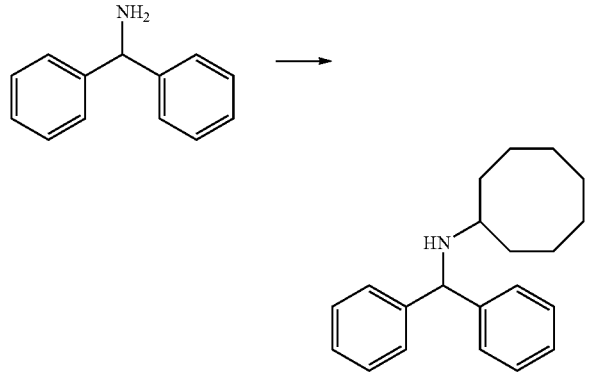

Cycloctanone (0.7363 mL, 5.54 mmol, 1.1 eq) was added to a stirred solution of diphenylmethanamine (0.86 mL, 4.9 mmol, 1.0 eq) in THF (20 mL) at room temperature. After 5 minutes, NaB(OAc)$_3$H (1.764 g, 8.3 mmol, 1.5 eq) was added in one portion. The resulting suspension was stirred for about 48 hours, before Et$_2$O (10 mL) and NaHCO$_3$ (aq. sat., ca 10 mL) were added to the suspension and stirring was continued for 15 additional minutes. The mixture was partitioned between the aqueous and Et$_2$O layers and the aqueous phase extracted with Et$_2$O (3×10 mL). The combined organic phase was concentrated in vacuo (~5 mL). Then HCl (aq 2.0 M, 1 mL) was added dropwise. The mixture was partitioned between the aqueous and Et$_2$O layers and the organic phase extracted with HCl (aq 2.0 M, 3×10 mL). Then CH$_2$Cl$_2$ (20 mL) was added to the combined aqueous phases and NaOH (saturated with brine aq solution, 25%) was added until the mixture became basic (pH paper, pH~14). The mixture was partitioned between the aqueous and CH$_2$Cl$_2$ layers and the aqueous phase extracted with CH$_2$Cl$_2$ (3×10 mL). The combined organic phase was dried (MgSO$_4$), filtered and concentrated in vacuo to afford the desired N-benzhydrylcyclooctanamine (0.98 g, 3.34 mmol, 60%). The amine was used without further purification. $^1$H NMR (400 MHz, CDCl$_3$) $\delta_H$/ppm 7.57-7.78 (m, 4 H), 7.45-7.55 (m, 4 H), 7.33-7.44 (m, 2 H), 5.21 (s, 1 H), 2.89 (br. s., 1 H), 2.04 (s, 2 H), 1.93 (br. s., 2 H), 1.51-1.85 (m, 11 H). $^{13}$C NMR (100 MHz, CDCl$_3$) $\delta_C$/ppm 144.5 (2 C), 128.1 (4 C), 127.2 (4 C), 126.6 (2 C), 63.8, 54.2, 31.8 (2 C), 27.4 (2C), 25.4, 23.1. HRMS (ESI) m/z calcd for C$_{21}$H$_{28}$N [M]$^+$: 294.2209, found: 294.2216. IR ($v_{max}$/cm$^{-1}$): 1738, 1492, 1368, 751.

Example 32

N-(bis(3,5-bis(trifluoromethyl)phenyl)methyl)propan-2-amine

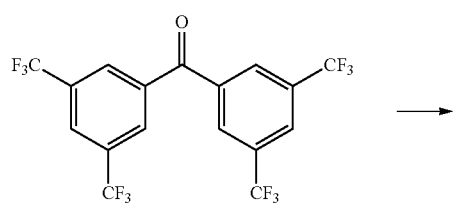

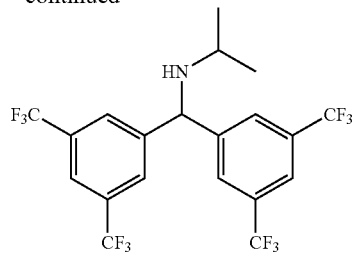

TiCl$_4$ (6.1 mL, 6.1 mmol, 1.1 eq, 1 M solution in DCM) was added slowly to an ice-bathed solution of bis(3,5-bis(trifluoromethyl)phenyl)methanone (2.5 g, 5.5 mmol, 1.0 eq) in DCM (30 mL). The solution was stirred for 5 minutes at room temperature and a solution of isopropylamine (1.0 mL, 12.1 mmol, 2.2 eq) in THF (6 ml, 2 M solution) was added dropwise to the reaction mixture. The reaction flask was stirred for 3 hours. A solution of NaB(CN)H$_3$ (0.415 g, 6.61 mmol, 1.2 eq) in THF (7 mL, 1 M solution) was added slowly to the reaction mixture. MeOH (10 mL) was added slowly to the reaction mixture. The reaction mixture was stirred at room temperature for 18 hours. NaOH (~20 mL, 2M aq solution) was added slowly and the reaction mixture was stirred for 30 min. The reaction mixture was filtered on Celite® and washed with EtOAc (~30 mL). The mixture was partitioned between the aqueous and organic layers and the aqueous phase extracted with EtOAc (3×10 mL). The combined organic phase was dried (MgSO$_4$), filtered and concentrated in vacuo to afford a yellow oil. Flash column chromatography of the residue (Petrol: CH$_2$Cl$_2$: Et$_2$O; 89:10:1; SiO$_2$) gave the desired N-(bis(3,5-bis(trifluoromethyl)phenyl)methyl)-propan-2-amine (0.73 g, 1.46 mmol, 27%). $^1$H NMR (300 MHz, CDCl$_3$) $\delta_H$/ppm 7.88 (s, 4 H), 7.80 (s, 2 H), 5.21 (s, 1 H), 2.70 (spt, J=6.2 Hz, 1 H), 1.27 (br. s., 1 H), 1.14 (d, J=6.2 Hz, 6 H). $^{13}$C NMR (100 MHz, CDCl$_3$) $\delta_C$/ppm 145.5 (2 C), 131.0-133.2 (m, 2 C), 127.3-127.4 (m, 2 C), 127.3 (2 C), 124.5 (2 C), 121.8 (s, 2 C), 63.4, 46.6, 23.1 (2 C). $^{19}$F NMR (380 MHz, CDCl$_3$) $\delta_F$/ppm -62.85 (s, 12F). HRMS (ESI) m/z calcd for C$_{20}$H$_{16}$F$_{12}$N [M+H]$^+$: 498.1085, found: 498.1086. IR ($v_{max}$/cm$^{-1}$): 1371, 1276, 1168, 1126, 898, 712.

Example 33

N-(bis(3-(trifluoromethyl)phenyl)methyl)propan-2-amine

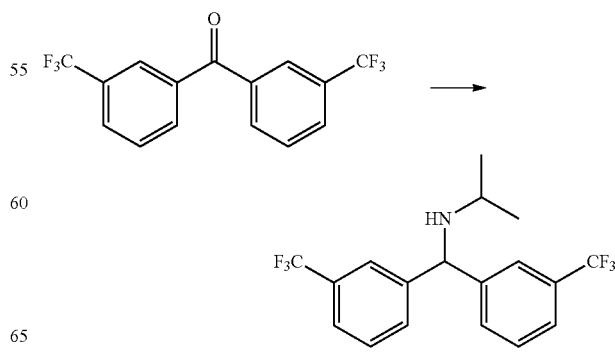

TiCl$_4$ (3.5 mL, 3.50 mmol, 1.1 eq, 1 M solution in DCM) was added slowly to an ice-bathed solution of bis(3-(trifluoromethyl)phenyl)methanone (1.0 g, 4.00 mmol, 1.0 eq) in DCM (17 mL). The solution was stirred for 15 minutes at room temperature and a solution of isopropylamine (0.59 mL, 6.90 mmol, 2.2 eq) in THF (3 ml, ~1.5 M solution) was added dropwise to the reaction mixture. The reaction flask was stirred for 3 hours. A solution of NaB(CN)H$_3$ (0.237 g, 3.77 mmol, 1.2 eq) in THF (4 mL, 1 M solution) was added slowly to the reaction mixture. MeOH (5.7 mL) was added slowly to the reaction mixture. The reaction mixture was stirred at room temperature for 18 hours. NaOH (~10 mL, 2M aq solution) was added slowly and the reaction mixture was stirred for 30 min. The reaction mixture was filtered on Celite® and washed with EtOAc (~10 mL). NaHCO$_3$ (aq. sat., ca 10 mL) were added to the suspension. The mixture was partitioned between the aqueous and organic layers and the aqueous phase extracted with EtOAc (3×10 mL). The combined organic phase was concentrated in vacuo. Et$_2$O (~10 mL) was added to the oil. HCl (aq 2.0 M, ~2 mL) was added dropwise for about 1 min. HBr (1 mL, aq, 55% solution) was added dropwise and the mixture was left for 1 hour. The mixture was partitioned between the aqueous and Et$_2$O layers and the organic phase extracted with HCl (aq 2.0 M, 15 mL). Then CH$_2$Cl$_2$ (10 mL) was added to the combined aqueous phases and NaOH (aq saturated with brine solution, 25%) was added until the mixture became basic (pH paper, pH~14). The mixture was partitioned between the aqueous and CH$_2$Cl$_2$ layers and the aqueous phase extracted with CH$_2$Cl$_2$ (3×10 mL). The combined organic phase was dried (MgSO$_4$), filtered and concentrated in vacuo to afford the desired N-(bis(3-(trifluoromethyl)phenyl)methyl)propan-2-amine (0.545 g, 1.5 mmol, 48%). The amine was used without further purification. $^1$H NMR (400 MHz, CDCl$_3$) $\delta_H$/ppm 7.69 (s, 2 H), 7.58 (d, J=7.6 Hz, 2 H), 7.48-7.53 (m, 2 H), 7.40-7.47 (m, 2 H), 5.09 (s, 1 H), 2.72 (spt, J=6.3 Hz, 1 H), 1.27 (br. s., 1 H), 1.11 (d, J=6.3 Hz, 6 H). $^{13}$C NMR (100 MHz, CDCl$_3$) $\delta_C$/ppm 144.8 (br. s., 2 C), 131.2 (2 C), 130.7 (2 C), 129.1 (4 C), 124.2 (q, J=4.0 Hz, 1 C), 124.0 (q, J=4.0 Hz, 1 C), 63.8, 46.3, 23.1 (2 C). $^{19}$F NMR (380 MHz, CDCl$_3$) $\delta_F$/ppm −62.51 (s, 6 F). HRMS (ESI) m/z calcd for C$_{16}$H$_{10}$F$_{10}$N [M+H]$^+$: 406.0648, found: 406.0639. IR ($v_{max}$/cm$^{-1}$): 2966, 1449, 1325, 1163, 1120, 707.

Example 34

N-(di-p-tolylmethyl)propan-2-amine

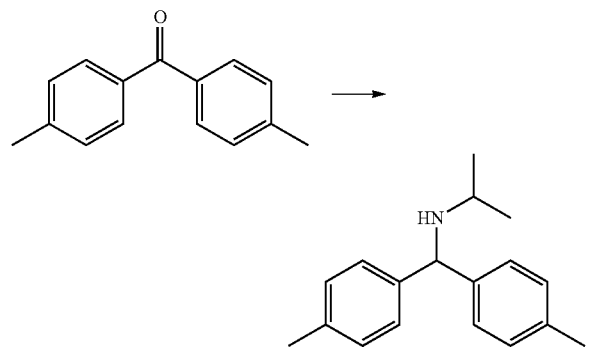

TiCl$_4$ (4.4 mL, 4.4 mmol, 1.1 eq, 1 M solution in DCM) was added slowly to an ice-bathed solution of di-p-tolyl-methanone (0.850 g, 4.0 mmol, 1.0 eq) in DCM (22 mL). The solution was stirred for 5 minutes at room temperature and a solution of isopropylamine (0.76 mL, 8.90 mmol, 2.2 eq) in THF (5 ml, ~1.5 M solution) was added dropwise to the reaction mixture. The reaction flask was stirred for 3 hours. A solution of NaB(CN)H$_3$ (0.305 g, 4.85 mmol, 1.2 eq) in THF (5 mL, 1 M solution) was added slowly to the reaction mixture. MeOH (7.5 mL) was added slowly to the reaction mixture. The reaction mixture was stirred at room temperature for 18 hours. NaOH (~10 mL, 2M aq solution) was added slowly and the reaction mixture was stirred for 30 min. The reaction mixture was filtered on Celite® and washed with EtOAc (~10 mL). NaHCO$_3$ (aq. sat., ca 10 mL) were added to the suspension. The mixture was partitioned between the aqueous and organic layers and the aqueous phase extracted with EtOAc (3×10 mL). The combined organic phase was concentrated in vacuo. Et$_2$O (~10 mL) was added to the oil. Then HCl (aq 2.0 M, ~2 mL) was added dropwise for about 1 min. The mixture was partitioned between the aqueous and Et$_2$O layers and the organic phase extracted with HCl (aq 2.0 M, 15 mL). Then CH$_2$Cl$_2$ (20 mL) was added to the combined aqueous phases and NaOH (aq saturated with brine solution, 25%) was added until the mixture became basic (pH paper, pH~14). The mixture was partitioned between the aqueous and CH$_2$Cl$_2$ layers and the aqueous phase extracted with CH$_2$Cl$_2$ (3×10 mL). The combined organic phase was dried (MgSO$_4$), filtered and concentrated in vacuo to afford the desired N-(di-p-tolyl-methyl)propan-2-amine (0.622 g, 2.45 mmol, 61%). The amine was used without further purification. $^1$H NMR (400 MHz, CDCl$_3$) $\delta_H$/ppm 7.24-7.30 (m, 4 H), 7.11 (d, J=8.1 Hz, 4 H), 4.92 (s, 1 H), 2.75 (spt, J=6.3 Hz, 1 H), 2.32 (s, 6 H), 1.38 (br. s., 1 H), 1.09 (d, J=6.3 Hz, 6 H). $^{13}$C NMR (100 MHz, CDCl$_3$) $\delta_C$/ppm 141.8 (2 C), 136.2 (2 C), 129.1 (4 C), 127.2 (4 C), 63.6, 46.0, 23.2 (2 C), 21.0 (2 C). HRMS (ESI) m/z calcd for C$_{18}$H$_{24}$N [M+H]$^+$: 254.1903, found: 254.1902. IR ($v_{max}$/cm$^{-1}$): 2960, 1510, 1460, 1167, 807, 768.

Example 35

N-(bis(4-methoxyphenyl)methyl)propan-2-amine

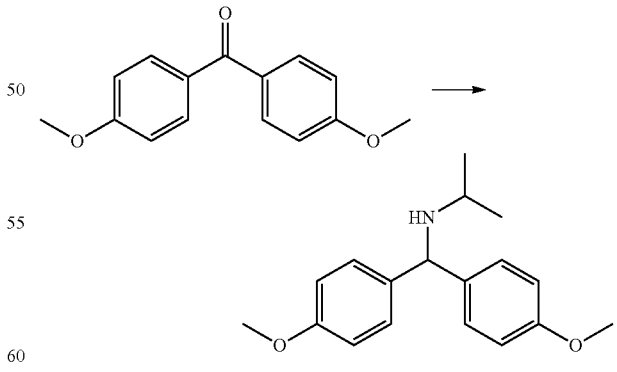

TiCl$_4$ (7.7 mL, 7.7 mmol, 1.1 eq, 1 M solution in DCM) was added slowly to an ice-bathed solution of bis(4-methoxyphenyl)methanone (1.7 g, 7.0 mmol, 1.0 eq) in DCM (38 mL). The solution was stirred for 10 minutes at room temperature and a solution of isopropylamine (1.33 mL, 15.4 mmol, 2.2 eq) in THF (15 ml, 1 M solution) was added dropwise to the reaction mixture. The reaction flask was stirred for 3 hours. A solution of NaB(CN)H$_3$ (0.53 g, 8.4 mmol, 1.2 eq) in THF (8 mL, 1 M solution) was added slowly to the reaction mixture. MeOH (12 mL) was added slowly to the reaction mixture. The reaction mixture was stirred at room temperature for 18 hours. NaOH (~15 mL, 2M aq solution) was added slowly and the reaction mixture was stirred for 30 min. The reaction mixture was filtered on Celite® and washed with EtOAc (~15 mL). NaHCO$_3$ (aq. sat., ca 15 mL) were added to the suspension. The mixture was partitioned between the aqueous and organic layers and the aqueous phase extracted with EtOAc (3×15 mL). The combined organic phase was concentrated in vacuo. Et$_2$O was added to the oil (~8 mL). Then HCl (aq 2.0 M, ~3 mL) was added dropwise for about 5 min. The mixture was partitioned between the aqueous and Et$_2$O layers and the organic phase extracted with HCl (aq 2.0 M, 25 mL). Then CH$_2$Cl$_2$ (20 mL) was added to the combined aqueous phases and NaOH (aq saturated with brine solution, 25%) was added until the mixture became basic (pH paper, pH~14). The mixture was partitioned between the aqueous and CH$_2$Cl$_2$ layers and the aqueous phase extracted with CH$_2$Cl$_2$ (3×15 mL). The combined organic phase was dried (MgSO$_4$), filtered and concentrated in vacuo to afford the desired N-bis(4-methoxyphenyl)methyl)propan-2-amine (0.94 g, 3.3 mmol, 47%). The amine was used without further purification. $^1$H NMR (400 MHz, CDCl$_3$) $\delta_H$/ppm 7.24-7.33 (m, 4 H), 7.12 (d, J=7.8 Hz, 4 H), 4.94 (s, 1 H), 2.77 (spt, J=6.2 Hz, 1 H), 2.33 (s, 6 H), 1.30 (br. s., 1 H), 1.10 (d, J=6.4 Hz, 6 H). $^{13}$C NMR (100 MHz, CDCl$_3$) $\delta_C$/ppm 141.8 (2 C), 136.2 (2 C), 128.7-129.5 (m, 4 C), 127.2 (4 C), 63.6, 46.0, 23.2 (2 C), 21.0 (2 C). HRMS (EI) m/z calcd for C$_{18}$H$_{23}$NO$_2$ [M+H]$^+$: 285.1729, found: 285.1729. IR ($v_{max}$/cm$^{-1}$): 2960, 1510, 1468, 1379, 1365, 1167, 1021, 807, 768.

Example 36

N-(di(naphthalen-1-yl)methyl)cyclohexanamine

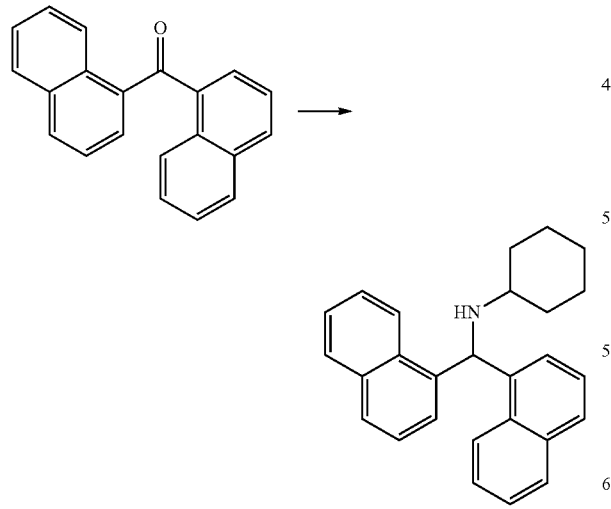

TiCl$_4$ (5.8 mL, 5.8 mmol, 1.1 eq, 1 M solution in DCM) was added slowly to an ice-bathed solution of di(naphthalen-1-yl)methanone (1.5 g, 5.3 mmol, 1.0 eq) in DCE (20 mL) in a sealed tube. The solution was stirred for 10 minutes at room temperature and then a solution of cyclohexylamine (1.7 mL, 11.7 mmol, 2.2 eq) in DCE (6 mL) was added dropwise to the reaction mixture. The reaction flask was sealed and heated under reflux (80° C.) for 3 hours. Once cooled to room temperature, NaB(CN)H$_3$ (0.67 g, 10.6 mmol, 2.0 eq) and a solution of isopropylamine (1.3 mL, 15.6 mmol, 2.2 eq) in DCE (10 mL) were added dropwise sequentially to the reaction mixture. The reaction flask was sealed and heated under reflux (90° C.) for 15 hours. The reaction mixture was allowed to cool down to room temperature and then cooled with an ice bath. NaOH (~20 mL, 2M aq solution) was added slowly and the reaction mixture was stirred for 1 hour. The reaction mixture was filtered on Celite® and washed with DCM (~20 mL). NaHCO$_3$ (aq. sat., ca 15 mL) were added to the suspension. The mixture was partitioned between the aqueous and organic layers and the aqueous phase extracted with DCM (3×15 mL). The combined organic phase was dried over MgSO$_4$, filtered and concentrated in vacuo to give an oil. Purification by two flash column chromatography (Toluene; SiO$_2$) and then (95:5 Petrol/EtOAc; SiO$_2$) of the residue gave the desired amine (1.03 g, 2.81 mmol, 53%). $^1$H NMR (400 MHz, CDCl$_3$) $\delta_H$/ppm 8.08-8.32 (m, 2 H), 7.87-7.96 (m, 2 H), 7.79 (d, J=8.1 Hz, 2 H), 7.55 (d, J=6.8 Hz, 2 H), 7.46-7.52 (m, 4 H), 7.43 (t, J=8.1 Hz, 2 H), 6.66 (s, 1 H), 2.65-2.83 (m, 1 H), 2.03-2.28 (m, 2 H), 1.69-1.85 (m, 2 H), 1.50-1.66 (m, 3 H), 1.05-1.37 (m, 4 H). $^{13}$C NMR (100 MHz, CDCl$_3$) $\delta_C$/ppm 139.2 (1 C), 134.1 (2 C), 131.4 (2 C), 128.9 (3 C), 127.6 (2 C), 126.2 (2 C), 125.6-125.8 (2 C), 125.5 (2 C), 125.4 (2 C), 123.1 (2 C), 55.4 (1 C), 55.0 (1 C), 34.1 (2 C), 26.1 (1 C), 25.2 (2 C). HRMS (ESI) m/z calcd for C$_{27}$H$_{28}$N [M+H]$^+$: 366.2216, found: 366.2205. IR ($v_{max}$/cm$^{-1}$): 3457, 3016, 2970, 1738, 1375, 1228, 776.

Example 37

N-(di(naphthalen-1-yl)methyl)propan-2-amine

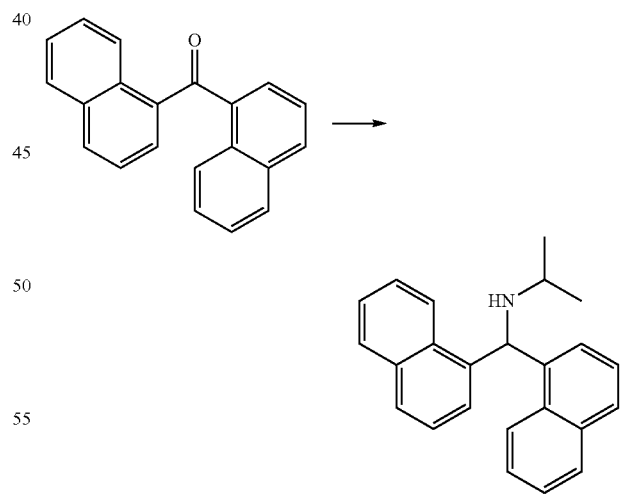

TiCl$_4$ (7.8 mL, 7.8 mmol, 1.0 eq, 1 M solution in DCM) was added slowly to an ice-bathed solution of di(naphthalen-1-yl)methanone (2.0 g, 7.1 mmol, 1.0 eq) in DCE (20 mL) in a sealed tube. The solution was stirred for 10 minutes at room temperature and then a solution of isopropylamine (1.3 mL, 15.6 mmol, 2.2 eq) in DCE (1.3 mL) was added dropwise to the reaction mixture. The reaction flask was sealed and heated under reflux (80° C.) for 4 hours. Once cooled to room temperature, NaB(CN)H$_3$ (0.53 g, 8.5 mmol, 1.2 eq) and a solution of isopropylamine (1.3 mL, 15.6 mmol, 2.2 eq) in DCE (1.3 mL) were added dropwise sequentially to the reaction mixture. The reaction flask was sealed and heated under reflux (90° C.) for 18 hours. The reaction mixture was allowed to cool down to room temperature and then cooled with an ice bath. NaOH (~40 mL, 2M aq solution) was added slowly and the reaction mixture was stirred for 1 hour. The reaction mixture was filtered on Celite® and washed with EtOAc (~50 mL). NaHCO$_3$ (aq. sat., ca 35 mL) were added to the suspension. The mixture was partitioned between the aqueous and organic layers and the aqueous phase extracted with EtOAc (3×30 mL). The combined organic phase was dried over MgSO$_4$, filtered and concentrated in vacuo to give an oil. Purification by two flash column chromatography (Toluene; SiO$_2$) and then (95:5; Petrol/EtOAc; SiO$_2$) of the residue gave the desired amine (0.364 g, 1.12 mmol, 16%) as a yellow solid. $^1$H NMR (400 MHz, CDCl$_3$) δ$_H$/ppm 7.94-8.00 (m, 2 H), 7.85 (d, J=8.1 Hz, 2 H), 7.63 (d, J=6.8 Hz, 2 H), 7.52-7.58 (m, 4 H), 7.46-7.52 (m, 2 H), 6.68 (s, 1 H), 3.22 (spt, J=6.3 Hz, 1 H), 1.65 (s, 1 H), 1.31 (d, J=7.2 Hz, 6 H). $^{13}$C NMR (100 MHz, CDCl$_3$) δ$_C$/ppm 139.0 (1 C), 134.1 (1 C), 131.4 (1 C), 128.9 (2 C), 127.6 (2 C), 126.3 (2 C), 125.5 (2 C), 125.4 (2 C), 55.6 (1 C), 47.4 (1 C), 23.3 (2 C). HRMS (ESI) m/z calcd for C$_{24}$H$_{24}$N [M+H]$^+$: 326.1888, found: 326.1903. IR (v$_{max}$/cm$^{-1}$):3457, 3016, 2970, 1738, 1375, 1228, 776.

Example 38

N-(di(naphthalen-2-yl)methyl)propan-2-amine

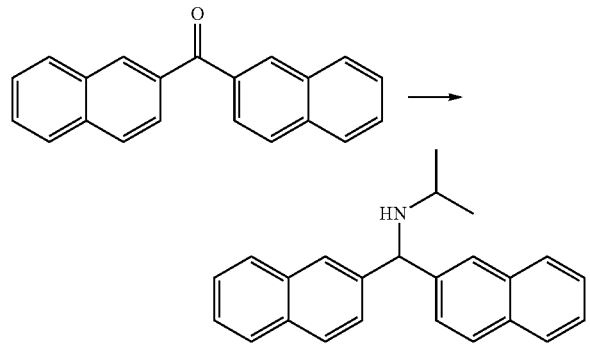

TiCl$_4$ (10.3 mL, 10.3 mmol, 1.1 eq, 1 M solution in DCM) was added slowly to an ice-bathed solution of di(naphthalen-2-yl)methanone (2.65 g, 9.38 mmol, 1.0 eq) in DCM (50 mL). The solution was stirred for 10 minutes at room temperature and then a solution of isopropylamine (1.8 mL, 20.6 mmol, 2.2 eq) in THF (10 ml, 2 M solution) was added dropwise to the reaction mixture. The reaction flask was stirred for 3 hours. A solution of NaB(CN)H$_3$ (0.71 g, 11.2 mmol, 1.2 eq) in THF (12 mL, 1 M solution) was added slowly to the reaction mixture. MeOH (17 mL) was added slowly to the reaction mixture. The reaction mixture was stirred at room temperature for 18 hours. NaOH (~25 mL, 2M aq solution) was added slowly and the reaction mixture was stirred for 30 min. The reaction mixture was filtered on Celite® and washed with EtOAc (~20 mL). NaHCO$_3$ (aq. sat., ca 15 mL) were added to the suspension. The mixture was partitioned between the aqueous and organic layers and the aqueous phase extracted with EtOAc (3×20 mL). The combined organic phase was dried over MgSO$_4$, filtered and concentrated in vacuo to give an oil. Purification by flash column chromatography (93:7; Petrol/EtOAc; SiO$_2$) gave N-(di(naphthalen-2-yl)methyl)propan-2-amine (2.24 g, 6.9 mmol, 74%) as a colourless solid. $^1$H NMR (400 MHz, CDCl$_3$) δ$_H$/ppm 8.15 (s, 2 H), 8.03 (d, J=8.1 Hz, 2 H), 7.95 (d, J=8.4 Hz, 4 H), 7.74 (dd, J=8.4, 1.5 Hz, 2 H), 7.56-7.67 (m, 4 H), 5.51 (s, 1 H), 3.06 (spt, J=6.2 Hz, 1 H), 1.72 (br. s., 1 H), 1.36 (d, J=6.2 Hz, 6 H). $^{13}$C NMR (100 MHz, CDCl$_3$) δ$_C$/ppm 141.8 (2 C), 133.4 (2 C), 132.6 (2 C), 128.2 (2 C), 127.9 (2 C), 127.6 (2 C), 126.0 (2 C), 125.9 (2 C), 125.7 (2 C), 125.6 (2 C), 64.3 (1 C), 46.2 (1 C), 23.3 (2 C). HRMS (ESI) m/z calcd for C$_{32}$H$_{52}$N [M+H]$^+$: 326.1888, found: 326.1903. IR (v$_{max}$/cm$^{-1}$): 3055, 2960, 1600, 1362, 907, 757, 734.

Example 39

Di(naphthalen-2-yl)methanol

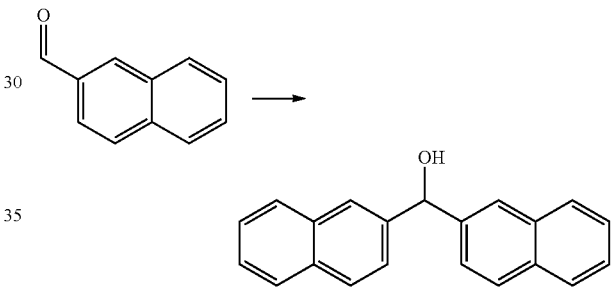

According to a modified procedure from Hsieh et al (Tetrahedron, 2009, 65(16), 3062-3068), THF (~30 mL) was added to immerse magnesium turnings (1.01 g, 41.6 mmol, 1.3 eq). The reaction was heated at 40° C. and I$_2$ (1 crystal) was added to the solution. After 10 minutes, 2-bromonaphtalene (2.17 mL, 15.65 mmol, 1.05 eq) and THF (20 mL) were added slowly to the reaction mixture. The reaction mixture was refluxed for 3 hours. Upon cooling at room temperature, 2-naphthaldehyde (5.1 g, 32.0 mmol, 1.0 eq) was added dropwise (1 drop/second) to the reaction mixture and stirred for 18 hours. H$_2$O (~30 mL), HCl (~20 mL, 2 M) and Et$_2$O (~40 mL) were added to the reaction mixture, which was stirred at room temperature for 20 minutes. The mixture was partitioned between the aqueous and organic layers and the aqueous phase extracted with Et$_2$O (3×50 mL). The combined organic phase was dried over MgSO$_4$, filtered and concentrated in vacuo to give di(naphthalen-2-yl)methanol (9.0 g, 31.6 mmol, 99%) as a colourless solid. The molecule was used without further purification. $^1$H NMR (400 MHz, CDCl$_3$) δ$_H$/ppm 7.95 (s, 2 H), 7.81-7.90 (m, 5 H), 7.80 (s, 1 H), 7.48-7.55 (m, 5 H), 7.47 (d, J=1.7 Hz, 1 H), 6.15 (s, 1 H), 2.59 (s, 1 H). $^{13}$C NMR (100 MHz, CDCl$_3$) δ$_C$/ppm 140.9 (2 C), 133.2 (2 C), 132.9 (2 C), 128.4 (2 C), 128.1 (2 C), 127.7 (2 C), 126.2 (2 C), 126.0 (2 C), 125.2 (2 C), 124.9 (2 C), 76.4. HRMS (ESI) m/z calcd for C$_{21}$H$_{16}$NaO [M+Na]$^+$: 307.1093, found: 307.1091. IR (v$_{max}$/cm$^{-1}$): 3450, 2970, 1739, 1436, 1217, 897, 757.

Example 40

Di(naphthalen-2-yl)methanone

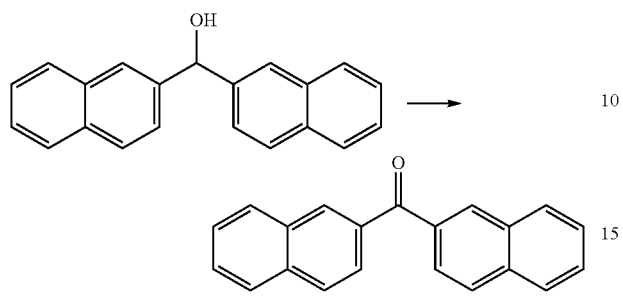

According to a modified procedure from Azuma et al (Tetrahedron, 2013, 69(6), 1694-1699), $MnO_2$ (8.4 g, 96.7 mmol, 10 eq) was added to a stirring solution of di(naphthalen-2-yl)methanol (2.75 g, 9.68 mmol, 1.0 eq) in DCM (20 mL) at room temperature. The solution was stirred for 24 hours. The reaction mixture was then filtered over Celite® and concentrated in vacuo to give the desired di(naphthalen-2-yl)methanone (2.70 g, 9.56 mmol, 99%) as colourless solid. The molecule was used without further purification. $^1$H NMR (400 MHz, $CDCl_3$) $\delta_H$/ppm 8.34 (s, 2 H), 8.00-8.03 (m, 4 H), 7.95 (apparent t, J=7.2 Hz, 4 H), 7.65 (apparent td, J=7.6, 1.2 Hz, 2 H), 7.58 (apparent td, J=7.6, 1.2 Hz, 2 H). $^{13}$C NMR (100 MHz, $CDCl_3$) $\delta_C$/ppm 196.8 (1 C), 135.3 (2 C), 135.2 (2 C), 132.3 (2 C), 131.8 (2 C), 127.8 (4 C), 126.8 (4 C), 125.9 (4 C). MS (ESI) [M+Na]$^+$: 305.1 (100). IR ($v_{max}$/cm$^{-1}$): 2915, 1653, 1379, 1334, 1194, 763.

Example 41

Bis(3,5-dimethylphenyl)methanol

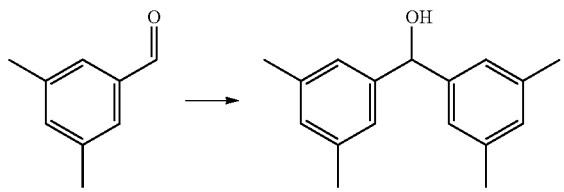

According to a modified procedure from Hsieh et al (supra), THF (~10 mL) was added to immerse magnesium turnings (471 mg, 119.4 mmol, 1.3 eq). The reaction was heated at 40° C. and $I_2$ (1 crystal) was added to the solution. After 10 minute, 1-bromo-3,5-dimethylbenzene (2.17 mL, 15.65 mmol, 1.05 eq) and THF (5 mL) was added slowly to the reaction mixture. The reaction mixture was refluxed for 4 hours. Upon cooling at room temperature, 3,5-dimethylbenzaldehyde (2.0 g, 14.91 mmol) was added dropwise (1 drop/second) to the reaction mixture and stirred for 18 hours. $H_2O$ (~10 mL), HCl (~5 mL, 2 M) and $Et_2O$ (~10 mL) were added successfully to the reaction mixture which was stirred at room temperature for 20 minutes. The mixture was partitioned between the aqueous and organic layers and the aqueous phase extracted with $Et_2O$ (3×15 mL). The combined organic phase was dried over $MgSO_4$, filtered and concentrated in vacuo to give bis(3,5-dimethylphenyl)methanol (3.7 g, 15.35 mmol, 98%) as a colourless solid. The molecule was used without further purification. $^1$H NMR (400 MHz, $CDCl_3$) $\delta_H$/ppm 7.01 (s, 4 H), 6.91 (s, 2 H), 5.71 (s, 1 H), 2.31 (s, 12 H), 1.59 (br. s., 1 H). $^{13}$C NMR (100 MHz, $CDCl_3$) $\delta_C$/ppm 143.9 (2 C), 137.9 (2 C), 129.1 (2 C), 124.2 (2 C), 76.3 (1 C), 21.3 (2 C). HRMS (ESI) m/z calcd for $C_{17}H_{20}NaO$ [M+Na]$^+$: 263.1406, found: 263.1408. IR ($v_{max}$/cm$^{-1}$): 2970, 1750, 1373, 1215, 1056, 896, 750, 702.

Example 42

Bis(3,5-dimethylphenyl)methanone

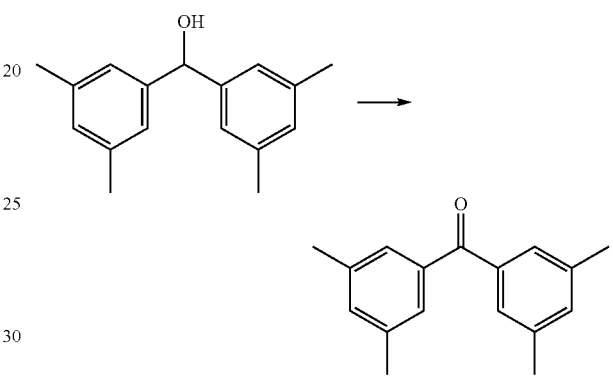

According to a modified procedure from Azuma et al (supra), $MnO_2$ (8.0 g, 92.3 mmol, 6 eq) was added to a stirring solution of bis(3,5-dimethylphenyl)methanol (3.7 g, 15.3 mmol, 1.0 eq) in DCM (30 mL) at room temperature. The solution was stirred for 18 hours. $MnO_2$ (8.0 g, 92.3 mmol, 6 eq) was added to the reaction mixture and the reaction mixture was stirred for another 24 hours. The reaction mixture was then filtered over Celite® and concentrated in vacuo to give the desired bis(3,5-dimethylphenyl)methanone (3.5 g, 14.7 mmol, 96%) as colourless solid. The molecule was used without further purification. $^1$H NMR (400 MHz, $CDCl_3$) $\delta_H$/ppm 7.39 (s, 4 H), 7.22 (s, 2 H), 2.38 (s, 12 H). $^{13}$C NMR (100 MHz, $CDCl_3$) $\delta_C$/ppm 197.6 (1 C), 138.0 (2 C), 137.8 (4 C), 133.9 (2 C), 127.7 (4 C), 21.2 (4 C). HRMS (ESI) m/z calcd for $C_{17}H_{18}NaO$ [M+Na]$^+$: 261.1250, found: 261.1244. IR ($v_{max}$/cm$^{-1}$): 2915, 1649, 1599, 1379, 1320, 1192, 763.

Example 43

N-(bis(3,5-di-tert-butylphenyl)methyl)propan-2-amine

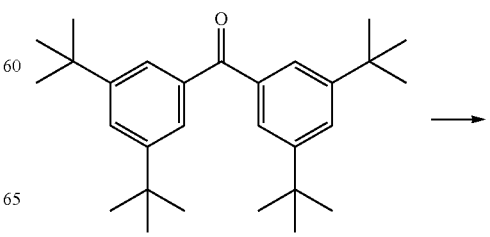

-continued

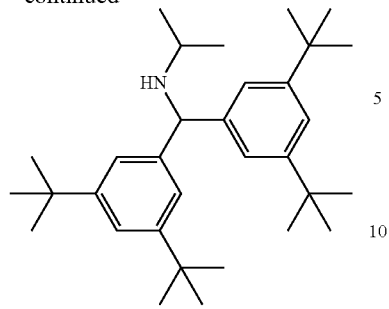

-continued

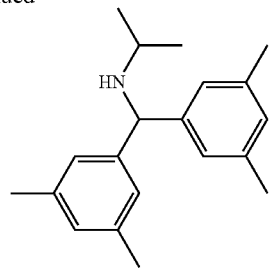

TiCl$_4$ (6.9 mL, 6.90 mmol, 1.1 eq, 1 M solution in DCM) was added slowly to an ice-bathed solution of bis(3,5-di-tert-butylphenyl)methanone (2.55 g, 6.27 mmol, 1.0 eq) in DCM (35 mL). The solution was stirred for 10 minutes at room temperature and then a solution of isopropylamine (1.2 mL, 13.8 mmol, 2.2 eq) in THF (7 ml, 2 M solution) was added dropwise to the reaction mixture. The reaction flask was stirred for 3 hours. A solution of NaB(CN)H$_3$ (0.47 g, 7.5 mmol, 1.2 eq) in THF (7.5 mL, 1 M solution) was added slowly to the reaction mixture. MeOH (11.4 mL) was added slowly to the reaction mixture. The reaction mixture was stirred at room temperature for 18 hours. NaOH (~20 mL, 2M aq solution) was added slowly and the reaction mixture was stirred for 30 min. The reaction mixture was filtered on Celite® and washed with DCM (~20 mL). NaHCO$_3$ (aq. sat., ca 15 mL) were added to the suspension. The mixture was partitioned between the aqueous and organic layers and the aqueous phase extracted with DCM (3×10 mL). The combined organic phase was dried over MgSO$_4$, filtered and concentrated in vacuo to give an oil. Petrol (~25 mL) and Et2O (~15 mL) were added to the crude mixture. Concentrated HCl (~5 mL, 37% w/v solution) was added. The mixture was left and crystals formed after 1 hour. The reaction flask was then stored at −20° C. overnight. The reaction mixture was filtered and washed with cold petrol. The crystals were collected and dried under high vacuum to give the desired N-(bis(3,5-di-tert-butylphenyl)methyl)propan-2-amine (0.51 g, 1.11 mmol, 18%). $^1$H NMR (400 MHz, CDCl$_3$) $\delta_H$/ppm 7.31 (br. s., 4 H), 7.29 (br. s., 2 H), 4.98 (br. s., 1 H), 2.68-2.86 (m, 1 H), 1.37-1.40 (m, 1 H), 1.35 (br. s, 36 H), 1.14 (d, J=6.2 Hz, 6 H). $^{13}$C NMR (100 MHz, CDCl$_3$) $\delta_C$/ppm 150.3 (4 C), 143.9 (2 C), 121.7 (4 C), 120.5 (2 C), 65.7 (1 C), 46.2 (1 C), 34.8 (2 C), 31.5 (12 C), 23.3 (2 C). HRMS (ESI) m/z calcd for C$_{32}$H$_{52}$N [M+H]$^+$: 450.4092, found: 450.4094. IR (v$_{max}$/cm$^{-1}$): 2960, 2867, 1598, 1477, 1393, 1248, 876, 728.

Example 44

N-(bis(3,5-dimethylphenyl)methyl)propan-2-amine

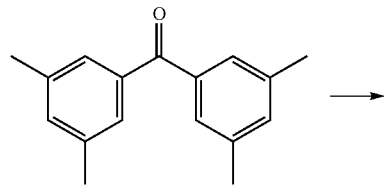

TiCl$_4$ (16.2 mL, 16.2 mmol, 1.1 eq, 1 M solution in DCM) was added slowly to an ice-bathed solution of bis(3,5-dimethylphenyl)methanone (3.5 g, 14.7 mmol, 1.0 eq) in DCM (80 mL). The solution was stirred for 10 minutes at room temperature and then a solution of isopropylamine (2.8 mL, 32.3 mmol, 2.2 eq) in THF (17 ml, 2 M solution) was added dropwise to the reaction mixture. The reaction flask was stirred for 3 hours. A solution of NaB(CN)H$_3$ (1.1 g, 17.6 mmol, 1.2 eq) in THF (18 mL, 1 M solution) was added slowly to the reaction mixture. MeOH (26 mL) was added slowly to the reaction mixture. The reaction mixture was stirred at room temperature for 18 hours. NaOH (~30 mL, 2M aq solution) was added slowly and the reaction mixture was stirred for 30 min. The reaction mixture was filtered on Celite® and washed with EtOAc (~20 mL). NaHCO$_3$ (aq. sat., ca 15 mL) were added to the suspension. The mixture was partitioned between the aqueous and organic layers and the aqueous phase extracted with EtOAc (3×10 mL). The combined organic phase was dried over MgSO$_4$, filtered and concentrated in vacuo to give an oil. Purification by flash column chromatography (19:1; Petrol/EtOAc; SiO$_2$) gave the desired amine (2.44 g, 8.6 mmol, 59%) as a white solid. $^1$H NMR (400 MHz, CDCl$_3$) $\delta_H$/ppm 7.00 (s, 4 H), 6.85 (s, 2 H), 4.83 (s, 1 H), 2.75 (dt, J=12.5, 6.3 Hz, 1 H), 2.30 (s, 12 H), 1.24-1.39 (m, 1 H), 1.10 (d, J=6.3 Hz, 6 H). $^{13}$C NMR (100 MHz, CDCl$_3$) $\delta_C$/ppm 144.6 (2 C), 137.8 (4 C), 128.4 (2 C), 125.0 (4 C), 64.2 (1 C), 46.1 (1 C), 23.2 (2 C), 21.4 (4 C). HRMS (ESI) m/z calcd for C$_{20}$H$_{28}$N [M+H]$^+$: 282.2225, found: 282.2216. IR (v$_{max}$/cm$^{-1}$): 2956, 1598, 1469, 1375, 1166, 861, 740.

Example 45

Bis(2-methoxyphenyl)methanol

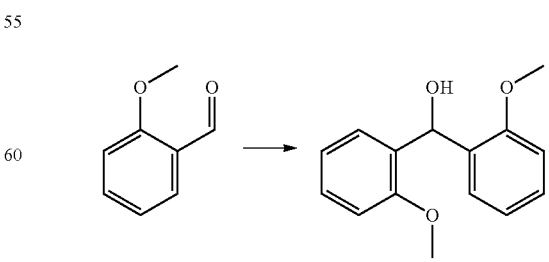

According to a modified procedure from Diederich et al (J. Am. Chem. Soc., 1988, 110 (6), 1679-1690), THF (~30 mL) was added to immerse magnesium turnings (1.1 g, 38.5 mmol, 1.05 eq). The reaction was heated at 40° C. and I$_2$ (1 crystal) was added to the solution. After 10 minutes, 1-bromo-2-methoxybenzene (4.8 mL, 47.7 mmol, 1.3 eq) and THF (15 mL) was added slowly to the reaction mixture. The reaction mixture was refluxed for 4 hours. Upon cooling at room temperature, 2-methoxybenzaldehyde (4.4 mL, 36.7 mmol, 1.0 eq) was added dropwise (1 drop/second) to the reaction mixture and stirred for 18 hours. H$_2$O (~40 mL), HCl (~25 mL, 2 M) and Et$_2$O (~40 mL) were added successively to the reaction mixture which was stirred at room temperature for 20 minutes. The mixture was partitioned between the aqueous and organic layers and the aqueous phase extracted with Et$_2$O (3×50 mL). The combined organic phase was dried over MgSO$_4$, filtered and concentrated in vacuo to give bis(2-methoxyphenyl)methanol (8.5 g, 34.7 mmol, 94%) as a colourless solid. The molecule was used without further purification. $^1$H NMR (400 MHz, CDCl$_3$) $\delta_H$/ppm 7.27-7.31 (m, 2 H), 7.23-7.27 (m, 2 H), 6.95 (td, J=7.5, 0.9 Hz, 2 H), 6.91 (d, J=8.3 Hz, 2 H), 6.37 (d, J=5.4 Hz, 1 H), 3.84 (s, 6 H), 3.57 (dd, J=5.1, 0.7 Hz, 1 H). $^{13}$C NMR (100 MHz, CDCl$_3$) $\delta_C$/ppm 156.8 (2 C), 130.9 (2 C), 128.4 (2 C), 127.8 (2 C), 120.5 (2 C), 110.4 (2 C), 67.4 (1 C), 55.4 (2 C). HRMS (ESI) m/z calcd for C$_{15}$H$_{16}$NaC$_3$ [M+Na]$^+$: 267.0992, found: 267.0999. IR ($v_{max}$/cm$^{-1}$): 2970, 1759, 1342, 1204.

Example 46

Bis(2-methoxyphenyl)methanone

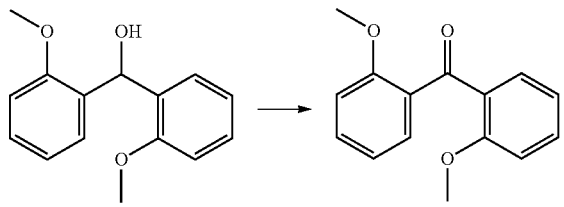 [SMILES: COc1ccccc1C(O)c1ccccc1OC ; COc1ccccc1C(=O)c1ccccc1OC]

According to a modified procedure from Diederich et al (supra), MnO$_2$ (7.6 g, 88.0 mmol, 5 eq) was added to a stirring solution of bis(2-methoxyphenyl)methanol (4.2 g, 17.4 mmol, 1.0 eq) in DCM (50 mL) at room temperature. The solution was stirred for 18 hours. MnO$_2$ (7.6 g, 88.0 mmol, 5 eq) was added to the reaction mixture and the reaction mixture was stirred for another 24 hours. The reaction mixture was then filtered over Celite® and concentrated in vacuo to give the desired bis(2-methoxyphenyl)methanone (3.3 g, 13.7 mmol, 79%) as a colourless solid. The molecule was used without further purification. $^1$H NMR (400 MHz, CDCl$_3$) $\delta_H$/ppm 7.52 (dd, J=7.6, 1.7 Hz, 2 H), 7.44 (ddd, J=8.3, 7.4, 2.0 Hz, 2 H), 6.99 (td, J=7.5, 0.7 Hz, 2 H), 6.92 (d, J=8.3 Hz, 2 H), 3.67 (s, 6 H). $^{13}$C NMR (100 MHz, CDCl$_3$) $\delta_C$/ppm 195.3, 158.2 (2 C), 132.5 (2 C), 130.3 (2 C), 130.2 (2 C), 120.3 (2 C), 111.4 (2 C), 55.6 (2 C). HRMS (ESI) m/z calcd for C$_{15}$H$_{14}$NaO [M+Na]$^+$: 265.0835, found: 265.0836. IR ($v_{max}$/cm$^{-1}$): 2970, 1730, 1597, 1369, 1250, 1023, 751.

Example 47

N-(bis(2-methoxyphenyl)methyl)propan-2-amine

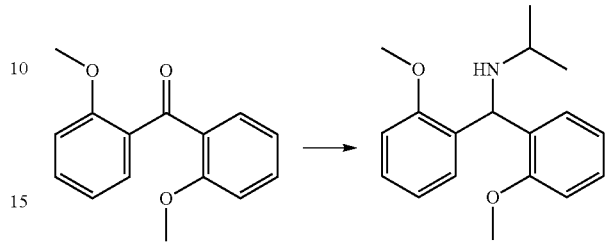

According to a modified procedure from Hampton et al (supra), TiCl$_4$ (15.2 mL, 15.1 mmol, 1.1 eq, 1 M solution in DCM) was added slowly to an ice-bathed solution of bis(2-methoxyphenyl)methanone (3.33 g, 13.8 mmol, 1.0 eq) in DCM (40 mL). The solution was stirred for 10 minutes at room temperature and then a solution of isopropylamine (3.5 mL, 41.2 mmol, 3.0 eq) in THF (20 ml, 2 M solution) was added dropwise to the reaction mixture. The reaction flask was stirred for 6 hours. A solution of NaB(CN)H$_3$ (4.32 g, 68.7 mmol, 5.0 eq) in THF (68 mL, 1 M solution) was added slowly to the reaction mixture. MeOH (24 mL) was added slowly to the reaction mixture. The reaction mixture was stirred at room temperature for 18 hours. NaOH (_50 mL, 2M aq solution) was added slowly and the reaction mixture was stirred for 30 min. The reaction mixture was filtered on Celite® and washed with Et$_2$O (~70 mL). NaHCO$_3$ (aq. sat., ca 50 mL) were added to the suspension. The mixture was partitioned between the aqueous and organic layers and the aqueous phase extracted with Et$_2$O (3×50 mL). The combined organic phase was dried over MgSO$_4$, filtered and concentrated in vacuo to give an oil. Et$_2$O (~50 mL) were added to the crude mixture. Concentrated HCl (~5 mL, 37% w/v solution) was added. The mixture was left and crystals formed after 5 min.

The mixture was partitioned between the aqueous and Et$_2$O layers and the organic phase extracted with HCl (aq 2.0 M, 3×30 mL). Then CH$_2$Cl$_2$ (20 mL) was added to the combined aqueous phases and NaOH (aq saturated with brine solution, 25%) was added until the mixture became basic (pH paper, pH~14). The mixture was partitioned between the aqueous and CH$_2$Cl$_2$ layers and the aqueous phase extracted with CH$_2$Cl$_2$ (3×50 mL). The combined organic phase was dried (MgSO$_4$), filtered and concentrated in vacuo to afford the desired N-(bis(2-methoxyphenyl)methyl)propan-2-amine (2.14 g, 7.4 mmol, 54%). The amine was used without further purification.

$^1$H NMR (400 MHz, CDCl$_3$) $\delta_H$/ppm 7.37 (d, J=7.3 Hz, 2 H), 7.20 (td, J=7.7, 1.5 Hz, 2 H), 6.93 (t, J=7.5 Hz, 2 H), 6.85 (d, J=8.3 Hz, 2 H), 5.63 (s, 1 H), 3.80 (s, 6 H), 2.76 (spt, J=6.2 Hz, 1 H), 1.86-2.25 (m, 1 H), 1.12 (d, J=6.1 Hz, 6 H). $^{13}$C NMR (100 MHz, CDCl$_3$) $\delta_C$/ppm 157.2 (2 C), 131.8 (2 C), 128.5 (2 C), 127.4 (2 C), 120.3 (2 C), 110.7 (2 C), 55.4 (2 C), 52.5, 46.2, 23.1 (2 C). HRMS (ESI) m/z calcd for C$_{18}$H$_{24}$NO$_2$[M+H]$^+$: 286.1802, found: 286.1804. IR ($v_{max}$/cm$^{-1}$): 2950, 1771, 1709, 1598, 1380, 1351, 1229.

Example 48

(R)—N-(bis(3,5-bis(trifluoromethyl)phenyl)methyl)-N-isopropyldi-naphtho[2,1-d:1',2'-f][1,3,2]dioxaphosphepin-4-amine

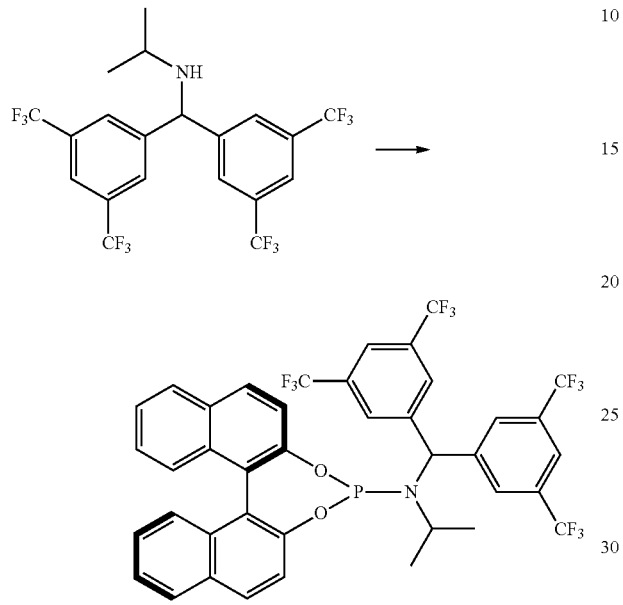

Triethylamine (1.23 mL, 8.81 mmol, 5.0 eq.) was added dropwise to a stirred ice-cooled solution of $PCl_3$ (0.14 mL, 1.61 mmol, 1.1 eq.) in $CH_2Cl_2$ (11 mL). The ice bath was removed and the solution left to warm to room temperature before N-(bis(3,5-bis(trifluoromethyl)phenyl)methyl)propan-2-amine (730 mg, 1.47 mmol, 1.0 eq.) was added to the stirring solution. After 5 additional hours of stirring, (R)-binaphthol (546 mg, 1.90 mmol, 1.3 eq.) was added to the suspension and the subsequent mixture was left to stir for an additional 18 h. The solution was then filtered on a small pad of silica and Celite® and rinsed with $CH_2Cl_2$ (~20 mL). The resulting solution was concentrated under reduced pressure to afford a yellow residue. After flash columns chromatography (Petrol: $CH_2Cl_2$: $Et_2O$; 4.3:0.3:0.3: $SiO_2$) and (Petrol: $CH_2Cl_2$: Toluene; 4.2:0.6:0.6: $SiO_2$), the ligand was obtained as a crystalline white solid (452 mg, 0.56 mmol, 38%). $^1H$ NMR (500 MHz, $CD_2Cl_2$) δ ppm 8.00 (d, J=8.8 Hz, 1 H), 7.96 (d, J=12.0 Hz, 1 H), 7.86-7.94 (m, 4 H), 7.74-7.84 (m, 3 H), 7.39-7.51 (m, 3 H), 7.32-7.38 (m, 1 H), 7.11-7.30 (m, 5 H), 5.94 (d, J=15.8 Hz, 1 H), 3.58 (dq, J=12.8, 6.4 Hz, 1 H), 1.19 (d, J=6.6 Hz, 3 H), 0.95 (d, J=6.6 Hz, 3 H). $^{13}C$ NMR (125 MHz, $CD_2Cl_2$) δ ppm 149.9 (d, J=7.4 Hz), 149.7, 145.2 (d, J=4.6 Hz), 145.2, 133.2, 132.8, 132.7, 132.5, 132.4, 132.3, 132.2, 131.4, 131.3, 130.4, 129.7 (2 C), 129.5 (2 C), 129.0, 128.9, 128.7, 127.5, 127.3, 126.8, 126.8, 125.7, 125.4, 125.0 (d, J=4.6 Hz), 124.2 (d, J=5.5 Hz), 122.7, 122.6, 121.8, 60.1 (d, J=23.0 Hz), 48.0, 23.4 (2 C). $^{31}P$ NMR (200 MHz, $CD_2Cl_2$) δ ppm 147.96 (s, 1P). $^{19}F$ NMR (380 MHz, $CDCl_3$) δ ppm −62.8 (s, 6 F), −62.9 (s, 6 F). HRMS (EI) m/z calcd for $C_{40}H_{26}F_{12}NO_2P$ [M−iPr]⁺: 811.1510, found: 811.1501. $[α]^{20}_{589}$=−130.93 (c 1.08, $CHCl_3$). IR ($v_{max}$/cm⁻¹): 1372, 1279, 1174, 1136, 949, 822.

Example 49

(R)—N-(bis(3,5-di-tert-butylphenyl)methyl)-N-isopropyldinaphtho[2,1-d:1',2'-f][1,3,2]dioxaphosphepin-4-amine

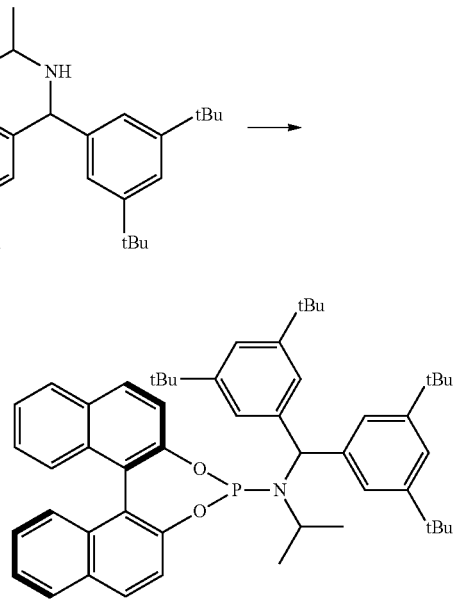

Triethylamine (1.00 mL, 7.33 mmol, 5.0 eq.) was added dropwise to a stirred ice-cooled solution of $PCl_3$ (0.12 mL, 1.23 mmol, 1.0 eq.) in $CH_2Cl_2$ (9 mL). The ice bath was removed and the solution left to warm to room temperature before N-(bis(3,5-di-tert-butylphenyl)methyl)propan-2-amine (553 mg, 1.23 mmol, 1.0 eq.) was added to the stirring solution. After 5 additional hours of stirring, (R)-binaphthol (458 mg, 1.23 mmol, 1.0 eq.) was added to the suspension and the subsequent mixture was left to stir for an additional 18 h. The solution was then filtered on a small pad of silica and Celite® and rinsed with $CH_2Cl_2$ (~20 mL). The resulting solution was concentrated under reduced pressure to afford a yellow residue. After flash columns chromatography (Petrol: $CH_2Cl_2$: $Et_3N$; 79.5:20:0.5: $SiO_2$) and (Petrol: $CH_2Cl_2$: $Et_3N$; 85:15:0.03: $SiO_2$), the ligand was obtained as a crystalline white solid (472 mg, 0.61 mmol, 50%). $^1H$ NMR (500 MHz, $CDCl_3$) δ ppm 7.86-7.95 (m, 3 H), 7.82 (d, J=8.8 Hz, 1 H), 7.33-7.45 (m, 8 H), 7.25-7.33 (m, 3 H), 7.19-7.24 (m, 1 H), 7.14 (d, J=0.9 Hz, 2 H), 5.64 (d, J=18.9 Hz, 1 H), 3.54 (dq, J=9.8, 6.5 Hz, 1 H), 1.37 (s, 18 H), 1.31-1.35 (m, 18 H), 1.00-1.08 (m, 6 H). $^{13}C$ NMR (125 MHz, $CDCl_3$) δ ppm 150.8 (d, J=6.5 Hz), 150.5 (2 C), 150.2 (2 C), 150.1, 143.4, 142.7, 132.8 (2 C), 132.7 (2 C), 131.3, 130.4, 130.1, 129.3, 128.2, 128.2, 127.13, 127.11, 125.9, 125.8, 124.6, 124.2, 124.0 (d, J=5.5 Hz), 123.3 (d, J=4.6 Hz), 123.2, 122.3, 122.3, 121.7, 120.2, 120.1, 61.5 (d, J=27.0 Hz), 46.8, 35.0 (2 C), 34.9 (2 C), 31.6 (6 C), 31.5 (6C), 22.9, 22.9. $^{31}P$ NMR (200 MHz, $CDCl_3$) δ ppm 152.00 (s, 1P). HRMS (EI) m/z calcd for $C_{47}H_{38}NO_2P$ [M−iPr]⁺: 720.3970, found: 720.4001. $[α]^{20}_{589}$=−80.83 (c 1.09, $CHCl_3$). IR ($v_{max}$/cm⁻¹): 2964, 1739, 1593, 1463, 1367, 1231, 750.

Example 50

(R)—N-(bis(3,5-dimethylphenyl)methyl)-N-isopropyldinaphtho[2,1-d:1',2'-f][1,3,2]dioxaphosphepin-4-amine

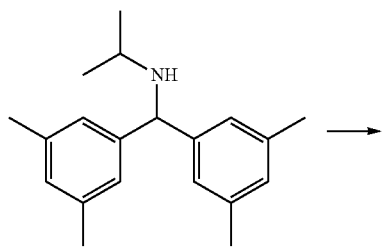

Triethylamine (2.50 mL, 17.79 mmol, 5.0 eq.) was added dropwise to a stirred ice-cooled solution of PCl$_3$ (0.31 mL, 3.55 mmol, 1.0 eq.) in CH$_2$Cl$_2$ (26 mL). The ice bath was removed and the solution left to warm to room temperature before N-(bis(3,5-dimethylphenyl)methyl)propan-2-amine (1.0 g, 3.55 mmol, 1.0 eq.) was added to the stirring solution. After 5 additional hours of stirring, (R)-binaphthol (1.02 g, 3.55 mmol, 1.0 eq.) was added to the suspension and the subsequent mixture was left to stir for an additional 18 h. The solution was then filtered on a small pad of silica and Celite® and rinsed with CH$_2$Cl$_2$ (~30 mL). The resulting solution was concentrated under reduced pressure to afford a yellow residue. After flash column chromatography (Petrol: CH$_2$Cl$_2$: Et$_3$N; 79:20:1: SiO$_2$), the ligand was obtained as a crystalline white solid (1.53 g, 2.57 mmol, 73%). $^1$H NMR (500 MHz, CDCl$_3$) δ ppm 7.98 (d, J=8.8 Hz, 1 H), 7.95 (t, J=7.4 Hz, 2 H), 7.89 (d, J=8.8 Hz, 1 H), 7.39-7.50 (m, 5 H), 7.30-7.37 (m, 2 H), 7.24-7.30 (m, 1 H), 7.16 (s, 2 H), 7.01 (s, 3 H), 6.98 (s, 1 H), 5.62 (d, J=18.3 Hz, 1 H), 3.64 (br. d, J=5.0 Hz, 1 H), 2.43 (s, 6 H), 2.41 (s, 6 H), 1.11 (d, J=6.3 Hz, 3 H), 1.03 (d, J=6.3 Hz, 3 H). $^{13}$C NMR (125 MHz, CDCl$_3$) δ ppm 150.6 (d, J=7.4 Hz), 150.0, 143.7, 143.7, 143.7, 137.6, 137.5, 132.8 (d, J=9.2 Hz), 131.3, 130.5, 130.2, 129.4, 128.6 (3 C), 128.3, 128.2, 127.2, 127.1, 126.8, 126.8 (3 C), 126.8, 125.9, 125.8, 124.7, 124.3, 124.1 (d, J=4.6 Hz), 122.5, 122.2, 121.8, 60.6 (d, J=26.0 Hz), 46.7, 23.1, 22.9, 21.6 (4 C). $^{31}$P NMR (200 MHz, CDCl$_3$) δ ppm 151.05 (s, 1P). HRMS (EI) m/z calcd for C$_{40}$H$_{38}$NO$_2$P [M]$^+$: 595.2640, found: 595.2632. [α]$^{20}_{589}$=−122.04 (c 1.55, CHCl$_3$). IR (ν$_{max}$/cm$^{-1}$): 2960, 2100, 11789, 1380, 1229, 1213.

Example 51

(R)—N-cyclohexyl-N-(di(naphthalen-1-yl)methyl)dinaphtho[2,1-d:1',2'-f][1,3,2]dioxaphosphepin-4-amine

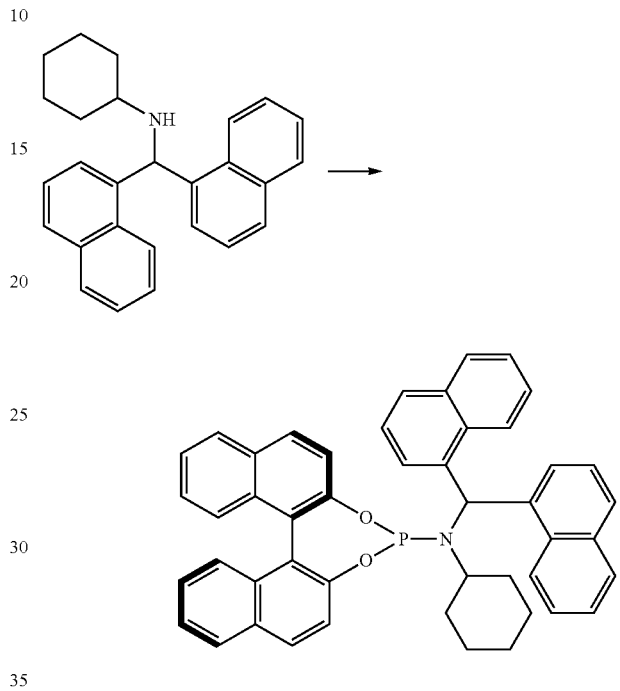

Triethylamine (1.96 mL, 14.10 mmol, 5.0 eq.) was added dropwise to a stirred ice-cooled solution of PCl$_3$ (0.25 mL, 2.80 mmol, 1.0 eq.) in CH$_2$Cl$_2$ (20 mL). The ice bath was removed and the solution left to warm to room temperature before N-(di(naphthalen-1-yl)methyl)cyclohexanamine (1.03 g, 2.80 mmol, 1.0 eq.) was added to the stirring solution. After 5 additional hours of stirring, (R)-binaphthol (806 mg, 2.80 mmol, 1.0 eq.) was added to the suspension and the subsequent mixture was left to stir for an additional 18 h. The solution was then filtered on a small pad of silica and Celite® and rinsed with CH$_2$Cl$_2$ (~35 mL). The resulting solution was concentrated under reduced pressure to afford a yellow residue. After flash column chromatography (Petrol: CH$_2$Cl$_2$: Et$_3$N; 79:20:1: SiO$_2$), the ligand was obtained as a crystalline white solid (415 mg, 0.61 mmol, 22%). $^1$H NMR (500 MHz, CDCl$_3$) δ ppm 8.41 (br. s., 1 H), 7.90-8.02 (m, 2 H), 7.72-7.89 (m, 7 H), 7.31-7.61 (m, 11 H), 7.11-7.29 (m, 7 H), 3.23 (br. s., 1 H), 1.99 (br. s., 1 H), 1.10-1.77 (m, 6 H), 0.74 (d, J=11.0 Hz, 1 H), 0.38-0.63 (m, 2 H). $^{13}$C NMR (125 MHz, CDCl$_3$) δ ppm 150.6, 150.1, 134.6, 134.4, 133.2, 132.9, 131.7, 131.4, 130.6, 130.5, 129.6, 129.4 (2 C), 129.2, 128.9 (2 C), 128.7 (2 C), 128.6, 128.5 (2 C), 127.4 (2 C), 127.3, 126.6 (2 C), 126.3 (2 C), 126.2, 126.04, 126.01 (2 C), 125.4, 125.4, 125.0, 124.7, 124.1, 123.8, 122.7, 122.4, 57.5, 55.8, 26.8 (3 C), 25.6 (2 C). $^{31}$P NMR (200 MHz, CDCl$_3$) δ ppm 148.95 (s, 1P). HRMS (EI) m/z calcd for C$_{47}$H$_{38}$NO$_2$P [M]$^+$: 679.2640, found: 679.2650. [α]$^{20}_{589}$=−79.63 (c 1.05, CHCl$_3$). IR (ν$_{max}$/cm$^{-1}$): 2930, 1730, 1420, 1350, 1213, 750.

Example 52

(R)—N-(di(naphthalen-1-yl)methyl)-N-isopropyl-dinaphtho[2,1-d:1',2'-f][1,3,2]-dioxaphosphepin-4-amine

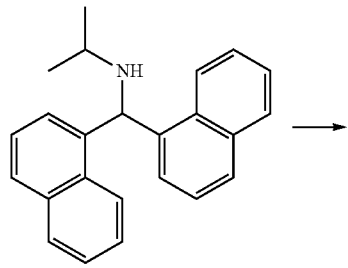

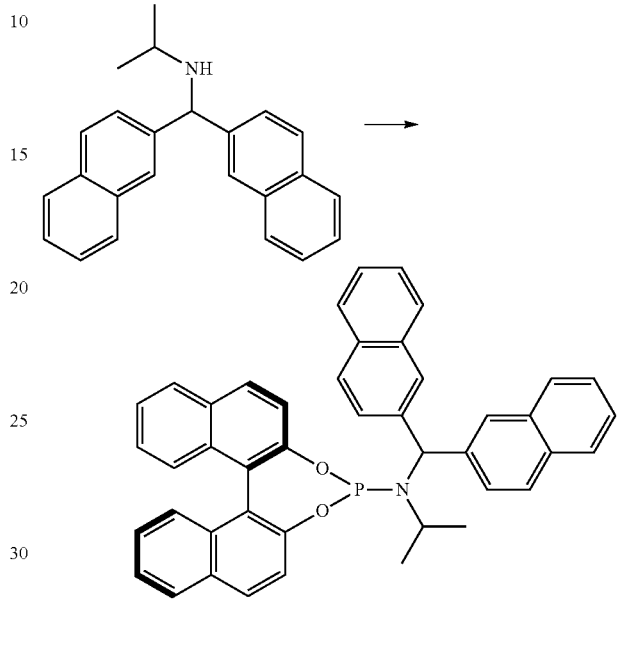

Triethylamine (0.78 mL, 5.68 mmol, 5.0 eq.) was added dropwise to a stirred ice-cooled solution of $PCl_3$ (0.10 mL, 1.12 mmol, 1.0 eq.) in $CH_2Cl_2$ (8 mL). The ice bath was removed and the solution left to warm to room temperature before N-(di(naphthalen-1-yl)methyl)propan-2-amine (365 mg, 1.12 mmol, 1.0 eq.) was added to the stirring solution. After 5 additional hours of stirring, (R)-binaphthol (321 mg, 1.12 mmol, 1.0 eq.) was added to the suspension and the subsequent mixture was left to stir for an additional 15 h. The solution was then filtered on a small pad of silica and Celite® and rinsed with $CH_2Cl_2$ (~30 mL). The resulting solution was concentrated under reduced pressure to afford a yellow residue. After flash column chromatography (Petrol: $CH_2Cl_2$: $Et_3N$; 77:12:1: $SiO_2$), the ligand was obtained as a crystalline white solid (283 mg, 0.44 mmol, 39%). $^1H$ NMR (500 MHz, $CDCl_3$) δ ppm 8.39 (br. s., 1 H), 7.61-7.98 (m, 9 H), 7.31-7.59 (m, 10 H), 6.97-7.31 (m, 7 H), 3.81 (d, J=5.7 Hz, 1 H), 1.10-1.37 (m, 3 H), 0.94 (br. s., 3 H). $^{13}C$ NMR (125 MHz, $CDCl_3$) δ ppm 150.7, 150.1, 138.9, 138.0, 134.6, 134.4, 133.2, 133.0, 131.7, 131.4, 130.7, 130.6, 129.6, 129.4, 129.2, 129.1, 128.9, 128.8, 128.6, 128.6, 127.5, 127.4, 126.7, 126.6, 126.3, 126.13, 126.09, 126.0, 125.5 (4 C), 125.1, 124.6, 124.5 (d, J=5.5 Hz), 124.0, 123.8, 122.7, 122.6, 121.9, 55.1 (d, J=26.0 Hz), 48.5, 24.6, 23.6. $^{31}P$ NMR (200 MHz, $CDCl_3$) δ ppm 148.61 (s, 1P). HRMS (EI) m/z calcd for $C_{44}H_{34}NO_2P$ [M]$^+$: 639.2327, found: 639.2354. $[\alpha]^{20}_{589}$=−79.63 (c 1.05, $CHCl_3$). IR ($v_{max}$/cm$^{-1}$): 2970, 1739, 1368, 1229, 1216.

Example 53

(R)—N-(di(naphthalen-2-yl)methyl)-N-isopropyl-dinaphtho[2,1-d:1',2'-f][1,3,2]-dioxaphosphepin-4-amine Triethylamine (1.87 mL, 13.4 mmol, 5.0 eq.) was added dropwise to a stirred ice-cooled solution of $PCl_3$ (0.23 mL, 2.68 mmol, 1.0 eq.) in $CH_2Cl_2$ (17 mL). The ice bath was removed and the solution left to warm to room temperature before N-(di(naphthalen-2-yl)methyl)propan-2-amine (782 mg, 2.68 mmol, 1.0 eq.) was added to the stirring solution. After 5 additional hours of stirring, (R)-binaphthol (767 mg, 2.68 mmol, 1.0 eq.) was added to the suspension and the subsequent mixture was left to stir for an additional 18 h. The solution was then filtered on a small pad of silica and Celite® and rinsed with $CH_2Cl_2$ (~30 mL). The resulting solution was concentrated under reduced pressure to afford a yellow residue. After flash column chromatography (Petrol: $CH_2Cl_2$: $Et_3N$; 89:10:1→80:20:1 $SiO_2$), the ligand was obtained as a crystalline white solid (1230 mg, 1.92 mmol, 72%). $^1H$ NMR (500 MHz, $CDCl_3$) δ ppm 8.03 (s, 1 H), 7.85-7.96 (m, 7 H), 7.71-7.79 (m, 2 H), 7.66 (br. dd, J=8.5, 1.6 Hz, 2 H), 7.59 (s, 1 H), 7.52-7.57 (m, 2 H), 7.34-7.51 (m, 7 H), 7.26-7.33 (m, 3 H), 7.19-7.24 (m, 1 H), 6.02 (d, J=17.7 Hz, 1 H), 3.63-3.77 (m, 1 H), 1.15 (d, J=6.6 Hz, 3 H), 1.08 (d, J=6.6 Hz, 3 H). $^{13}C$ NMR (125 MHz, $CDCl_3$) δ ppm 150.8 (d, J=7.4 Hz), 150.2, 141.3, 141.2, 133.8, 133.6, 133.2, 133.1, 133.0, 131.8, 130.9, 130.7, 129.9, 128.7, 128.7 (2 C), 128.6 (3 C), 128.4, 128.14, 128.09 (d, J=3.7 Hz), 128.0, 127.7 (d, J=3.7 Hz), 127.6, 127.6, 127.5, 126.6, 126.5, 126.4 (3 C), 126.4, 126.3, 125.1, 124.8, 124.4 (d, J=5.5 Hz), 122.8, 122.6, 122.2, 61.6, 47.5, 23.7, 23.6. $^{31}P$ NMR (200 MHz, $CDCl_3$) δ ppm 150.18 (s, 1P). HRMS (EI) m/z calcd for $C_{44}H_{34}NO_2P$ [M]$^+$: 639.2327, found: 639.2354. $[\alpha]^{20}_{589}$=−67.66 (c 0.99, $CHCl_3$). IR ($v_{max}$/cm$^{-1}$): 2970, 1739, 1367, 1229, 1216, 946, 820, 751.

Example 54

(S)—N-(bis(4-methoxyphenyl)methyl)-N-isopropyl-dinaphtho[2,1-d:1',2'-f][1,3,2]dioxaphosphepin-4-amine

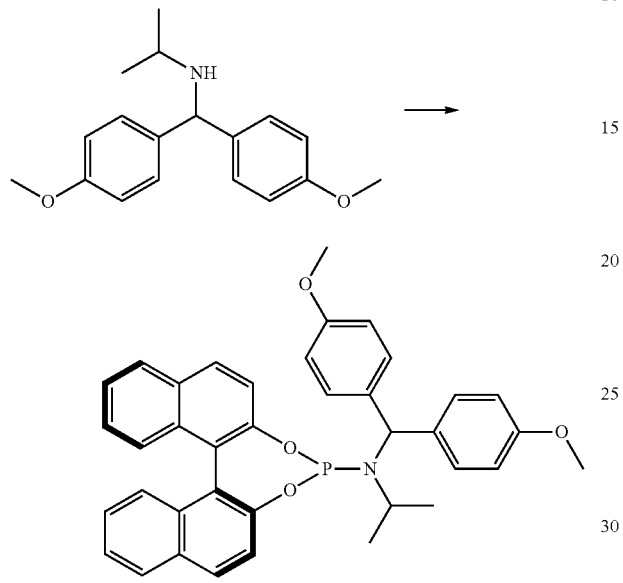

Triethylamine (1.15 mL, 8.28 mmol, 5.0 eq.) was added dropwise to a stirred ice-cooled solution of PCl$_3$ (0.14 mL, 1.66 mmol, 1.0 eq.) in CH$_2$Cl$_2$ (12 mL). The ice bath was removed and the solution left to warm to room temperature before N-(bis(4-methoxyphenyl)methyl)propan-2-amine (472 mg, 1.66 mmol, 1.0 eq.) was added to the stirring solution. After 5 additional hours of stirring, (S)-binaphthol (474 mg, 1.66 mmol, 1.0 eq.) was added to the suspension and the subsequent mixture was left to stir for an additional 18 h. The solution was then filtered on a small pad of silica and Celite® and rinsed with CH$_2$Cl$_2$ (~30 mL). The resulting solution was concentrated under reduced pressure to afford a yellow residue. After flash column chromatography (Petrol: CH$_2$Cl$_2$: Et$_3$N; 80:19:1 SiO$_2$), the ligand was obtained as a crystalline white solid (438 mg, 0.73 mmol, 44%). $^1$H NMR (500 MHz, CDCl$_3$) δ ppm 7.92 (d, J=8.5 Hz, 1 H), 7.89 (dd, J=7.9, 4.1 Hz, 2 H), 7.82 (d, J=8.8 Hz, 1 H), 7.33-7.46 (m, 6 H), 7.25-7.31 (m, 3 H), 7.19-7.24 (m, 5 H), 7.14-7.19 (m, 2 H), 5.65 (d, J=17.3 Hz, 1 H), 3.58 (td, J=6.6, 4.1 Hz, 1 H), 2.40 (s, 3 H), 2.38 (s, 3 H), 1.08 (d, J=6.6 Hz, 3 H), 0.98 (d, J=6.6 Hz, 3 H). $^{13}$C NMR (125 MHz, CDCl$_3$) δ ppm 150.9 (d, J=6.5 Hz, 1 C), 150.4, 141.2 (d, J=5.5 Hz), 141.1 (d, J=3.7 Hz), 137.0, 136.9, 133.2, 133.1, 131.7, 130.9, 130.6, 129.8, 129.4 (2 C), 129.3 (2 C), 129.2 29.2, 129.2, 129.1, 128.7, 128.6, 127.6, 127.5, 126.3, 126.2, 125.1, 124.7, 124.4 (d, J=5.5 Hz), 122.9, 122.7, 122.1 (d, J=2.8 Hz), 60.5, 47.1, 23.6, 23.3, 21.6 (2 C). $^{31}$P NMR (200 MHz, CDCl$_3$) δ ppm 150.85 (s, 1P). HRMS (EI) m/z calcd for C$_{38}$H$_{34}$NO$_2$P [M−1]$^+$: 598.2147. found: 598.2151. [α]$^{20}_{589}$=+144.24 (c 0.99, CHCl$_3$). IR (ν$_{max}$/cm$^{-1}$): 3016, 2970, 1730, 1436, 1369, 1229, 899, 732.

Example 55

(R)—N-(di-p-tolylmethyl)-N-isopropyldinaphtho[2,1-d:1',2'-f][1,3,2]-dioxaphos-phepin-4-amine Triethylamine (1.60 mL, 11.61 mmol, 5.0 eq.) was added dropwise to a stirred ice-cooled solution of PCl$_3$ (0.20 mL, 2.32 mmol, 1.0 eq.) in CH$_2$Cl$_2$ (17 mL). The ice bath was removed and the solution left to warm to room temperature before N-(di-p-tolylmethyl)propan-2-amine (589 mg, 2.32 mmol, 1.0 eq.) was added to the stirring solution. After 5 additional hours of stirring, (R)-binaphthol (665 mg, 2.32 mmol, 1.0 eq.) was added to the suspension and the subsequent mixture was left to stir for an additional 18 h. The solution was then filtered on a small pad of silica and Celite® and rinsed with CH$_2$Cl$_2$ (~30 mL). The resulting solution was concentrated under reduced pressure to afford a yellow residue. After flash column chromatography (Petrol: CH$_2$Cl$_2$: Et$_3$N; 80:19:1 SiO$_2$), the ligand was obtained as a crystalline white solid (574 mg, 1.04 mmol, 43%). $^1$H NMR (500 MHz, CDCl$_3$) δ ppm 7.92 (d, J=8.8 Hz, 1 H), 7.87-7.91 (m, 2 H), 7.82 (d, J=8.8 Hz, 1 H), 7.33-7.46 (m, 7 H), 7.25-7.31 (m, 2H), 7.22 (d, J=7.3 Hz, 5 H), 7.15-7.19 (m, 2 H), 5.65 (d, J=17.7 Hz, 1 H), 3.58 (dq, J=11.0, 6.6 Hz, 1 H), 2.40 (s, 3 H), 2.38 (s, 3 H), 1.08 (d, J=6.6 Hz, 3 H), 0.98 (d, J=6.6 Hz, 3 H). $^{13}$C NMR (125 MHz, CDCl$_3$) δ ppm 150.5 (d, J=6.5 Hz), 149.9, 140.7 (d, J=6.5 Hz), 140.6 (d, J=4.6 Hz), 136.55, 136.51, 132.73, 132.69, 131.3, 130.5, 130.1, 129.3, 129.0 (2 C), 128.9 (2 C), 128.8, 128.7, 128.7, 128.7, 128.2, 128.2, 127.1, 127.0, 125.9, 125.8, 124.6, 124.3, 124.0 (d, J=4.6 Hz), 122.4, 122.2, 121.7, 60.3, 46.7, 23.1, 22.9, 21.13, 21.10. $^{31}$P NMR (200 MHz, CDCl$_3$) δ ppm 150.84 (s, 1P). HRMS (EI) m/z calcd for C$_{38}$H$_{34}$NO$_2$P [M]$^+$: 567.2327, found: 567.2348. [α]$^{20}_{589}$=−157.46 (c 1.00, CHCl$_3$). IR (ν$_{max}$/cm$^{-1}$): 2974, 1510, 1232, 947, 820, 721.

Example 56

(R)—N-(bis(3-(trifluoromethyl)phenyl)methyl)-N-isopropyldinaphtho-[2,1-d:1',2'-f][1,3,2]dioxaphosphepin-4-amine

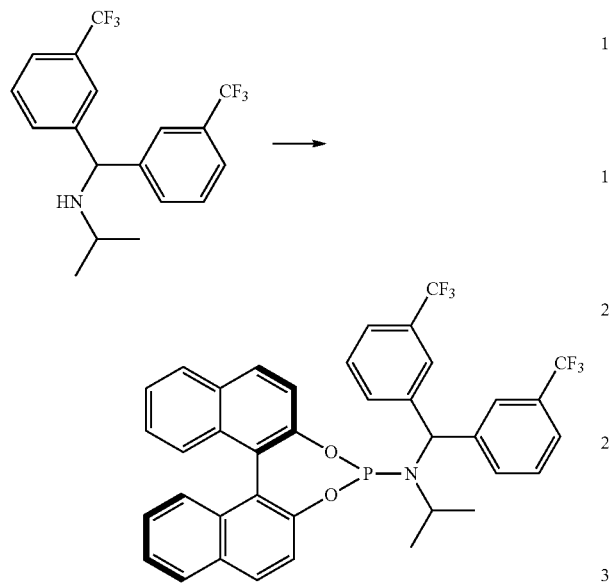

Triethylamine (1.00 mL, 7.72 mmol, 5.0 eq.) was added dropwise to a stirred ice-cooled solution of PCl$_3$ (0.13 mL, 3.11 mmol, 1.0 eq.) in CH$_2$Cl$_2$ (10 mL). The ice bath was removed and the solution left to warm to room temperature before N-(bis(3-(trifluoromethyl)phenyl)methyl)propan-2-amine (521 mg, 1.44 mmol, 1.0 eq.) was added to the stirring solution. After 5 additional hours of stirring, (R)-binaphthol (413 mg, 1.44 mmol, 1.0 eq.) was added to the suspension and the subsequent mixture was left to stir for an additional 18 h. The solution was then filtered on a small pad of silica and Celite® and rinsed with CH$_2$Cl$_2$ (~30 mL). The resulting solution was concentrated under reduced pressure to afford a yellow residue. After flash column chromatography (Petrol: CH$_2$Cl$_2$: Et$_3$N; 80:19:1 SiO$_2$), the ligand was obtained as a crystalline white solid (652 mg, 0.96 mmol, 67%). $^1$H NMR (500 MHz, CDCl$_3$) δ ppm 7.95 (d, J=8.8 Hz, 1 H), 7.89 (t, J=7.6 Hz, 2 H), 7.82 (s, 1 H), 7.79 (d, J=8.8 Hz, 1 H), 7.73 (s, 1 H), 7.61-7.66 (m, 1 H), 7.58 (d, J=7.6 Hz, 1 H), 7.50-7.56 (m, 2 H), 7.46 (t, J=7.6 Hz, 1 H), 7.38-7.44 (m, 4 H), 7.36 (d, J=7.6 Hz, 1 H), 7.19-7.30 (m, 4 H), 5.80 (d, J=16.4 Hz, 1 H), 3.59 (sxt, J=6.2 Hz, 1 H), 1.14 (d, J=6.6 Hz, 3 H), 0.97 (d, J=6.2 Hz, 3 H). $^{13}$C NMR (125 MHz, CDCl$_3$) δ ppm 149.8 (d, J=7.4 Hz), 149.4, 143.7, 132.7 (d, J=9.2 Hz), 132.2, 131.9, 131.4, 131.1, 131.0, 130.8, 130.54, 130.1, 129.5, 129.0, 128.8, 128.3 (d, J=8.3 Hz), 127.1, 127.0, 126.1, 126.0, 125.7 (t, J=4.2 Hz), 125.5 (t, J=3.2 Hz), 125.2 (d, J=2.8 Hz), 124.8, 124.5, 124.3 (dd, J=7.4, 3.7 Hz, 2 C), 123.8 (d, J=5.5 Hz), 123.0 (d, J=2.8 Hz), 122.0, 121.73, 121.69, 60.0 (d, J=23.0 Hz), 47.1, 23.2, 23.0 (d, J=4.6 Hz). $^{31}$P NMR (200 MHz, CDCl$_3$) δ ppm 149.00 (s, 1P). $^{19}$F NMR (380 MHz, CDCl$_3$) δ ppm −62.5 (s, 3 F), −62.6 (s, 3 F). HRMS (EI) m/z calcd for C$_{38}$H$_{28}$F$_6$NO$_2$P [M−1]$^+$: 675.1762, found: 675.1758. [α]$^{20}_{589}$=−159.00 (c 1.01, CHCl$_3$). IR (ν$_{max}$/cm$^{−1}$): 2975, 1591, 1329, 1231, 1165, 1125, 948, 828, 803, 751.

Example 57

(S)—N-benzhydryl-N-cyclooctyldinaphtho[2,1-d:1',2'-f][1,3,2]dioxaphosphe-pin-4-amine

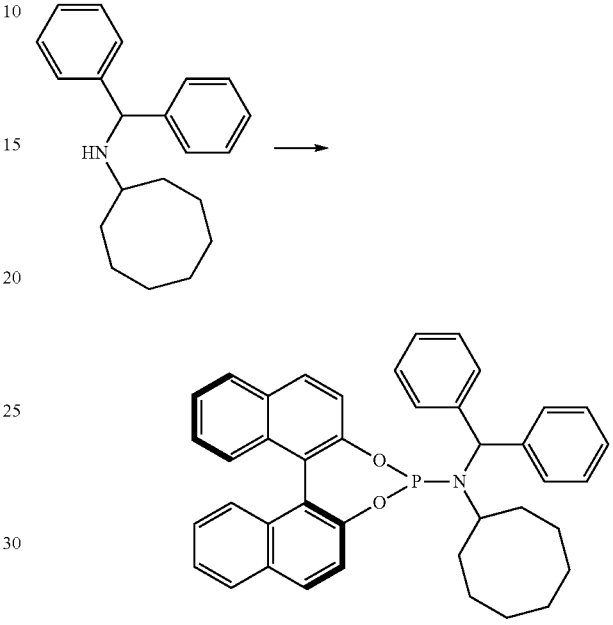

Triethylamine (1.16 mL, 8.34 mmol, 5.0 eq.) was added dropwise to a stirred ice-cooled solution of PCl$_3$ (0.15 mL, 1.67 mmol, 1.0 eq.) in CH$_2$Cl$_2$ (10 mL). The ice bath was removed and the solution left to warm to room temperature before N-benzhydrylcyclooctanamine (490 mg, 1.67 mmol, 1.0 eq.) was added to the stirring solution. After 5 additional hours of stirring, (S)-binaphthol (478 mg, 1.67 mmol, 1.0 eq.) was added to the suspension and the subsequent mixture was left to stir for an additional 18 h. The solution was then filtered on a small pad of silica and Celite® and rinsed with CH$_2$Cl$_2$ (~20 mL). The resulting solution was concentrated under reduced pressure to afford a yellow residue. After flash column chromatography (Petrol: CH$_2$Cl$_2$: Et$_3$N; 80:19:1 SiO$_2$), the ligand was obtained as a crystalline orange solid (350 mg, 0.61 mmol, 36%). $^1$H NMR (500 MHz, CDCl$_3$) δ ppm 7.93 (d, J=8.8 Hz, 1 H), 7.89 (d, J=8.2 Hz, 1 H), 7.85 (d, J=8.2 Hz, 1 H), 7.66-7.77 (m, 1 H), 7.17-7.53 (m, 18 H), 5.70 (d, J=15.1 Hz, 1 H), 3.38 (br. dd, J=7.3, 3.2 Hz, 1 H), 1.58-1.94 (m, 4 H), 1.54 (s, 1 H), 1.30-1.44 (m, 1 H), 0.99-1.26 (m, 5 H), 0.81-0.98 (m, 2 H), 0.65 (br. s., 1 H). $^{13}$C NMR (125 MHz, CDCl$_3$) δ ppm 150.6 (d, J=6.5 Hz), 150.3, 133.2, 131.7, 131.0, 130.6, 130.0 (2 C), 129.1, 129.0, 128.7 (6 C), 128.55 (3 C), 128.51, 127.5, 127.4 (2 C), 127.3, 126.3 (d, J=8.3 Hz), 125.0, 124.8, 124.4 (d, J=4.6 Hz), 122.8, 122.5, 122.2, 62.9, 62.7, 56.3, 26.5 (2 C), 26.1 (2 C), 25.6 (2 C). $^{31}$P NMR (200 MHz, CDCl$_3$) δ ppm 150.05 (s, 1P). HRMS (EI) m/z calcd for C$_{41}$H$_{37}$NO$_2$P [M−1]$^+$: 606.2562, found: 606.2562. [α]$^{20}_{589}$=+178.27 (c 0.99, CHCl$_3$). IR (ν$_{max}$/cm$^{−1}$): 2921, 1591, 1464, 1328, 1237, 1054, 948, 821, 750.

Example 58

(S)—N-benzhydryl-N-cyclohexyl)dinaphtho[2,1-d:1',2'-f][1,3,2]dioxaphos-phepin-4-amine

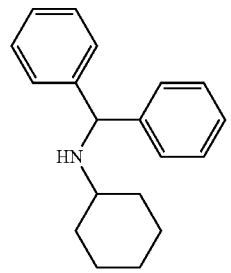

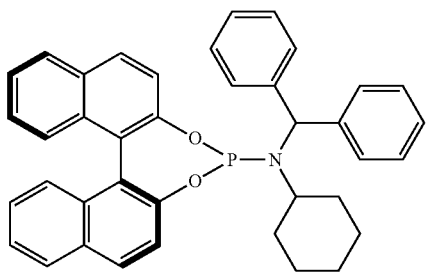

Triethylamine (1.57 mL, 11.30 mmol, 5.0 eq.) was added dropwise to a stirred ice-cooled solution of $PCl_3$ (0.19 mL, 2.26 mmol, 1.0 eq.) in $CH_2Cl_2$ (17 mL). The ice bath was removed and the solution left to warm to room temperature before N-benzhydrylcyclohexanamine (0.60 g, 2.26 mmol, 1.0 eq.) was added to the stirring solution. After 5 additional hours of stirring, (S)-binaphthol (0.65 g, 2.26 mmol, 1.0 eq.) was added to the suspension and the subsequent mixture was left to stir for an additional 18 h. The solution was then filtered on a small pad of silica and Celite® and rinsed with $CH_2Cl_2$ (~30 mL). The resulting solution was concentrated under reduced pressure to afford a yellow residue. After flash column chromatography (Petrol: $CH_2Cl_2$: $Et_3N$; 80:19:1 $SiO_2$), the ligand was obtained as a crystalline yellow solid (0.72 g, 1.21 mmol, 54%). $^1H$ NMR (500 MHz, $CDCl_3$) δ ppm 7.86-8.00 (m, 3 H), 7.78 (d, J=8.5 Hz, 1 H), 7.48-7.56 (m, 2 H), 7.19-7.47 (m, 16 H), 5.77 (d, J=16.7 Hz, 1 H), 3.02 (br. d, J=2.5 Hz, 1 H), 1.80 (d, J=10.1 Hz, 1 H), 1.42-1.68 (m, 4 H), 1.28-1.41 (m, 2 H), 0.91 (q, J=13.1 Hz, 1 H), 0.56-0.73 (m, 2 H). $^{13}C$ NMR (125 MHz, $CDCl_3$) δ ppm 150.3 (d, J=6.5 Hz), 149.8, 143.5 (d, J=6.5 Hz), 143.4, 132.8, 132.6, 131.3, 130.4, 130.1, 129.3, 129.1 (d, J=2.8 Hz), 128.7 (2 C), 128.2 (4 C), 128.1, 128.0 (2 C), 127.0 (2 C), 126.9 (2 C), 125.9, 125.8, 124.6, 124.3, 124.0 (d, J=5.5 Hz), 122.3, 121.9, 121.7 (d, J=2.8 Hz), 60.7, 55.8, 33.8, 33.6, 26.1, 26.0, 25.3. $^{31}P$ NMR (200 MHz, $CDCl_3$) δ ppm 151.28 (s, 1P). HRMS (EI) m/z calcd for $C_{39}H_{34}NO_2P$ $[M]^+$: 579.2327, found: 529.2327. $[α]^{20}_{589}$=+219.32 (c 1.45, $CHCl_3$). IR ($v_{max}/cm^{-1}$): 2937, 2854, 1739, 1449, 1231, 948, 751.

Example 59

(S)—N-benzhydryl-N-cyclopentyldinaphtho[2,1-d:1',2'-f][1,3,2]dioxaphos-phepin-4-amine

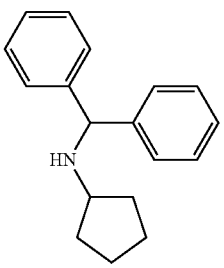

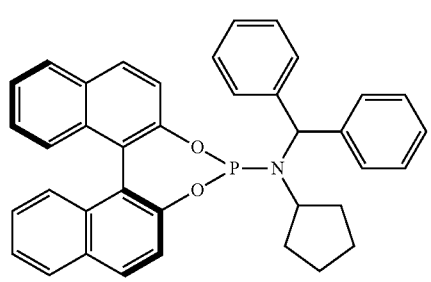

Triethylamine (2.50 mL, 17.9 mmol, 5.0 eq.) was added dropwise to a stirred ice-cooled solution of $PCl_3$ (0.31 mL, 3.58 mmol, 1.0 eq.) in $CH_2Cl_2$ (26 mL). The ice bath was removed and the solution left to warm to room temperature before N-benzhydrylcyclopentanamine (0.90 g, 3.58 mmol, 1.0 eq.) was added to the stirring solution. After 5 additional hours of stirring, (S)-binaphthol (1.02 g, 3.58 mmol, 1.0 eq.) was added to the suspension and the subsequent mixture was left to stir for an additional 18 h. The solution was then filtered on a small pad of silica and Celite® and rinsed with $CH_2Cl_2$ (~30 mL). The resulting solution was concentrated under reduced pressure to afford a yellow residue. After flash column chromatography (Petrol: $CH_2Cl_2$: $Et_3N$; 80:19:1 $SiO_2$), the ligand was obtained as a crystalline white solid (1.02 g, 1.77 mmol, 49%). $^1H$ NMR (500 MHz, $CDCl_3$) δ ppm 7.96 (d, J=8.8 Hz, 1 H), 7.91 (d, J=8.2 Hz, 1 H), 7.84 (d, J=7.9 Hz, 1 H), 7.62 (d, J=8.8 Hz, 1 H), 7.49 (d, J=8.8 Hz, 1 H), 7.34-7.45 (m, 8 H), 7.20-7.33 (m, 8 H), 7.05 (d, J=8.5 Hz, 1 H), 5.70 (d, J=12.3 Hz, 1 H), 3.60 (sxt, J=8.7 Hz, 1 H), 1.90 (d, J=8.5 Hz, 1 H), 1.81 (br. s., 1 H), 1.46-1.64 (m, 2 H), 1.29-1.45 (m, 2H), 1.11-1.27 (m, 2 H). $^{13}C$ NMR (125 MHz, $CDCl_3$) δ ppm 150.0 (d, J=8.3 Hz), 149.7, 143.0 (d, J=3.7 Hz), 142.7, 132.8, 132.5, 131.3, 130.4, 130.2, 129.5, 129.0, 128.6 (d, J=1.8 Hz, 2 C), 128.2, 128.2 (3 C), 128.1, 128.0 (3 C), 127.14, 127.11, 126.9, 125.9, 125.7, 124.7, 124.3, 124.1 (d, J=5.5 Hz), 122.4 (d, J=1.8 Hz), 122.2, 121.6 (d, J=1.8 Hz), 61.4 (d, J=15.7 Hz), 57.7 (d, J=8.3 Hz), 53.4, 32.8, 32.2 (d, J=8.3 Hz), 23.6 (d, J=11.1 Hz). $^{31}P$ NMR (200 MHz, $CDCl_3$) δ ppm 149.78 (s, 1P). HRMS (EI) m/z calcd for $C_{38}H_{32}NO_2P$ $[M]^+$: 565.2171, found: 565.2167. $[α]^{20}_{589}$=+207.75 (c 1.08, $CHCl_3$). IR ($v_{max}/cm^{-1}$): 2958, 2360, 1739, 1590, 1463, 1230, 947, 750.

Example 60

N-(9H-fluoren-9-yl)-N-isopropyldinaphtho[(R)-2,1-d:1',2'-f][1,3,2]dioxa-phosphepin-4-amine

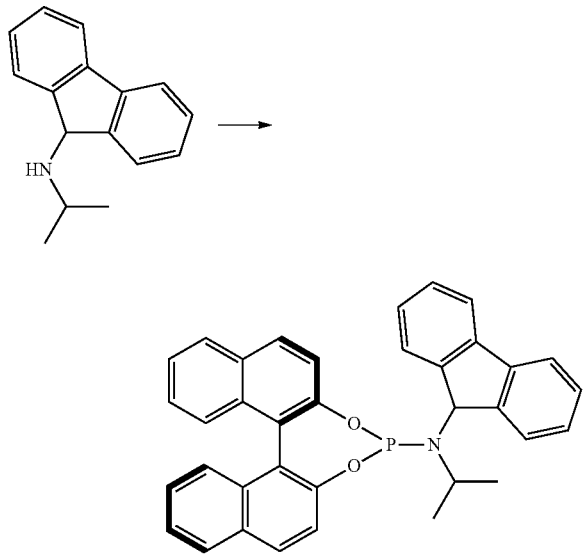

Triethylamine (0.84 mL, 6.0 mmol, 5.0 eq.) was added dropwise to a stirred ice-cooled solution of PCl$_3$ (0.11 mL, 1.2 mmol, 1.0 eq.) in CH$_2$Cl$_2$ (8 mL). The ice bath was removed and the solution left to warm to room temperature before N-isopropyl-9H-fluoren-9-amine (267 mg, 1.2 mmol, 1.0 eq.) was added to the stirring solution. After 5 additional hours of stirring, (R)-binaphthol (219 mg, 1.2 mmol, 1.0 eq.) was added to the suspension and the subsequent mixture was left to stir for an additional 15 h. The solution was then filtered on a small pad of silica and Celite® and rinsed with CH$_2$Cl$_2$ (~15 mL). The resulting solution was concentrated under reduced pressure to afford a yellow residue. After flash column chromatography (Petrol: CH$_2$Cl$_2$: Et$_3$N; 82:17:1 SiO$_2$), the ligand was obtained as a crystalline white solid (364 mg, 0.67 mmol, 56%). $^1$H NMR (500 MHz, CDCl$_3$) δ ppm 8.07 (d, J=8.5 Hz, 1 H), 7.91-8.00 (m, 2 H), 7.86 (d, J=7.3 Hz, 1 H), 7.81 (d, J=8.8 Hz, 1 H), 7.77 (d, J=8.2 Hz, 1 H), 7.72 (d, J=8.5 Hz, 2 H), 7.66 (d, J=6.9 Hz, 1 H), 7.60 (d, J=7.6 Hz, 1 H), 7.43 (quin, J=7.3 Hz, 3 H), 7.23-7.38 (m, 6 H), 7.15-7.22 (m, 1 H), 5.27 (s, 1 H), 2.38-2.54 (m, 1 H), 1.30 (d, J=6.9 Hz, 3 H), 1.09-1.19 (m, 3 H). $^{13}$C NMR (125 MHz, CDCl$_3$) δ ppm 150.3 (d, J=9.2 Hz), 150.1, 145.4, 144.5, 141.7, 140.7, 133.3, 133.1, 131.9, 130.9, 130.2, 128.8, 128.7, 128.6, 128.5, 127.6, 127.6 (2 C), 127.4, 127.2, 126.5, 126.4 (2 C), 126.0, 125.3, 124.9 (2 C), 124.6, 122.8 (d, J=6.5 Hz), 122.0, 120.3, 119.9, 62.5, 48.5, 26.9 (d, J=13.9 Hz), 26.7 (d, J=13.9 Hz). $^{31}$P NMR (200 MHz, CDCl$_3$) δ ppm 149.07 (s, 1P). HRMS (EI) m/z calcd for C$_{36}$H$_{28}$NO$_2$P [M]$^+$: 537.1858, found: 537.1854. [α]$^{20}_{589}$= −87.32 (c 0.99, CHCl$_3$). IR (ν$_{max}$/cm$^{-1}$): 3064, 2966, 1771, 1231, 1072, 947, 821, 747.

Example 61

(R)—N-(bis(2-methoxyphenyl)methyl)-N-isopropyl-dinaphtho[2,1-d:1',2'-f]-[1,3,2]dioxaphosphepin-4-amine

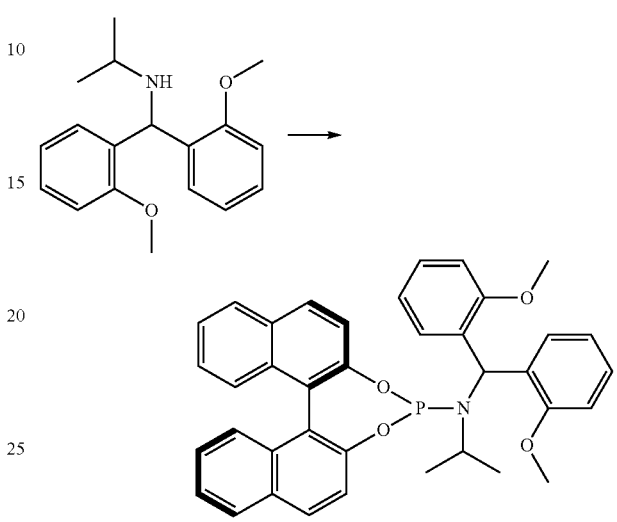

Triethylamine (5.1 mL, 36.7 mmol, 5.00 eq) was added dropwise over about 8 min to a stirred, cooled (water/ice bath) solution of PCl$_3$ (0.64 mL, 7.4 mmol, 1.00 eq) in CH$_2$Cl$_2$ (50 mL). The ice bath was removed and the solution left to warm to room temperature before N-(bis(3-methoxyphenyl)methyl)propan-2-amine (2.1 g, 7.4 mmol, 1.00 eq) was added to the stirring solution. (R)-Binaphthol (2.1 g, 7.4 mmol, 1.00 eq) was added to the suspension after 5 hours and the subsequent mixture was left stirring overnight. The solution was then filtered over a small silica (3 mm) and Celite® (1.5 mm) pad and then washed with CH$_2$Cl$_2$. After removing the solvent in vacuo, flash column chromatography of the yellow residue (80:19:1; Petrol/CH$_2$Cl$_2$/Et$_3$N; SiO$_2$) gave phosphoramidite (R)—N-(bis(3-methoxyphenyl)methyl)-N-isopropyldinaphtho[2,1-d: 1',2'-f][1,3,2]dioxaphosphepin-4-amine (4.2 g, 7.0 mmol, 95%) as a white solid. $^1$H NMR (400 MHz, CDCl$_3$) δ$_H$/ppm 7.85-7.97 (m, 4H), 7.54 (d, J=7.6 Hz, 1 H), 7.51 (d, J=8.9 Hz, 1 H), 7.36-7.47 (m, 5 H), 7.28-7.34 (m, 4 H), 7.19-7.26 (m, 1 H), 6.97-7.06 (m, 2 H), 6.96 (dd, J=8.2, 1.8 Hz, 2 H), 6.45 (d, J=16.3 Hz, 1 H), 3.96 (s, 3 H), 3.88 (s, 3 H), 3.58 (dtd, J=13.3, 6.6, 6.6, 1.8 Hz, 1 H), 1.02 (d, J=6.7 Hz, 3 H), 0.92 (d, J=6.6 Hz, 3 H). $^{13}$C NMR (100 MHz, CDCl$_3$) δ$_C$/ppm 156.7, 156.5, 150.8, 150.2, 132.7, 131.6, 131.4, 131.2, 130.7, 130.5, 130.5, 130.4, 130.0, 129.2, 128.3 (2 C), 128.1 (2 C), 127.1, 127.0, 125.8, 125.7, 124.5, 124.1, 122.6, 122.5, 121.7, 119.9 (2 C), 110.6 (2 C), 55.4 (2 C), 49.1, 48.8, 47.1, 23.0, 21.9. $^{31}$P NMR (160 MHz CDCl$_3$) δ$_P$/ppm 148.8 (d, J=15.6 Hz, 1P). HMRS (EI) m/z calcd for C$_{36}$H$_{30}$NO$_2$P [M]$^+$: 599.2225, found: 599.2231. [α]$^{20}_{589}$=−89.70 (c 2.00, CHCl$_3$). IR (ν$_{max}$/cm$^{-1}$): 2972, 1589, 1463, 1232, 1053, 948, 751, 695.

Example 62

In a similar manner to the experiment described in Example 4, the coupling of 4-phenyl-1-butene and 2-cyclohexen-1-one was evaluated in the presence of catalytic complexes comprising, as a ligand, various compounds of Examples 48-61:

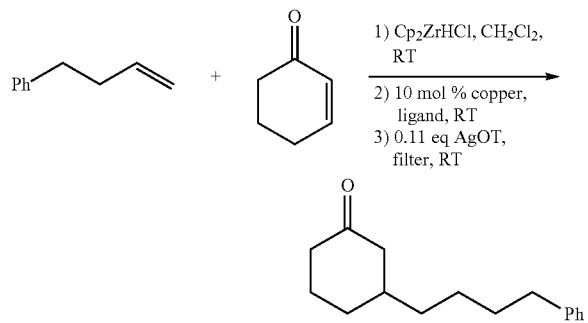

Catalytic complexes comprising these ligands were found to be effective at catalysing the above reaction, and desirable enantioselectivity was attained. For instance, complexes comprising the compounds of Examples 51-53 and 57-59 were found to provide for enantioselectivites of greater than 75%.

It will be understood that the present invention has been described above purely by way of example, and modification of detail can be made within the scope of the invention. Each feature disclosed in the description, and where appropriate the claims, may be provided independently or in any appropriate combination.

The invention claimed is:

1. A compound of the formula (2):

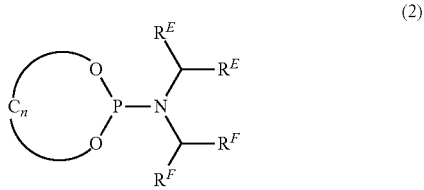

(2)

wherein:
the moiety —O—$C_n$—O— is chiral and is an aliphatic or aromatic diolate, wherein said diolate is optionally substituted;
each $R^E$ is the same and is an achiral substituted or unsubstituted alkyl organic group; and
each $R^F$ is the same and is an achiral substituted or unsubstituted aryl organic group; or $R^F$ and $R^F$, together with the carbon atom to which they are attached, form an achiral substituted or unsubstituted cycloalkyl organic group;
or a salt thereof.

2. The compound according to claim 1, wherein the moiety —O—$C_n$—O— is a moiety derived from a binaphthol compound.

3. The compound according to claim 1, wherein each $R^E$ is phenyl or naphthyl, either of which is optionally substituted.

4. The compound according to claim 3, wherein each $R^E$ is phenyl or phenyl substituted with 1, 2, 3, 4 or 5 substituents independently selected from the group consisting of $C_{1-6}$ alkyl, halogen, trifluoromethyl and $C_{1-6}$ alkoxy.

5. The compound according to claim 4, wherein each $R^E$ is phenyl.

6. The compound according to claim 1, wherein each $R^F$ is optionally substituted $C_{1-6}$ alkyl.

7. The compound according to claim 6, wherein each $R^F$ is methyl.

8. The compound according to claim 1, wherein $R^F$ and $R^F$, together with the carbon atom to which they are attached, form an optionally substituted cycloalkyl group.

9. The compound according to claim 1, wherein each $R^E$ is optionally substituted phenyl or naphthyl; and each $R^F$ is optionally substituted $C_{1-6}$ alkyl, or $R^F$ and $R^F$, together with the carbon atom to which they are attached, form an optionally substituted cycloalkyl group.

10. The compound according to claim 1, wherein each $R^E$ is optionally substituted phenyl; and each $R^F$ is optionally substituted $C_{1-6}$ alkyl, or $R^F$ and $R^F$, together with the carbon atom to which they are attached, form cyclopentyl, cyclohexyl, cycloheptyl or cyclooctyl, any of which is optionally substituted.

11. The compound according to claim 1, wherein each $R^E$ is phenyl or phenyl substituted with 1, 2, 3, 4 or 5 substituents independently selected from $C_{1-6}$ alkyl, halogen, trifluoromethyl and $C_{1-6}$ alkoxy; and each $R^F$ is methyl.

12. The compound according to claim 1, wherein the compound is a compound of formula (C) or (D):

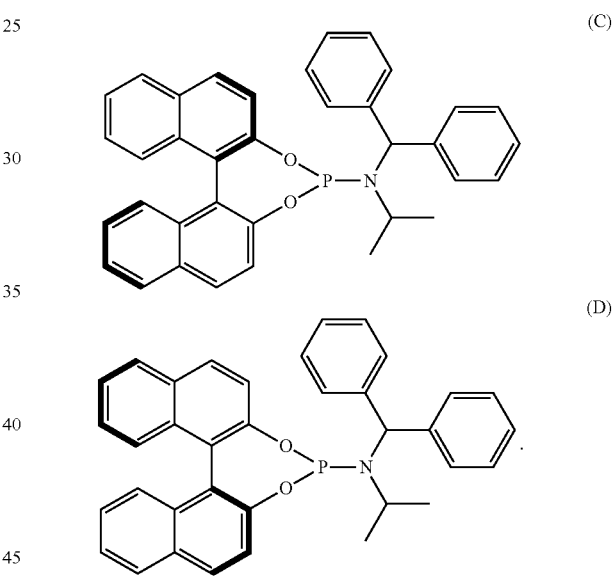

13. A catalytic complex comprising a metal and a ligand, wherein said ligand is a compound of claim 1.

14. The catalytic complex according to claim 13, wherein the catalytic complex further comprises a counterion.

15. The catalytic complex according to claim 14, wherein the counterion is a triflimide counterion.

16. The catalytic complex according to claim 14, wherein said catalytic complex is of the formula M'L'Z', wherein M' is a metal, L' is a ligand which is said compound, and Z' is a counterion.

17. The catalytic complex according to claim 13, wherein the metal is a transition metal.

18. A process for producing a chiral compound in a stereoisomeric excess;
wherein the process comprises:
contacting a first compound comprising an alkene bond with a hydrometallating agent, wherein the first compound and the hydrometallating agent are contacted under conditions such that the first compound is hydrometallated by said hydrometallating agent; and (ii) contacting the hydrometallated first compound with a second compound, wherein the second compound comprises a conjugated π-bond system which is capable of undergoing a 1,4-conjugate addition reaction or a 1,6-conjugate addition reaction and which has a carbon atom at said 4- or 6-position respectively, wherein the hydrometallated first compound and the second compound are contacted under conditions such that they undergo an asymmetric 1,4-conjugate addition reaction or an asymmetric 1,6-conjugate addition reaction in which a carbon atom of said hydrometallated first compound binds to the carbon atom at said 4-position or said 6-position of the second compound, forming a stereoisomeric excess of a compound having a chiral carbon atom at said 4-position or said 6-position;

wherein said asymmetric 1,4-conjugate addition reaction or said asymmetric 1,6-conjugate addition reaction is performed in the presence of the catalytic complex of claim 13.

19. The process according to claim 18, wherein a quaternary centre is formed at the carbon atom at said 4-position or said 6-position.

20. The compound according to claim 2, wherein the moiety —O—$C_n$—O— is a moiety derived from (R)-1,1'-bi-2-naphthol or (S)-1,1'-bi-2-naphthol.

21. The compound according to claim 6, wherein each $R^F$ is optionally substituted methyl, ethyl or propyl.

* * * * *

UNITED STATES PATENT AND TRADEMARK OFFICE
CERTIFICATE OF CORRECTION

| | | |
|---|---|---|
| PATENT NO. | : 9,636,670 B2 | Page 1 of 1 |
| APPLICATION NO. | : 14/784997 | |
| DATED | : May 2, 2017 | |
| INVENTOR(S) | : Fletcher et al. | |

It is certified that error appears in the above-identified patent and that said Letters Patent is hereby corrected as shown below:

In the Claims

Column 87, Line 47, in Claim 1, "unsubstiuted alkyl orgainc group" should read:
--unsubstituted aryl organic group--;

Column 87, Line 49, in Claim 1, "unsubstituted aryl organic group" should read:
--unsubstituted alkyl organic group--; and Column 88, Line 63, in Claim 18, "contacting" should read:
--(i) contacting--.

Signed and Sealed this
First Day of August, 2017

Joseph Matal
*Performing the Functions and Duties of the*
*Under Secretary of Commerce for Intellectual Property and*
*Director of the United States Patent and Trademark Office*